United States Patent [19]

Shuto et al.

[11] Patent Number: 6,015,774
[45] Date of Patent: Jan. 18, 2000

[54] PYRAZIN-2-ONE DERIVATIVES, THEIR USE, AND INTERMEDIATES FOR THEIR PRODUCTION

[75] Inventors: Akira Shuto, Ashiya; Hisayuki Hoshi, Toyonaka; Yuzuru Sanemitsu, Kobe, all of Japan

[73] Assignee: Sumitomo Chemical Company, Limited, Osaka, Japan

[21] Appl. No.: 09/043,470

[22] PCT Filed: Sep. 18, 1996

[86] PCT No.: PCT/JP96/02671

§ 371 Date: Mar. 20, 1998

§ 102(e) Date: Mar. 20, 1998

[87] PCT Pub. No.: WO97/11060

PCT Pub. Date: Mar. 27, 1997

[30] Foreign Application Priority Data

Sep. 22, 1995 [JP] Japan .................................. 7-244107
May 17, 1996 [JP] Japan .................................. 8-123566

[51] Int. Cl.[7] ..................... A01N 43/60; C07D 241/18; C07D 403/04; C07D 405/04; C07D 413/04
[52] U.S. Cl. ..................... 504/221; 544/52; 544/105; 544/354; 544/405; 544/408; 504/225; 504/235
[58] Field of Search ..................... 544/52, 105, 354, 544/405, 408; 504/221, 225, 235

[56] References Cited

U.S. PATENT DOCUMENTS

| 3,501,472 | 3/1970 | Wilcox et al. | 260/250 |
| 5,643,855 | 7/1997 | Kilama et al. | 504/224 |

FOREIGN PATENT DOCUMENTS

| 0146282A2 | 6/1985 | European Pat. Off. |
| 0272914A3 | 6/1988 | European Pat. Off. |
| 2012763 | 8/1979 | United Kingdom |

OTHER PUBLICATIONS

Chemical Abstracts vol. 115, Aug. 5, 1991, No. 5, 115:48626d "Electrochemical and spectrophotometric studies of 2–hydroxy–3–(p–hydroxy–henyl)–6–methylpyrazine".

*Primary Examiner*—Mukund J. Shah
*Assistant Examiner*—Ann M. Kessinger
*Attorney, Agent, or Firm*—Birch, Stewart, Kolasch & Birch, LLP

[57] ABSTRACT

Novel pyrazin-2-one derivatives of formula [1] are provided,

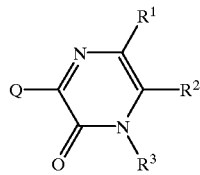

[1]

which are useful as active ingredients of herbicides, wherein $R^1$ is hydrogen or alkyl; $R^2$ is haloalkyl; $R^3$ is optionally substituted alkyl; alkenyl, or alkynyl; and Q is optionally substituted phenyl. Also provided are their use and intermediates for their production.

34 Claims, No Drawings

PYRAZIN-2-ONE DERIVATIVES, THEIR USE, AND INTERMEDIATES FOR THEIR PRODUCTION

This application is the national phase under 35 U.S.C. §371 of prior PCT International Application No., PCT/JP96/02671, which has an International filing date of Sep. 18, 1996, which designated the United States of America, the entire contents of which are hereby incorporated by reference.

TECHNICAL FIELD

The present invention relates to pyrazin-2-one derivatives, their use, and intermediates for their production.

DISCLOSURE OF INVENTION

The present inventors have intensively studied to find a compound having excellent herbicidal activity. As a result, they have found that pyrazin-2-one derivatives represented by formula [1] as depicted below have excellent herbicidal activity, thereby completing the present invention.

Thus the present invention provides a compound of the formula:

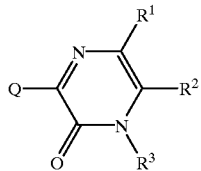

[1]

wherein $R^1$ is hydrogen or $C_1$–$C_3$ alkyl; $R^2$ is $C_1$–$C_3$ haloalkyl; $R^3$ is $C_1$–$C_6$ alkyl optionally substituted with one or more halogen atoms; $C_3$–$C_6$ alkenyl, or $C_3$–$C_6$ alkynyl; and Q is optionally substituted phenyl, (hereinafter referred to as the present compound(s)); and a herbicide containing it as an active ingredient.

The present invention also provides a process for producing compound [1], which comprises reacting a compound of the formula:

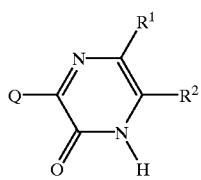

[2]

wherein Q, $R^1$, and $R^2$ are as defined above, with a compound of the formula:

$R^3$—D  [3]

wherein D is chlorine, bromine, iodine, methanesulfonyloxy, trifluoromethanesulfonyloxy, or p-toluenesulfonyloxy; and $R^3$ is as defined above.

The present invention further provides a compound of the formula:

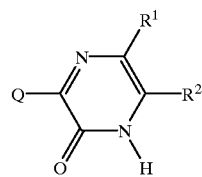

[2]

wherein Q, $R^1$, and $R^2$ are as defined above, which is useful as an intermediate for the production of the present compounds.

Compound [2] may also be present in the form of a compound, which is its tautomer, as depicted below:

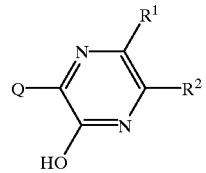

wherein Q, $R^1$, and $R^2$ are as defined above.

In the present invention, the substituent Q may be, for example, [Q-1], [Q-2], [Q-3], [Q-4], or [Q-5] of the formula:

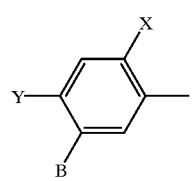

[Q-1]

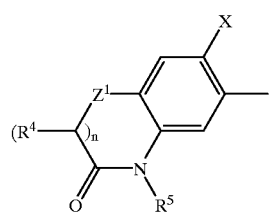

[Q-2]

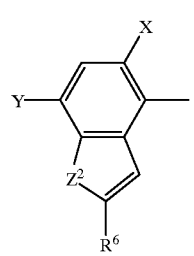

[Q-3]

-continued

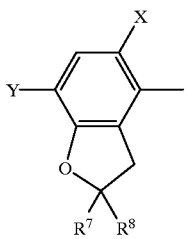
[Q-4]

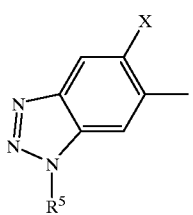
[Q-5]

wherein X is hydrogen or halogen;
Y is halogen, nitro, cyano, or trifluoromethyl;
$Z^1$ is oxygen, sulfur, NH, or methylene;
$Z^2$ is oxygen or sulfur;
n is 0 or 1;
B is hydrogen, halogen, nitro, cyano, chlorosulfonyl, —$OR^{10}$, —$SR^{10}$, —$SO_2OR^{10}$, —$N(R^{10})R^{11}$, —$SO_2N(R^{11})R^{12}$, —$NR^{11}(COR^{13})$, —$NR^{11}(SO_2R^{14})$, —$N(SO_2R^{14})(SO_2R^{15})$, —$N(SO_2R^{14})(COR^{13})$, —$NR^{11}(COOR^{13})$, —$COOR^{13}$, —$CON(R^{11})R^{12}$, —$CSN(R^{11})R^{12}$, —$COR^{16}$, —$CR^{17}=CR^{18}CHO$, —$CR^{17}=CR^{18}COOR^{10}$, —$CR^{17}=CR^{18}CON(R^{11})R^{12}$, —$CH_2CHWCOOR^{13}$, or —$CH_2CHWCON(R^{11})R^{12}$;
$R^4$ is hydrogen or $C_1$–$C_3$ alkyl;
$R^5$ is hydrogen, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_3$–$C_8$ alkoxyalkoxyalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{11})R^{12}$, —$CH_2COON(R^{11})R^{12}$, —$CH(C_1$–$C_4$ alkyl)CON(R^{11})R^{12}$, —$CH(C_1$–$C_4$ alkyl)COON(R^{11})R^{12}$, $C_2$–$C_8$ alkylthioalkyl, $C_1$–$C_6$ alkylsulfonyl, $C_1$–$C_6$ haloalkylsulfonyl, ($C_1$–$C_8$ alkyl)carbonyl, ($C_1$–$C_8$ alkoxy)carbonyl, or hydroxy $C_1$–$C_6$ alkyl;
$R^6$ is $C_1$–$C_6$ alkyl, $C_1$–$C_6$ haloalkyl, formyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, ($C_1$–$C_6$ alkoxy)carbonyl, or ($C_1$–$C_6$ alkyl)carbonyl;
$R^7$ is hydrogen or $C_1$–$C_3$ alkyl; and
$R^8$ is $C_1$–$C_6$ alkyl, $C_1$–$C_6$ haloalkyl, hydroxy $C_1$–$C_6$ alkyl, $C_2$–$C_8$ alkoxyalkyl, $C_3$–$C_{10}$ alkoxyalkoxyalkyl, ($C_1$–$C_5$ alkyl)carbonyloxy $C_1$–$C_6$ alkyl, ($C_1$–$C_6$ haloalkyl)carbonyloxy $C_1$–$C_6$ alkyl, carboxyl, carboxy $C_1$–$C_6$ alkyl, ($C_1$–$C_8$ alkoxy)carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy) carbonyl, aminocarbonyl, ($C_1$–$C_6$ alkyl)aminocarbonyl, di($C_1$–$C_6$ alkyl)aminocarbonyl, ($C_1$–$C_6$ alkyl)aminocarbonyloxy $C_1$–$C_6$ alkyl, or di($C_1$–$C_6$ alkyl)aminocarbonyloxy $C_1$–$C_6$ alkyl;

wherein W is hydrogen, chlorine, or bromine;
$R^{10}$ is hydrogen, $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{11})R^{12}$, —$CH_2COON(R^{11})R^{12}$, —$CH(C_1$–$C_4$ alkyl)CON(R^{11})R^{12}$, or —$CH(C_1$–$C_4$ alkyl)COON(R^{11})R^{12}$;
$R^{11}$ and $R^{12}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, or {($C_1$–$C_4$ alkoxy) $C_1$–$C_4$ alkoxy}carbonyl $C_1$–$C_6$ alkyl, or $R^{11}$ and $R^{12}$ are combined together to form tetramethylene, pentamethylene, or ethyleneoxyethylene;
$R^{13}$ is hydrogen, $C_1$–$C_6$ alkyl, $C_1$–$C_6$ haloalkyl, or $C_3$–$C_8$ cycloalkyl;
$R^{14}$ and $R^{15}$ are independently $C_1$–$C_6$ alkyl, $C_1$–$C_6$ haloalkyl, or phenyl optionally substituted with methyl or nitro;
$R^{16}$ is hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_8$ alkoxyalkyl, or hydroxy $C_1$–$C_6$ alkyl; and
$R^{17}$ and $R^{18}$ are independently hydrogen or $C_1$–$C_6$ alkyl.

In the above definition of the present compounds, the respective substituents are exemplified as follows:

Examples of the $C_1$–$C_3$ alkyl represented by $R^1$ include methyl, ethyl, and isopropyl.

Examples of the $C_1$–$C_3$ haloalkyl represented by $R^2$ include trichloromethyl, trifluoromethyl, difluoromethyl, chlorodifluoromethyl, and pentafluoroethyl.

Examples of the $C_1$–$C_6$ alkyl optionally substituted with one or more halogen atoms, which is represented by $R^3$, include methyl, ethyl, isopropyl, difluoromethyl, and bromodifluoromethyl.

Examples of the $C_3$–$C_6$ alkenyl represented by $R^3$ include allyl and 1-methyl-2-propenyl.

Examples of the $C_3$–$C_6$ alkynyl represented by $R^3$ include propargyl and 1-methyl-2-propynyl.

The respective substituents in formulas [Q-1], [Q-2], [Q-3], [Q-4], and [Q-5] are exemplified as follows:

Examples of the halogen represented by X, Y, and B include chlorine, fluorine, bromine, or iodine.

Examples of the $C_1$–$C_6$ alkyl represented by $R^{10}$ include methyl, ethyl, isopropyl, propyl, isobutyl, butyl, t-butyl, amyl, isoamyl, and t-amyl.

Examples of the $C_1$–$C_6$ haloalkyl represented by $R^{10}$ include difluoromethyl, 1,1,2,2-tetrafluoroethyl, and 2,2,2-trifluoroethyl.

Examples of the $C_3$–$C_8$ cycloalkyl represented by $R^{10}$ include cyclopropyl, cyclobutyl, cyclopentyl, and cyclohexyl.

Examples of the $C_3$–$C_6$ alkenyl represented by $R^{10}$ include allyl, 1-methyl-2-propenyl, 3-butenyl, 2-butenyl, 3-methyl-2-butenyl, and 2-methyl-3-butenyl.

Examples of the $C_3$–$C_6$ haloalkenyl represented by $R^{10}$ include 2-chloro-2-propenyl and 3,3-dichloro-2-propenyl.

Examples of the $C_3$–$C_6$ alkynyl represented by $R^{10}$ include propargyl, 1-methyl-2-propynyl, 2-butynyl, and 1,1-dimethyl-2-propynyl.

Examples of the $C_3$–$C_6$ haloalkynyl represented by $R^{10}$ include 3-bromo-2-propynyl.

Examples of the cyano $C_1$–$C_6$ alkyl represented by $R^{10}$ include cyanomethyl.

Examples of the $C_2$–$C_8$ alkoxyalkyl represented by $R^{10}$ include methoxymethyl, methoxyethyl, ethoxymethyl, and 1-ethoxyethyl.

Examples of the $C_2$–$C_8$ alkylthioalkyl represented by $R^{10}$ include methylthiomethyl and 1-methylthioethyl.

Examples of the carboxy $C_1$–$C_6$ alkyl represented by $R^{10}$ include carboxymethyl, 1-carboxyethyl, and 2-carboxyethyl.

Examples of the ($C_1$–$C_6$ alkoxy)carbonyl $C_1$–$C_6$ alkyl represented by $R^{10}$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the {($C_1$–$C_4$ alkoxy) $C_1$–$C_4$ alkoxy}carbonyl $C_1$–$C_6$ alkyl represented by $R^{10}$ include methoxymethoxycarbonylmethyl and 1-methoxymethoxycarbonylethyl.

Examples of the ($C_3$–$C_8$ cycloalkoxy)carbonyl $C_1$–$C_6$ alkyl represented by $R^{10}$ include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylmethyl, and 1-cyclohexyloxycarbonylethyl.

Examples of the $C_1$–$C_6$ alkyl represented by $R^{11}$ and $R^{12}$ include methyl, ethyl, propyl, butyl, isopropyl, and isobutyl.

Examples of the $C_1$–$C_6$ haloalkyl represented by $R^{11}$ and $R^{12}$ include chloroethyl and bromoethyl.

Examples of the $C_3$–$C_6$ alkenyl represented by $R^{11}$ and $R^{12}$ include allyl, 1-methyl-2-propenyl, and 3-butenyl.

Examples of the $C_3$–$C_6$ alkynyl represented by $R^{11}$ and $R^{12}$ include propargyl and 1-methyl-2-propynyl.

Examples of the cyano $C_1$–$C_6$ alkyl represented by $R^{11}$ and $R^{12}$ include cyanomethyl.

Examples of the $C_2$–$C_8$ alkoxyalkyl represented by $R^{11}$ and $R^{12}$ include methoxymethyl and 1-methoxyethyl.

Examples of the $C_2$–$C_8$ alkylthioalkyl represented by $R^{11}$ and $R^{12}$ include methylthiomethyl and 1-methylthioethyl.

Examples of the carboxy $C_1$–$C_6$ alkyl represented by $R^{11}$ and $R^{12}$ include carboxymethyl and 1-carboxyethyl.

Examples of the ($C_1$–$C_6$ alkoxy)carbonyl $C_1$–$C_6$ alkyl represented by $R^{11}$ and $R^{12}$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-tbutoxycarbonylethyl, 1-amyloxycarbonylethyl, 1-isoamyloxycarbonylethyl, and 1-t-amyloxycarbonylethyl.

Examples of the {($C_1$–$C_4$ alkoxy) $C_1$–$C_4$ alkoxy}carbonyl $C_1$–$C_6$ alkyl represented by $R^{11}$ and $R^{12}$ include methoxymethoxycarbonylmethyl and 1-methoxymethoxycarbonylethyl.

Examples of the $C_1$–$C_6$ alkyl represented by $R^{13}$ include methyl, ethyl, propyl, butyl, amyl, isopropyl, isobutyl, and isoamyl.

Examples of the $C_1$–$C_6$ haloalkyl represented by $R^{13}$ include 2,2,2-trifluoroethyl, chloromethyl, trichloromethyl, and bromomethyl.

Examples of the $C_3$–$C_8$ cycloalkyl represented by $R^{13}$ include cyclopropyl, cyclobutyl, cyclopentyl, and cyclohexyl.

Examples of the $C_1$–$C_6$ alkyl represented by $R^{14}$ and $R^{15}$ include methyl, ethyl, propyl, butyl, and isopropyl.

Examples of the $C_1$–$C_6$ haloalkyl represented by $R^{14}$ and $R^{15}$ include trifluoromethyl, 2,2,2-trifluoroethyl, 2-chloroethyl, chloromethyl, and trichloromethyl.

Examples of the phenyl optionally substituted by methyl or nitro, which is represented by $R^{14}$ and $R^{15}$, include phenyl, 4-methylphenyl, 2-nitrophenyl, 3-nitrophenyl, and 4-nitrophenyl.

Examples of the $C_1$–$C_6$ alkyl represented by $R^{16}$ include methyl, ethyl, propyl, butyl, amyl, isopropyl, isobutyl, t-butyl, isoamyl, and t-amyl.

Examples of the $C_1$–$C_6$ haloalkyl represented by $R^{16}$ include chloromethyl, dichloromethyl, bromomethyl, dibromomethyl, 1-chloroethyl, 1,1-dichloroethyl, 1-bromoethyl, and 1,1-dibromoethyl.

Examples of the $C_2$–$C_6$ alkenyl represented by $R^{16}$ include vinyl, allyl, 1-propenyl, and 1-methyl-2-propenyl.

Examples of the $C_2$–$C_6$ haloalkenyl represented by $R^{16}$ include 3,3-dichloro-2-propenyl and 3,3-dibromo-2-propenyl.

Examples of the $C_2$–$C_6$ alkynyl represented by $R^{16}$ include ethynyl and 2-butynyl.

Examples of the $C_2$–$C_6$ haloalkynyl represented by $R^{16}$ include 3-bromo-2-propynyl.

Examples of the $C_2$–$C_8$ alkoxyalkyl represented by $R^{16}$ include methoxymethyl, methoxyethyl, and isopropoxymethyl.

Examples of the hydroxy $C_1$–$C_6$ alkyl represented by $R^{16}$ include hydroxymethyl.

Examples of the $C_1$–$C_6$ alkyl represented by $R^{17}$ and $R^{18}$ include methyl.

Examples of the $C_1$–$C_3$ alkyl represented by $R^4$ include methyl.

Examples of the $C_1$–$C_6$ alkyl represented by $R^5$ include methyl, ethyl, propyl, butyl, amyl, isopropyl, isobutyl, and isoamyl.

Examples of the $C_1$–$C_6$ haloalkyl represented by $R^5$ include 2-chloroethyl, 2-bromoethyl, 3-chlorobutyl, 3-bromobutyl, difluoromethyl, and bromodifluoromethyl.

Examples of the $C_3$–$C_6$ alkenyl represented by $R^5$ include allyl, 1-methyl-2-propenyl, 3-butenyl, 2-butenyl, 3-methyl-2-butenyl, and 2-methyl-3-butenyl.

Examples of the $C_3$–$C_6$ haloalkenyl represented by $R^5$ include 2-chloro-2-propenyl and 3,3-dichloro-2-propenyl.

Examples of the $C_3$–$C_6$ alkynyl represented by $R^5$ include propargyl, 1-methyl-2-propynyl, 2-butynyl, and 1,1-dimethyl-2-propynyl.

Examples of the $C_3$–$C_6$ haloalkynyl represented by $R^5$ include 3-iodo-2-propynyl and 3-bromo-2-propynyl.

Examples of the cyano $C_1$–$C_6$ alkyl represented by $R^5$ include cyanomethyl.

Examples of the $C_2$–$C_8$ alkoxyalkyl represented by $R^5$ include methoxymethyl, ethoxymethyl, and 1-methoxyethyl.

Examples of the $C_3$–$C_8$ alkoxyalkoxyalkyl represented by $R^5$ include methoxyethoxymethyl.

Examples of the carboxy $C_1$–$C_6$ alkyl represented by $R^5$ include carboxymethyl, 1-carboxyethyl, and 2-carboxyethyl.

Examples of the ($C_1$–$C_6$ alkoxy)carbonyl $C_1$–$C_6$ alkyl represented by $R^5$ include methoxycarbonylmethyl, ethoxycarbonylmethyl, propoxycarbonylmethyl, isopropoxycarbonylmethyl, butoxycarbonylmethyl, isobutoxycarbonylmethyl, t-butoxycarbonylmethyl, amyloxycarbonylmethyl, isoamyloxycarbonylmethyl, t-amyloxycarbonylmethyl, 1-methoxycarbonylethyl, 1-ethoxycarbonylethyl, 1-propoxycarbonylethyl, 1-isopropoxycarbonylethyl, 1-butoxycarbonylethyl, 1-isobutoxycarbonylethyl, 1-t-butoxycarbonylethyl, 1-amyloxycarbonylethyl, 1-isoamyloxycarbonylethyl, and 1-t-amyloxycarbonylethyl.

Examples of the {($C_1$–$C_4$ alkoxy) $C_1$–$C_4$ alkoxy}carbonyl $C_1$–$C_6$ alkyl represented by $R^5$ include methoxymethoxycarbonylmethyl and 1-methoxymethoxycarbonylethyl.

Examples of the ($C_3$–$C_8$ cycloalkoxy)carbonyl $C_1$–$C_6$ alkyl represented by $R^5$ include cyclobutyloxycarbonylmethyl, cyclopentyloxycarbonylmethyl, cyclohexyloxycarbonylmethyl, 1-cyclobutyloxycarbonylethyl, 1-cyclopentyloxycarbonylethyl, and 1-cyclohexyloxycarbonylethyl.

Examples of the $C_2$–$C_8$ alkylthioalkyl represented by $R^5$ include methylthiomethyl and 1-methylthioethyl.

Examples of the $C_1$–$C_6$ alkylsulfonyl represented by $R^5$ include methanesulfonyl, ethanesulfonyl, and isopropylsulfonyl.

Examples of the $C_1$–$C_6$ haloalkylsulfonyl represented by $R^5$ include trifluoromethanesulfonyl, chloromethanesulfonyl, trichloromethanesulfonyl, 2-chloroethanesulfonyl, and 2,2,2-trifluoroethanesulfonyl.

Examples of the ($C_1$–$C_8$ alkyl)carbonyl represented by $R^5$ include acetyl, ethylcarbonyl, propylcarbonyl, and isopropylcarbonyl.

Examples of the ($C_1$–$C_8$ alkoxy)carbonyl represented by $R^5$ include methoxycarbonyl, ethoxycarbonyl, propoxycarbonyl, butoxycarbonyl, amyloxycarbonyl, isopropoxycarbonyl, isobutoxycarbonyl, t-butoxycarbonyl, isoamyloxycarbonyl, and t-amyloxycarbonyl.

Examples of the hydroxy $C_1$–$C_6$ alkyl represented by $R^5$ include hydroxymethyl, hydroxyethyl, and hydroxypropyl.

Examples of the $C_1$–$C_6$ alkyl represented by $R^6$ include methyl and ethyl.

Examples of the $C_1$–$C_6$ haloalkyl represented by $R^6$ include bromomethyl, dibromomethyl, tribromomethyl, 1-bromoethyl, chloromethyl, dichloromethyl, and trichloromethyl.

Examples of the hydroxy $C_1$–$C_6$ alkyl represented by $R^6$ include hydroxymethyl.

Examples of the $C_1$–$C_6$ alkoxy $C_1$–$C_6$ alkyl represented by $R^6$ include methoxymethyl, ethoxymethyl, propoxymethyl, and isopropoxymethyl.

Examples of the $C_1$–$C_6$ alkoxy $C_1$–$C_6$ alkoxy $C_1$–$C_6$ alkyl represented by $R^6$ include methoxymethoxymethyl, methoxyethoxymethyl, and ethoxymethoxymethyl.

Examples of the ($C_1$–$C_6$ alkyl)carbonyloxy $C_1$–$C_6$ alkyl represented by $R^6$ include acetyloxymethyl, ethylcarbonyloxymethyl, and isopropylcarbonyloxymethyl.

Examples of the ($C_1$–$C_6$ haloalkyl)carbonyloxy $C_1$–$C_6$ alkyl represented by $R^6$ include trifluoroacetyloxymethyl, chloroacetyloxymethyl, and trichloroacetyloxymethyl.

Examples of the ($C_1$–$C_6$ alkoxy)carbonyl represented by $R^6$ include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

Examples of the ($C_1$–$C_6$ alkyl)carbonyl represented by $R^6$ include methylcarbonyl, ethylcarbonyl, and isopropylcarbonyl.

Examples of the $C_1$–$C_3$ alkyl represented by $R^7$ include methyl.

Examples of the $C_1$–$C_6$ alkyl represented by $R^8$ include methyl and ethyl.

Examples of the $C_1$–$C_6$ haloalkyl represented by $R^8$ include chloromethyl, bromomethyl, and fluoromethyl.

Examples of the hydroxy $C_1$–$C_6$ alkyl represented by $R^8$ include hydroxymethyl.

Examples of the $C_2$–$C_8$ alkoxyalkyl represented by $R^8$ include methoxymethyl, ethoxymethyl, isopropoxymethyl, butoxymethyl, and isobutoxymethyl.

Examples of the $C_3$–$C_{10}$ alkoxyalkoxyalkyl represented by $R^8$ include methoxymethoxymethyl, methoxyethoxymethyl, and ethoxymethoxymethyl.

Examples of the ($C_1$–$C_5$ alkyl)carbonyloxy $C_1$–$C_6$ alkyl represented by $R^8$ include acetyloxymethyl, ethylcarbonyloxymethyl, and isopropylcarbonyloxymethyl.

Examples of the ($C_1$–$C_6$ haloalkyl)carbonyloxy $C_1$–$C_6$ alkyl represented by $R^8$ include 2-chloroethylcarbonyloxymethyl, trifluoroacetyloxymethyl, and pentafluoroethylcarbonyloxymethyl.

Examples of the carboxy $C_1$–$C_6$ alkyl represented by $R^8$ include carboxymethyl and 1-carboxyethyl.

Examples of the ($C_1$–$C_8$ alkoxy)carbonyl represented by $R^8$ include methoxycarbonyl, ethoxycarbonyl, propoxycarbonyl, butoxycarbonyl, amyloxycarbonyl, isopropoxycarbonyl, isobutoxycarbonyl, and isoamyloxycarbonyl.

Examples of the ($C_1$–$C_6$ haloalkoxy)carbonyl represented by $R^8$ include 2-chloroethoxycarbonyl, 2-bromoethoxycarbonyl, 3-chlorobutoxycarbonyl, 1-chloro-2-propoxycarbonyl, 1,3-dichloro-2-propoxycarbonyl, 2,2-dichloroethoxycarbonyl, 2,2,2-trifluoroethoxycarbonyl, 2,2,2-trichloroethoxycarbonyl, and 2,2,2-tribromoethoxycarbonyl.

Examples of the ($C_3$–$C_{10}$ cycloalkoxy)carbonyl represented by $R^8$ include cyclobutyloxycarbonyl, cyclopentyloxycarbonyl, and cyclohexyloxycarbonyl.

Examples of the ($C_3$–$C_8$ alkenyloxy)carbonyl represented by $R^8$ include allyloxycarbonyl and 3-butenyloxycarbonyl.

Examples of the ($C_3$–$C_8$ alkynyloxy)carbonyl represented by $R^8$ include propargyloxycarbonyl, 3-butynyloxycarbonyl, and 1-methyl-2-propynyloxycarbonyl.

Examples of the ($C_1$–$C_6$ alkyl)aminocarbonyl represented by $R^8$ include methylaminocarbonyl, ethylaminocarbonyl, and propylaminocarbonyl.

Examples of the di($C_1$–$C_6$ alkyl)aminocarbonyl represented by $R^8$ include dimethylaminocarbonyl, diethylaminocarbonyl, and diisopropylaminocarbonyl.

Examples of the ($C_1$–$C_6$ alkyl)aminocarbonyloxy $C_1$–$C_6$ alkyl represented by $R^8$ include methylaminocarbonyloxymethyl, ethylaminocarbonyloxymethyl, and propylaminocarbonyloxymethyl.

Examples of the di($C_1$–$C_6$ alkyl)aminocarbonyloxy $C_1$–$C_6$ alkyl represented by $R^8$ include dimethylaminocarbonyloxymethyl and diethylaminocarbonyloxymethyl.

In the present compounds, preferred substituents from the viewpoint of their herbicidal activity are as follows:

$R^1$ is preferably hydrogen;

$R^2$ is preferably methyl substituted with one or more fluorine atoms, such as trifluoromethyl, difluoromethyl, or chlorodifluoromethyl; or ethyl substituted with one or more fluorine atoms, such as pentafluoroethyl; and more preferably trifluoromethyl;

$R^3$ is preferably methyl or ethyl, and more preferably methyl;

Q is preferably [Q-1], [Q-2], [Q-3], or [Q-4];

Y is preferably halogen;

$Z^1$ is preferably oxygen or sulfur;

$Z^2$ is preferably oxygen;

B is preferably hydrogen, nitro, —$OR^{10}$, —$SR^{10}$, —$NHR^{10}$, —$NHSO_2R^{14}$, —$COOR^{13}$, or —$CH_2CHWCOOR^{13}$; wherein W is preferably hydrogen or chlorine; $R^{10}$ is preferably $C_1$–$C_6$ alkyl, $C_3$–$C_6$ cycloalkyl, $C_3$–$C_6$ alkenyl, $C_3$–$C_6$ haloalkenyl, $C_3$–$C_6$ alkynyl, cyano $C_1$–$C_6$ alkyl, or ($C_1$–$C_6$ alkoxy)carbonyl $C_1$–$C_6$ alkyl; $R^{13}$ is preferably $C_1$–$C_6$ alkyl; and $R^{14}$ is preferably $C_1$–$C_6$ alkyl;

$R^5$ is preferably $C_1$–$C_6$ alkyl, $C_3$–$C_6$ alkenyl, or $C_3$–$C_6$ alkynyl;

$R^6$ is $C_1$–$C_6$ alkyl, $C_1$–$C_6$ haloalkyl, formyl, hydroxymethyl, $C_1$–$C_6$ alkoxymethyl, $C_1$–$C_6$ alkylcarbonyloxymethyl, or $C_1$–$C_6$ alkoxycarbonyl;

$R^7$ is preferably hydrogen or methyl;

$R^8$ is preferably methyl, hydroxymethyl, $C_1$–$C_6$ alkoxymethyl, ($C_1$–$C_5$ alkyl)carbonyloxymethyl, carboxyl, or ($C_1$–$C_6$ alkoxy)carbonyl;

Preferred examples of the present compounds from the viewpoint of their herbicidal activity are those which contain the above preferred substituents in combination. Among these compounds are more preferred ones wherein Q is [Q-1] or [Q-2].

When Q is [Q-1], more preferred compounds are those wherein B is hydrogen, —$OR^{10}$, or —$NHR^{10}$. Among these compounds are more preferred ones wherein B is —$OR^{10}$ and $R^{10}$ is $C_3$–$C_6$ alkynyl or ($C_1$–$C_6$ alkoxy)carbonyl $C_1$–$C_6$ alkyl and ones wherein B is —$NHR^{10}$ and $R^{10}$ is ($C_1$–$C_6$ alkoxy)carbonyl $C_1$–$C_6$ alkyl. Among these compounds are more preferred ones wherein $R^{10}$ is $C_3$–$C_4$ alkynyl, ($C_1$–$C_6$ alkoxy)carbonylmethyl, or 1-($C_1$–$C_6$ alkoxy)carbonylethyl. Among these compounds are more preferred ones wherein $R^1$ is hydrogen; $R^3$ is methyl; X is fluorine; and Y is chlorine.

When Q is [Q-2], more preferred compounds are those wherein $Z^1$ is oxygen; n=1; $R^4$ is hydrogen; and $R^5$ is $C_3$–$C_6$ alkynyl. Among these compounds are more preferred ones wherein $R^5$ is $C_3$–$C_4$ alkynyl. Among these compounds are more preferred ones wherein $R^1$ is hydrogen; $R^3$ is methyl; and X is fluorine.

Particularly preferred compounds are, for example, those wherein $R^1$ is hydrogen; $R^2$ is trifluoromethyl; $R^3$ is methyl; Q is [Q-1]; X is fluorine; Y is chlorine; and B is propargyloxy, 1-(ethoxycarbonyl)ethylamino, or hydrogen; and those wherein $R^1$ is hydrogen; $R^2$ is trifluoromethyl; $R^3$ is methyl; Q is [Q-2]; X is fluorine; $Z^1$ is oxygen; n is 1; $R^4$ is hydrogen; and $R^5$ is propargyl.

In the present compounds, preferred compounds from the viewpoint of the selectivity between crop plants and undesired weeds are those wherein $R^1$ is hydrogen; $R^2$ is trifluoromethyl; $R^3$ is methyl; Q is [Q-1]; X is chlorine; Y is chlorine; and B is 1-(ethoxycarbonyl)ethylamino.

Some of the present compounds may have optical isomers on the basis of at least one asymmetric carbon atom. These optical isomers are, of course, also included within the scope of the present invention.

The present compounds can be produced, for example, according to the production processes described below.

Production Process 1

This is the production process according to the following scheme:

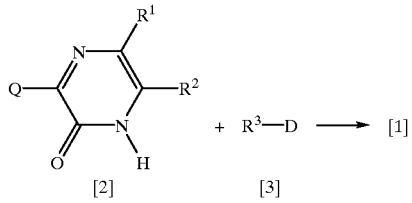

wherein $R^1$, $R^2$, $R^3$, Q, and D are as defined above.

The reaction is usually effected in the presence of a base in a solvent. The reaction temperature is usually in the range of –20° to 250° C., preferably 15° to 150° C., and more preferably 80° to 120° C. The reaction time is usually in the range of a moment to 72 hours, more preferably 48 to 72 hours. The amounts of the reagents to be used in the reaction are usually 1 mole to an excess of compound [3] and usually 1 mole to an excess of the base, per mole of compound [2].

Examples of the solvent which can be used include ketones such as acetone and methyl isobutyl ketone; aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; and mixtures thereof. Among them, N,N-dimethylformamide, acetamide, and 1,2-dichloroethane are preferable.

Examples of the base which can be used include inorganic bases such as sodium hydride, potassium hydride, sodium hydroxide, potassium hydroxide, sodium carbonate, and potassium carbonate; and organic bases such as triethylamine, diisopropylethylamine, pyridine, 4-dimethylaminopyridine, N,N-dimethylaniline, and N,N-diethylaniline.

After completion of the reaction, the reaction mixture is poured into water and the precipitated crystals are collected by filtration, or the reaction mixture is subjected to ordinary post-treatments such as extraction with an organic solvent and concentration, followed by, if necessary, subsequent purification by a technique such as column chromatography or recrystallization. Thus the desired compound of the present invention can be isolated.

In this production process, a compound of the formula:

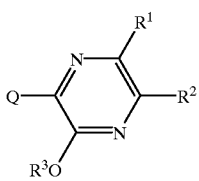

wherein $R^1$, $R^2$, $R^3$, and Q are as defined above, is formed as a by-product depending upon the reaction conditions and can be isolated in a manner similar to the isolation of the above present compound. Some examples of the compound depicted above may also have herbicidal activity.

Production Process 2

This is the production process according to the following scheme:

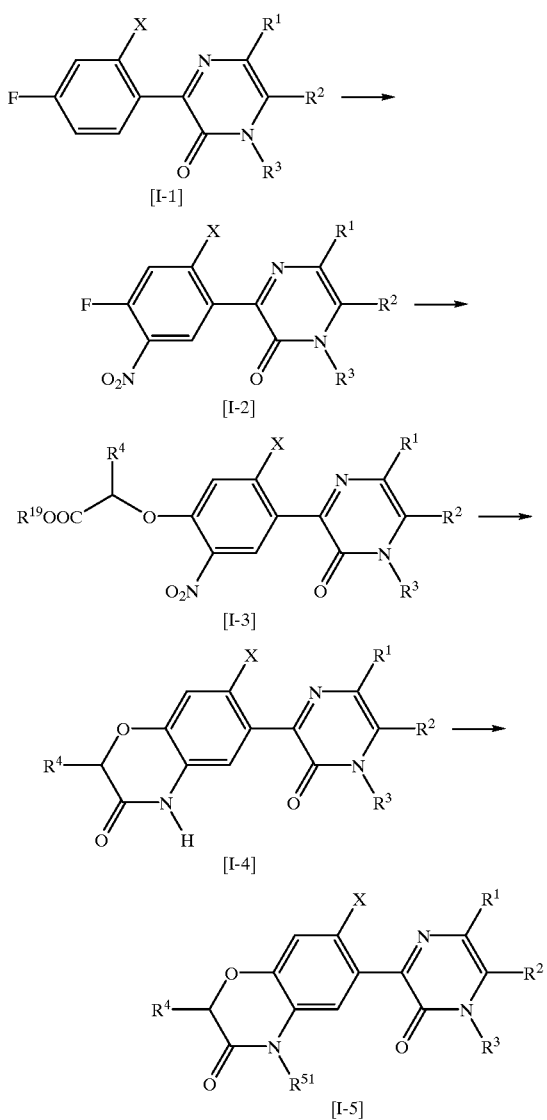

wherein $R^{19}$ is $C_1$–$C_6$ alkyl; $R^{51}$ is a substituent other than hydrogen, which is included in the definition of $R^5$; and $R^1$, $R^2$, $R^3$, $R^4$, and X are as defined above.

Process for Producing Compound [I-2] from Compound [I-1]

Compound [I-2] can be produced by reacting compound [I-1] with a nitrating agent in a solvent.
  Nitrating agent: nitric acid or the like
  Amount of nitrating agent: 1 to 10 moles per mole of compound [I-1]
  Solvent: sulfuric acid or the like
  Temperature: –10° C. to room temperature
  Time: a moment to 24 hours Process for Producing Compound [I-3] from Compound [I-2]

Compound [I-3] can be produced by reacting compound [I-2] with a compound of the formula:

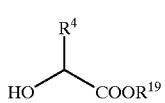

[4]

wherein $R^4$ and $R^{19}$ are as defined above, in the presence of potassium fluoride in a solvent.
  Amount of compound [4]: 1 to 50 moles per mole of compound [I-2]
  Amount of potassium fluoride: 1 to 50 moles per mole of compound [I-2]
  Solvent: 1,4-dioxane or the like
  Temperature: room temperature to refluxing temperature under heating
  Time: a moment to 96 hours Process for Producing Compound [I-4] from Compound [I-3]

Compound [I-4] can be produced by reducing compound [I-3] with iron powder or the like in the presence of an acid in a solvent.
  Amount of iron powder: 3 moles to an excess per mole of compound [I-3]
  Acid: acetic acid or the like
  Amount of acid: 1 mole to an excess per mole of compound [I-3]
  Solvent: water, ethyl acetate, or the like
  Temperature: room temperature to refluxing temperature under heating
  Time: a moment to 24 hours Compound [I-4] can also be produced by reducing compound [I-3] in the presence of a catalyst in a solvent under an atmosphere of hydrogen.
  Catalyst: palladium/carbon or the like
  Amount of catalyst: 0.01 to 1 mole per mole of compound [I-3]
  Solvent: ethyl acetate, acetic acid, mixtures thereof, or the like
  Temperature: room temperature to refluxing temperature under heating
  Time: a moment to 24 hours Process for Producing Compound [I-5] from Compound [I-4]

Compound [I-5] can be produced by reacting compound [I-4] with a compound of the formula:

$$R^{51}\text{—D} \quad [5]$$

wherein $R^{51}$ and D are as defined above.

The reaction is usually effected in the presence of a base in a solvent. The reaction temperature is usually in the range of −20° to 150° C., preferably 0° to 100° C. The reaction time is usually in the range of a moment to 72 hours. The amounts of the reagents to be used in the reaction are usually 1 mole to an excess of compound [5] and usually 1 mole to an excess of the base, per mole of compound [I-4].

Examples of the base which can be used include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Examples of the solvent which can be used include ketones such as acetone and methyl isobutyl ketone; aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol and isopropanol; and mixtures thereof.

After completion of the reaction, the reaction mixture is poured into water, if necessary, and subjected to ordinary post-treatments such as extraction with an organic solvent and concentration, followed by, if necessary, subsequent purification by a technique such as column chromatography or recrystallization. Thus the present compound [I-5] can be obtained.

The above compound [I-3] can also be produced according to the following scheme:

Process for Producing Compound [I-7] from Compound [I-6]

Compound [I-7] can be produced by reacting compound [I-6] with a compound of the formula:

$$\underset{\text{Br}}{\overset{R^4}{\diagdown}}\text{COOR}^{19} \quad [6]$$

wherein $R^4$ and $R^{19}$ are as defined above, in the presence of a base in a solvent.

Amount of compound [6]: 1 to 2 moles per mole of compound [I-6]

Base: sodium hydride, potassium carbonate, or the like

Amount of base: 1 to 5 moles per mole of compound [I-6]

Solvent: 1,4-dioxane, N,N-dimethylformamide, or the like

Temperature: 0° to 100° C.

Time: a moment to 24 hours

Process for Producing Compound [I-3] from Compound [I-7]

Compound [I-3] can be produced by reacting compound [I-7] with a nitrating agent in a solvent.

Nitrating agent: nitric acid or the like

Amount of nitrating agent: 1 to 10 moles per mole of compound [I-7]

Solvent: sulfuric acid or the like

Temperature: −10° C. to room temperature

Time: a moment to 24 hours

Process for Producing Compound [I-8] from Compound [I-6]

Compound [I-8] can be produced by reacting compound [I-6] with a nitrating agent in a solvent.

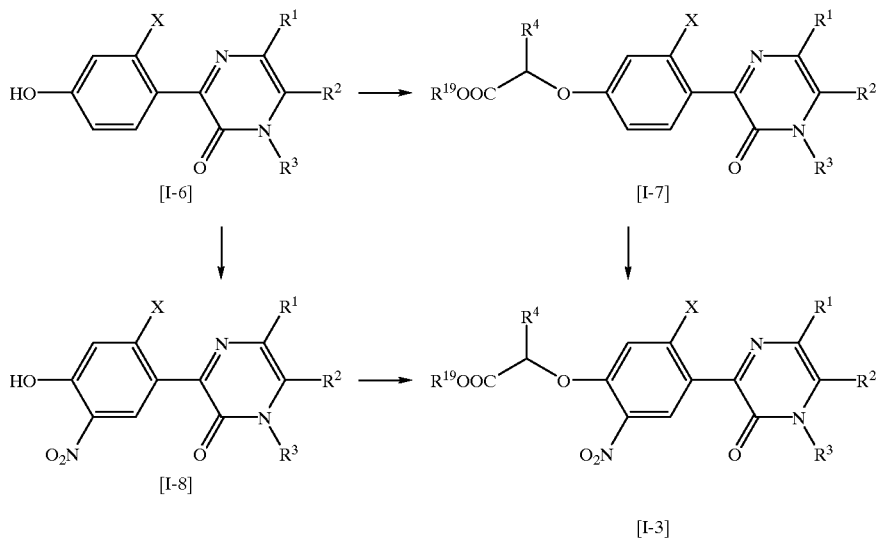

wherein $R^1$, $R^2$, $R^3$, $R^4$, $R^{19}$, and X are as defined above.

Nitrating agent: nitric acid or the like

Amount of nitrating agent: 1 to 10 moles per mole of compound [I-6]

Solvent: sulfuric acid or the like

Temperature: −10° C. to room temperature

Time: a moment to 24 hours

Process for Producing Compound [I-3] from Compound [I-8]

Compound [I-3] can be produced by reacting compound [I-8] with compound [6] in the presence of a base in a solvent.

Amount of compound [6]: 1 to 2 moles per mole of compound [I-8]

Base: sodium hydride, potassium carbonate, or the like

Amount of base: 1 to 5 moles per mole of compound [I-8]

Solvent: 1,4-dioxane, N,N-dimethylformamide, or the like

Temperature: 0° to 100° C.

Time: a moment to 24 hours

Production Process 3

This is the production process according to the following scheme:

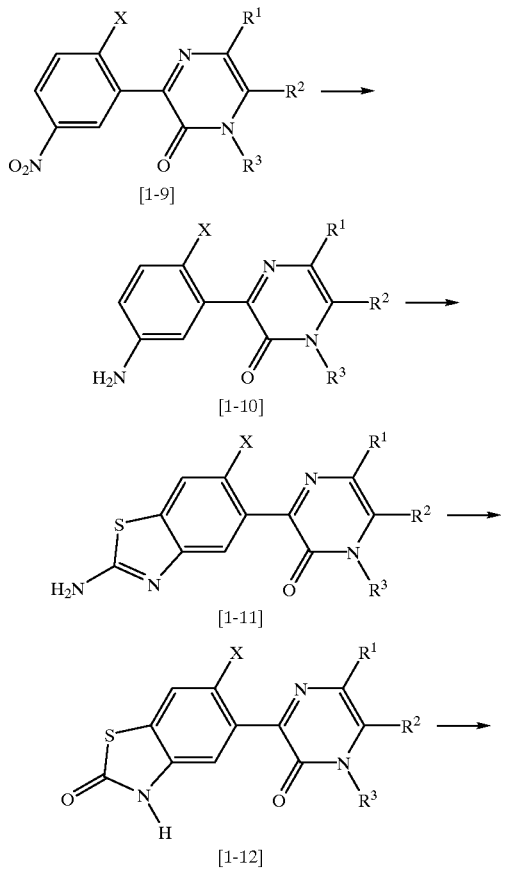

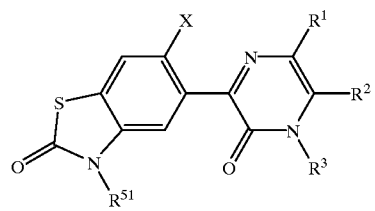

wherein X, $R^1$, $R^2$, $R^3$, and $R^{51}$ are as defined above.

Process for Producing Compound [I-10] from Compound [I-9]

Compound [I-10] can be produced by reducing compound [I-9] with iron powder or the like in the presence of an acid in a solvent.

Amount of iron powder: 3 moles to an excess per mole of compound [I-9]

Acid: acetic acid or the like

Amount of acid: 1 mole to an excess per mole of compound [I-9]

Solvent: water, ethyl acetate, or the like

Temperature: room temperature to refluxing temperature under heating

Time: a moment to 24 hours

Process for Producing Compound [I-11] from Compound [I-10]

Compound [I-11] can be produced by reacting compound [I-10] with sodium thiocyanate, potassium thiocyanate, or the like in a solvent, and then reacting it with bromine or chlorine in a solvent.

Amount of sodium thiocyanate, potassium thiocyanate, or the like: 1 to 10 moles per mole of compound [I-10]

Amount of bromine or chlorine: 1 to 10 moles per mole of compound [I-10]

Solvent: aqueous hydrochloric acid, aqueous acetic acid, aqueous sulfuric acid, or the like Temperature: 0° to 50° C.

Time: a moment to 150 hours

Process for Producing Compound [I-12] from Compound [I-11]

Compound [I-12] can be produced by 1) reacting compound [I-11] with sodium nitrite, potassium nitrite, or the like in a solvent, and then 2) heating it in an acidic solution.

<Reaction 1)>

Amount of sodium nitrite, potassium nitrite, or the like: 1 to 2 moles per mole of compound [I-11]

Solvent: aqueous hydrochloric acid or aqueous sulfuric acid

Temperature: −10° to 10° C.

Time: a moment to 5 hours

<Reaction 2)>

Acidic solution: aqueous hydrochloric acid, aqueous sulfuric acid, or the like

Temperature: 70° C. to refluxing temperature under heating

Time: a moment to 24 hours

Process for Producing Compound [I-13] from Compound [I-12]

Compound [I-13] can be produced by reacting compound [I-12] with compound [5] in the presence of a base in a solvent.

Amount of compound [5]: 1 to 3 moles per mole of compound [I-12]
Base: sodium hydride, potassium carbonate, or the like
Amount of base: 1 to 10 moles per mole of compound [I-12]
Solvent: 1,4-dioxane, N,N-dimethylformamide, or the like
Temperature: 0° to 100° C.
Time: a moment to 48 hours Production Process 4

This is the production process according to the following scheme:

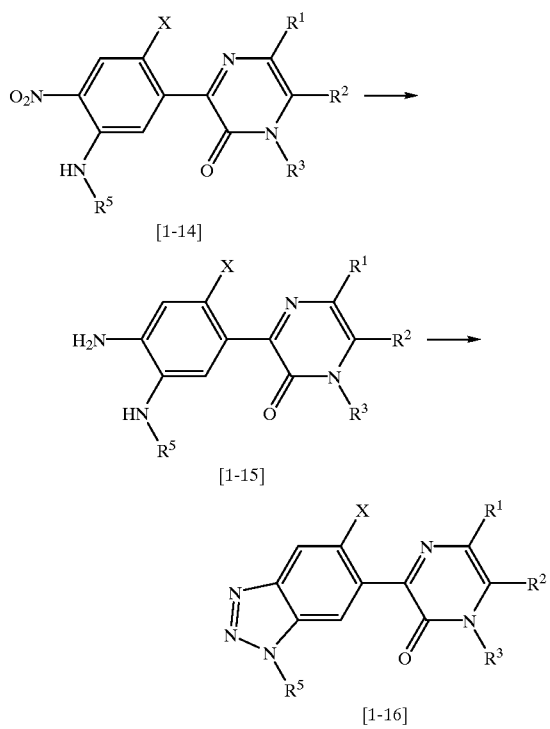

wherein X, $R^1$, $R^2$, $R^3$, and $R^5$ are as defined above.

Process for Producing Compound [I-15] from Compound [I-14]

Compound [I-15] can be produced by reducing compound [I-14] with iron powder or the like in the presence of an acid in a solvent.

Amount of iron powder: 3 moles to an excess per mole of compound [I-14]
Acid: acetic acid or the like
Amount of acid: 1 mole to an excess per mole of compound [I-14]
Solvent: water, ethyl acetate, or the like
Temperature: room temperature to refluxing temperature under heating
Time: a moment to 24 hours Process for Producing Compound [I-16] from Compound [I-15]

Compound [I-16] can be produced by 1) reacting compound [I-15] with a nitrite salt in a solvent to form a diazonium salt, and then 2) raising its temperature to cause the cyclization of the diazonium salt in a solvent.

<Reaction 1>
Nitrite salt: sodium nitrite, potassium nitrite, or the like
Amount of nitrite salt: 1 to 2 moles per mole of compound [I-15]
Solvent: aqueous hydrochloric acid, aqueous sulfuric acid, or the like
Temperature: −10° to 10° C.
Time: a moment to 5 hours <Reaction 2>
Solvent: aqueous hydrochloric acid, aqueous sulfuric acid, or the like
Temperature: room temperature to 80° C.
Time: a moment to 24 hours Production Process 5

This is the production process according to the following scheme:

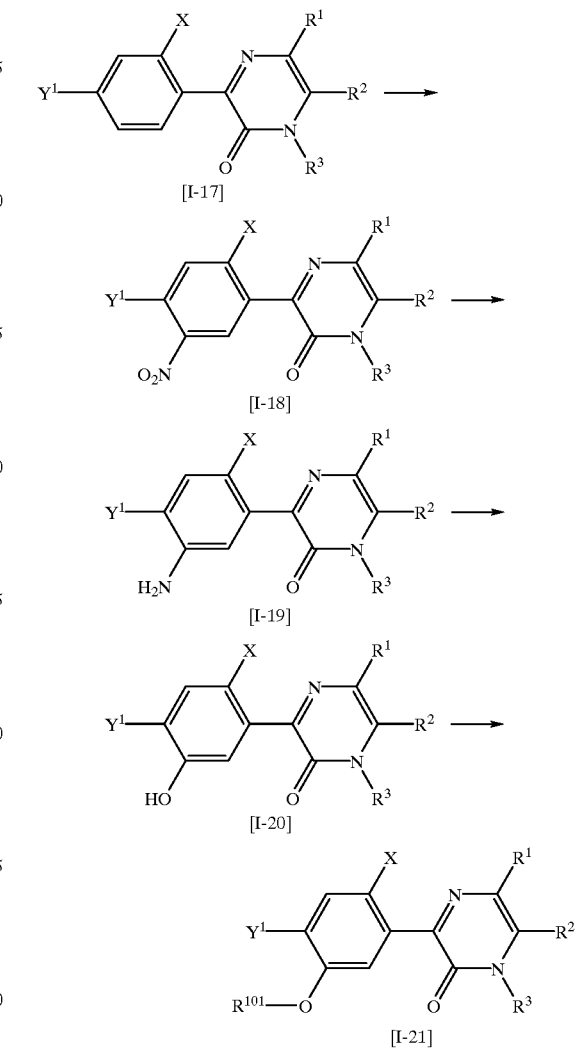

wherein $Y^1$ is a substituent other than nitro, which is included in the definition of Y; $R^{101}$ is a substituent other than hydrogen, which is included in the definition of $R^{10}$; and X, $R^1$, $R^2$, and $R^3$ are as defined above.

Process for Producing Compound [I-18] from Compound [I-17]

Compound [I-18] can be produced by reacting compound [I-17] with a nitrating agent in a solvent.

Nitrating agent: nitric acid or the like
Amount of nitrating agent: 1 to 10 moles per mole of compound [I-17]
Solvent: sulfuric acid or the like
Temperature: −10° C. to room temperature
Time: a moment to 24 hours

Process for Producing Compound [I-19] from Compound [I-18]

Compound [I-19] can be produced by reducing compound [I-18] with iron powder or the like in the presence of an acid in a solvent.

Amount of iron powder: 3 moles to an excess per mole of compound [I-18]
Acid: acetic acid or the like
Amount of acid: 1 mole to an excess per mole of compound [I-18]
Solvent: water, ethyl acetate, or the like
Temperature: room temperature to refluxing temperature under heating
Time: a moment to 24 hours

Process for Producing Compound [I-20] from Compound [I-19]

Compound [I-20] can be produced by 1) reacting compound [I-19] with a nitrite salt in a solvent, and then 2) heating it in an acidic solvent.

<Reaction 1)>
Nitrite salt: sodium nitrite, potassium nitrite, or the like
Amount of nitrate salt: 1 to 2 moles per mole of compound [I-19]
Solvent: aqueous hydrochloric acid, aqueous sulfuric acid, or the like
Temperature: −10° to 10° C.
Time: a moment to 5 hours <Reaction 2)>
Acidic solvent: aqueous hydrochloric acid or aqueous sulfuric acid
Temperature: 70° C. to refluxing temperature under heating
Time: a moment to 24 hours.

Process for Producing Compound [I-21] from Compound [I-20]

Compound [I-21] can be produced by reacting compound [I-20] with a compound of the formula:

$$R^{101}-D \qquad [7]$$

wherein $R^{101}$ and D are as defined above.

The reaction is usually effected in the presence of a base in a solvent. The reaction temperature is usually in the range of −20° to 150° C., preferably 0° to 50° C. The reaction time is usually in the range of a moment to 48 hours. The amounts of the reagents to be used in the reaction are usually 1 to 3 moles of compound [7] and usually 1 to 5 moles of the base, per mole of compound [I-20].

Examples of the base which can be used include inorganic bases such as sodium hydride, potassium hydride, sodium hydroxide, potassium hydroxide, potassium carbonate, and sodium carbonate; and organic bases such as triethylamine, diisopropylethylamine, pyridine, 4-dimethylaminopyridine, N,N-dimethylaniline, and N,N-diethylaniline.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chlorobenzene and dichlorobenzene; ethers such as diethyl ether, diisopropyl ether, dioxane, tetrahydrofuran, and ethylene glycol dimethyl ether; nitro compounds such as nitrobenzene; acid amides such as formamide, N,N-dimethylformamide, and acetamide; tertiary amines such as pyridine, triethylamine, diisopropylethylamine, N,N-dimethylamine, N,N-diethylaniline, and N-methylmorpholine; and mixtures thereof.

After completion of the reaction, the reaction mixture is poured into water, if necessary, and subjected to ordinary post-treatments such as extraction with an organic solvent and concentration, followed by, if necessary, subsequent purification by a technique such as column chromatography or recrystallization. Thus the present compound [I-21] can be isolated.

Compound [I-20] can also be produced by the following process:

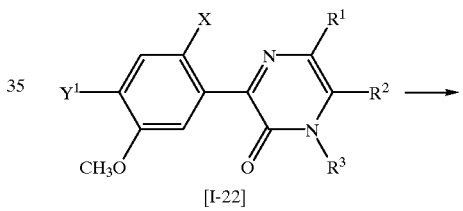

[I-22]

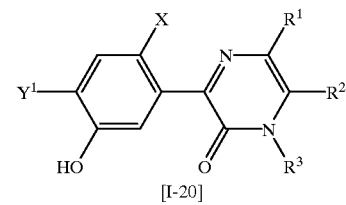

[I-20]

wherein X, $Y^1$, $R^1$, $R^2$, and $R^3$ are as defined above.

Process for Producing Compound [I-20] from Compound [I-22]

Compound [I-20] can be produced by deprotecting compound [I-22] in the presence of hydrogen bromide-acetic acid without any solvent.

Amount of hydrogen bromide-acetic acid: 10 to 100 moles per mole of compound [I-22]
Temperature: 10° to 150° C.
Time: a moment to 24 hours

Production Process 6

This is the production process according to the following scheme:

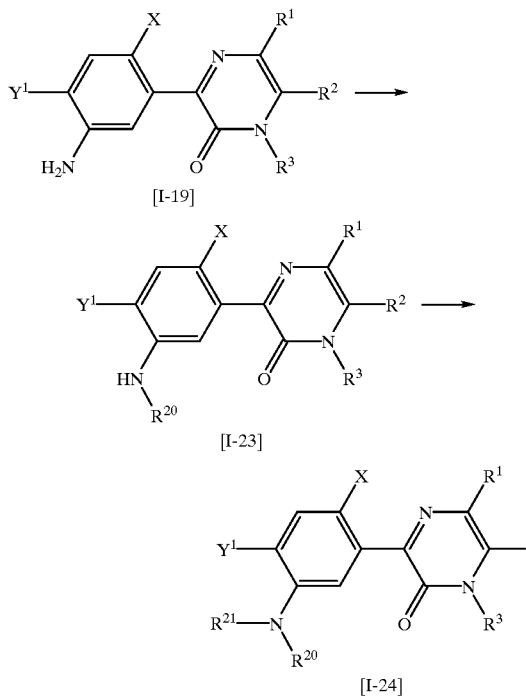

wherein $R^{20}$ and $R^{21}$ are independently a substituent included in the definition of $R^{11}$ or $R^{12}$; or —$COR^{13}$, —$SO_2R^{14}$, —$SO_2R^{15}$, or —$COOR^{13}$, wherein $R^{11}$, $R^{12}$, $R^{13}$, $R^{14}$, and $R^{15}$ are as defined above; and X, $Y^1$, $R^1$, $R^2$, and $R^3$ are as defined above.

Process for Producing Compound [I-23] from Compound [I-19]

Compound [I-23] can be produced by reacting compound [I-19] with a compound of the formula:

 $R^{20}$—D [9]

wherein $R^{20}$ and D are as defined above.

Compound [I-23] can also be produced by reacting compound [I-19] with an acid anhydride of the formula:

 $(R^{20})_2$—O [10]

wherein $R^{20}$ is as defined above, in the presence or absence of a base without any solvent or in a solvent.

Amount of compound [9] or [10]: 1 mole to an excess per mole of compound [I-19]
Base: organic bases such as pyridine and triethylamine; and inorganic bases such as potassium carbonate and sodium hydride
Amount of base: 1 mole to an excess per mole of compound [I-19]
Solvent: N,N-dimethylformamide, 1,4-dioxane, tetrahydrofuran, or the like
Temperature: 0° to 100° C.
Time: a moment to 24 hours

Process for Producing Compound [I-24] from Compound [I-23]

Compound [I-24] can be produced by reacting compound [I-23] with a compound of the formula:

 $R^{21}$—D [11]

wherein $R^{21}$ and D are as defined above.

Compound [I-24] can also be produced by reacting compound [I-23] with an acid anhydride of the formula:

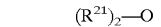 $(R^{21})_2$—O [12]

wherein $R^{21}$ is as defined above, in the presence or absence of a base without any solvent or in a solvent.

Amount of compound [11] or [12]: 1 mole to an excess per mole of compound [I-23]
Base: organic bases such as pyridine and triethylamine; and inorganic bases such as potassium carbonate and sodium hydride
Amount of base: 1 mole to an excess per mole of compound [I-23]
Solvent: N,N-dimethylformamide, 1,4-dioxane, tetrahydrofuran, or the like
Temperature: 0° to 100° C.
Time: a moment to 24 hours

Production Process 7

This is the production process according to the following scheme:

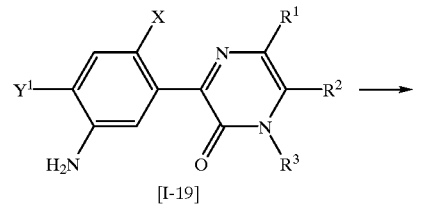

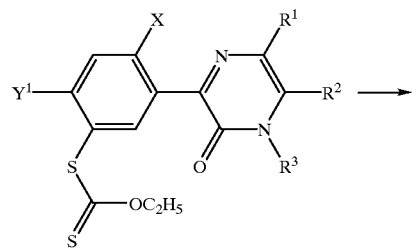

wherein X, $Y^1$, $R^1$, $R^2$, $R^3$, and $R^{101}$ are as defined above.

Process for Producing Compound [I-25] from Compound [I-19]

Compound [I-25] can be produced by 1) reacting compound [I-19] with a nitrite salt in a solvent, and then 2) reacting it with potassium xanthate in a solvent.

<Reaction 1)>

Nitrite salt: sodium nitrite, potassium nitrite, or the like

Amount of nitrite salt: 1 to 2 moles per mole of compound [I-19]

Solvent: aqueous hydrochloric acid, aqueous sulfuric acid, or the like

Temperature: −10° to 10° C.

Time: a moment to 5 hours

<Reaction 2)>

Amount of potassium xanthate: 1 to 2 moles per mole of compound [I-19]

Solvent: aqueous hydrochloric acid, aqueous sulfuric acid, or like

Temperature: 0° to 100° C.

Time: a moment to 24 hours.

(see Org. Syn. Coll., Vol. 3, 809 (1955))

Process for Producing Compound [I-26] from Compound [I-25]

Compound [I-26] can be produced by hydrolyzing compound [I-25] in the presence of a base in a solvent.

Base: inorganic bases such as potassium carbonate

Amount of base: 1 to 5 moles per mole of compound [I-25]

Solvent: alcohols such as methanol and ethanol

Temperature: 0° C. to refluxing temperature under heating

Time: a moment to 24 hours (see Org. Syn. Coll., Vol. 3, 809 (1955))

Process for Producing Compound [I-27] from Compound [I-26]

Compound [I-27] can be produced by reacting compound [I-26] with compound [7] in the presence of a base in a solvent.

Amount of compound [7]: 1 mole to an excess per mole of compound [I-26]

Base: inorganic bases such as potassium carbonate; and organic bases such as triethylamine and pyridine Amount of base: 1 mole to an excess per mole of compound [I-26]

Solvent: 1,4-dioxane, N,N-dimethylformamide, or the like

Temperature: 0° to 100° C.

Time: a moment to 24 hours

Compound [I-26] can also be produced according to the following scheme:

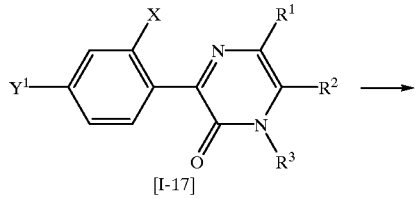

[I-17]

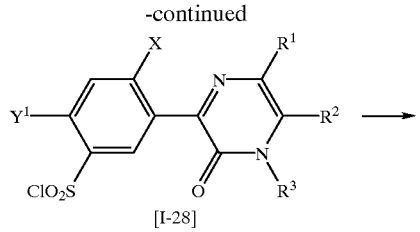

[I-28]

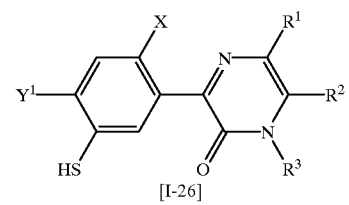

[I-26]

wherein X, Y$^1$, R$^1$, R$^2$, and R$^3$ are as defined above.

Process for Producing Compound [I-28] from Compound [I-17]

Compound [I-28] can be produced by reacting compound [I-17] with chlorosulfonic acid without any solvent or in a solvent.

Amount of chlorosulfonic acid: 1 mole to an excess per mole of compound [I-17]

Solvent: sulfuric acid, or the like

Temperature: 0° to 70° C.

Time: a moment to 24 hours (see Org. Syn. Coll., Vol. 1, 8 (1941))

Process for Producing Compound [I-26] from Compound [I-28]

Compound [I-26] can be produced by reducing compound [I-28] in a solvent.

Reducing agent: zinc, tin chloride, or the like

Amount of reducing agent: 3 moles to an excess per mole of compound [I-28]

Solvent: aqueous acetic acid, aqueous hydrochloric acid, aqueous sulfuric acid, or the like Temperature: room temperature to 100° C.

Time: a moment to 24 hours (see U.S. Pat. No. 4,709,049, column 9)

Production Process 8

This is the production process according to the following scheme:

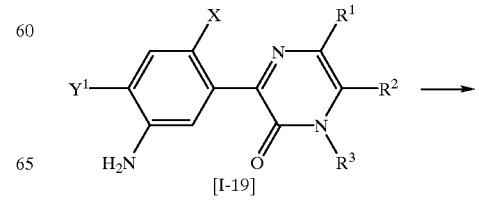

[I-19]

-continued

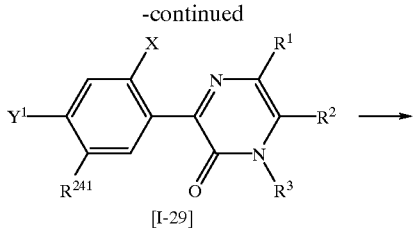
[I-29]

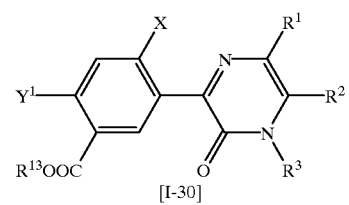
[I-30]

wherein $R^{241}$ is bromine or iodine; and X, $Y^1$, $R^1$, $R^2$, $R^3$, and $R^{13}$ are as defined above.

Process for Producing Compound [I-29] from compound [I-19]

Compound [I-29] can be produced by 1) reacting compound [I-19] with a nitrite salt in a solvent, and then 2) reacting it with potassium iodide or copper (I) bromide in a solvent.

<Reaction 1)>
Nitrite salt: sodium nitrite, potassium nitrite, or the like.
Amount of nitrite salt: 1 to 2 moles per mole of compound [I-19]
Solvent: aqueous hydrogen bromide, aqueous sulfuric acid, or the like.
Temperature: −10° to 10° C.
Time: a moment to 5 hours
<Reaction 2)>
Amount of potassium iodide or copper (I) bromide: 1 mole to an excess per mole of compound [I-19]
Solvent: aqueous hydrogen bromide, aqueous sulfuric acid, or the like
Temperature: 0° to 80° C.
Time: a moment to 24 hours
(see Org. Syn. Coll., Vol. 2, 604 (1943), and ibid., Vol. 1, 136 (1941))

Process for Producing Compound [I-30] from Compound [I-29]

Compound [I-30] can be produced by reacting compound [I-29] with a compound of the formula:

$R^{13}$—OH  [13]

wherein $R^{13}$ is as defined above, in the presence of a transition metal catalyst and a base in a solvent under an atmosphere of carbon monoxide.
Catalyst: $PdCl_2(PPh_3)_2$ or the like
Amount of catalyst: a catalytic amount to 0.5 mole per mole of compound [I-29]
Amount of compound [13]: 1 mole to an excess per mole of compound [I-29]
Base: organic bases such as diethylamine
Amount of base: 1 to 10 moles per mole of compound [I-29]

Solvent: N,N-dimethylformamide or the like
Pressure of carbon monoxide: 1 to 150 atm.
Temperature: 0° to 100° C.
Time: a moment to 72 hours
(see Bull. Chem. Soc. Jpn., 48, 2075 (1975))

Production Process 9

This is the production process according to the following scheme:

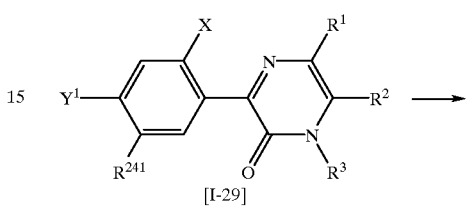
[I-29]

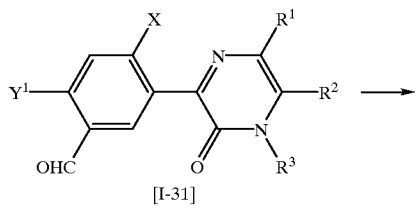
[I-31]

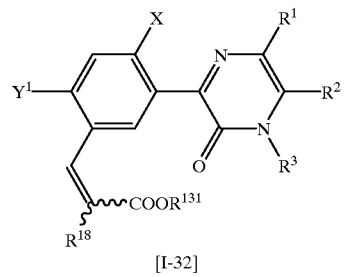
[I-32]

wherein $R^{131}$ is a substituent other than hydrogen, which is included in the definition of $R^{13}$; and X, $Y^1$, $R^1$, $R^2$, $R^3$, $R^{18}$, and $R^{241}$ are as defined above.

Process for Producing Compound [I-31] from Compound [I-29]

Compound [I-31] can be produced by reacting compound [I-29] with sodium formate or potassium formate in the presence of a transition metal catalyst in a solvent under an atmosphere of carbon monoxide.
Amount of sodium formate or potassium formate: 1 to 10 moles per mole of compound [I-29]
Solvent: N,N-dimethylformamide or the like
Catalyst: $PdCl_2(PPh_3)_2$ or the like
Amount of catalyst: a catalytic amount to 0.5 mole per mole of compound [I-29]
Pressure of carbon monoxide: 1 to 150 atm.
Temperature: 0° to 100° C.
Time: a moment to 72 hours
(see Bull. Chem. Soc. Jpn., 67, 2329 (1994))

Process for Producing Compound [I-32] from Compound [I-31]

Compound [I-32] can be produced by reacting compound [I-31] with a compound of the formula:

$(C_6H_5)_3P\!=\!CR^{18}COOR^{131}$  [14]

or $(C_2H_5O)_2P(O)CHR^{18}COOR^{131}$ [15]

wherein $R^{18}$ and $R^{131}$ are as defined above, in a solvent, and when compound [15] is used, in the presence of a base.

Amount of compound [14] or [15]: 1 to 5 moles per mole of compound [I-31]
Solvent: tetrahydrofuran, toluene, or the like
Base: sodium hydride or the like
Amount of base: 1 to 5 moles per mole of compound [I-31]
Temperature: 0° to 50° C.
Time: a moment to 24 hours Production Process 10

This is the production process according to the following scheme:

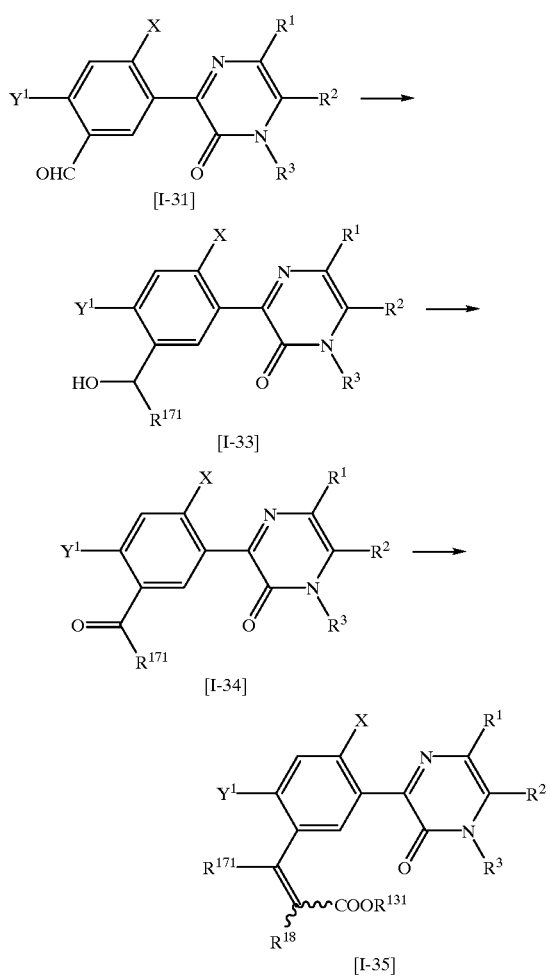

wherein $R^{171}$ is $C_1$–$C_6$ alkyl; and X, $Y^1$, $R^1$, $R^2$, $R^3$, $R^{18}$, and $R^{131}$ are as defined above.

Process for Producing Compound [I-33] from Compound [I-31]

Compound [I-33] can be produced by reacting compound [I-31] with a compound of the formula:

$R^{171}$—MgBr [16]

or $R^{171}$—Li [17]

wherein $R^{171}$ is as defined above, in a solvent.

Amount of compound [16] or [17]: 1 to 2 moles per mole of compound [I-31]
Solvent: ether solvents such as tetrahydrofuran
Temperature: −78° C. to room temperature
Time: a moment to 24 hours Process for producing compound [I-34] from compound [I-33]

Compound [I-34] can be produced by subjecting compound [I-33] to oxidative treatment such as chromic acid oxidation using chromic acid-sulfuric acid, pyridinium chlorochromate, or the like; oxidation using dimethylsulfoxide-acetic anhydride; or Swern oxidation.

Process for Producing Compound [I-35] from Compound [I-34]

Compound [I-35] can be produced by reacting compound [I-34] with a compound of the formula:

$(C_6H_5)_3P=CR^{18}COOR^{131}$ [14]

or $(C_2H_5O)_2P(O)CHR^{18}COOR^{131}$ [15]

wherein $R^{18}$ and $R^{131}$ are as defined above, in a solvent, and if compound [15] is used, in the presence of a base.

Amount of compound [14] or [15]: 1 to 5 moles per mole of compound [I-34]
Solvent: tetrahydrofuran, toluene, or the like
Base: sodium hydride or the like
Amount of base: 1 to 5 moles per mole of compound [I-34]
Temperature: 0° to 50° C.
Time: a moment to 24 hours Production Process 11

This is the production process according to the following scheme:

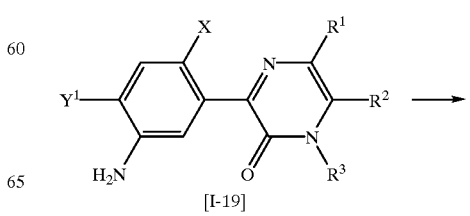

-continued

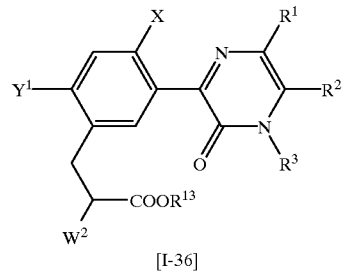
[I-36]

wherein $W^2$ is chlorine or bromine; and X, $Y^1$, $R^1$, $R^2$, $R^3$, and $R^{13}$ are as defined above.

Compound [I-36] can be produced by reacting compound [I-19] with t-butyl nitrite or t-amyl nitrite; a compound of the formula:

$$CuW^2_2 \qquad [18]$$

wherein $W^2$ is as defined above; and a compound of the formula:

$$CH_2=CHCOOR^{13} \qquad [19]$$

wherein $R^{13}$ is as defined above, in a solvent.

Amount of t-butyl nitrite or t-amyl nitrite: 1 to 2 moles per mole of compound [I-19]

Amount of compound [18]: 1 to 2 moles per mole of compound [I-19]

Amount of compound [19]: 10 moles to an excess per mole of compound [I-19]

Solvent: acetonitrile or the like

Temperature: 0° to 50° C.

Time: a moment to 24 hours (see EP 0 649 596, page 11)

Production Process 12

This is the production process according to the following scheme:

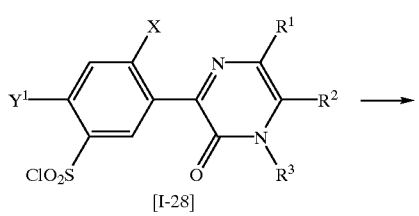

wherein X, $Y^1$, $R^1$, $R^2$, $R^3$, and $R^{10}$ are as defined above.

Compound [I-37] can be produced by reacting compound [I-28] with a compound of the formula:

$$R^{10}-OH \qquad [20]$$

wherein $R^{10}$ is as defined above, in the presence of a base without any solvent or in a solvent.

Amount of compound [20]: 1 mole to an excess per mole of compound [I-28]

Base: organic bases such as triethylamine; and inorganic bases such as potassium carbonate Amount of base: 1 mole to an excess per mole of compound [I-28]

Solvent: N,N-dimethylformamide, 1,4-dioxane, or the like

Temperature: 0° to 100° C.

Time: a moment to 24 hours

Production Process 13

This is the production process according to the following scheme:

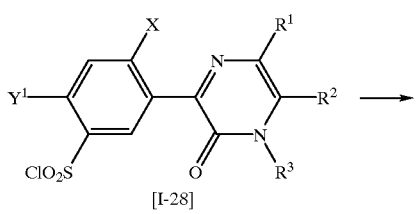

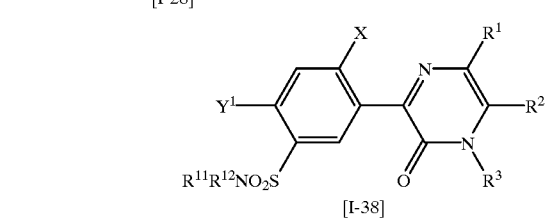

wherein X, $Y^1$, $R^1$, $R^2$, $R^3$, $R^{11}$, and $R^{12}$ are as defined above.

Compound [I-38] can be produced by reacting compound [I-28] with a compound of the formula:

$$R^{11}(R^{12})NH \qquad [21]$$

wherein $R^{11}$ and $R^{12}$ are as defined above, in the presence or absence of a base without any solvent or in a solvent.

Amount of compound [21]: 1 mole to an excess per mole of compound [I-28]

Base: organic bases such as triethylamine; and inorganic bases such as potassium carbonate Amount of base: 1 mole to an excess per mole of compound [I-28]

Solvent: N,N-dimethylformamide, 1,4-dioxane, or the like

Temperature: 0° to 100° C.

Time: a moment to 24 hours

Production Process 14

This is the production process according to the following scheme:

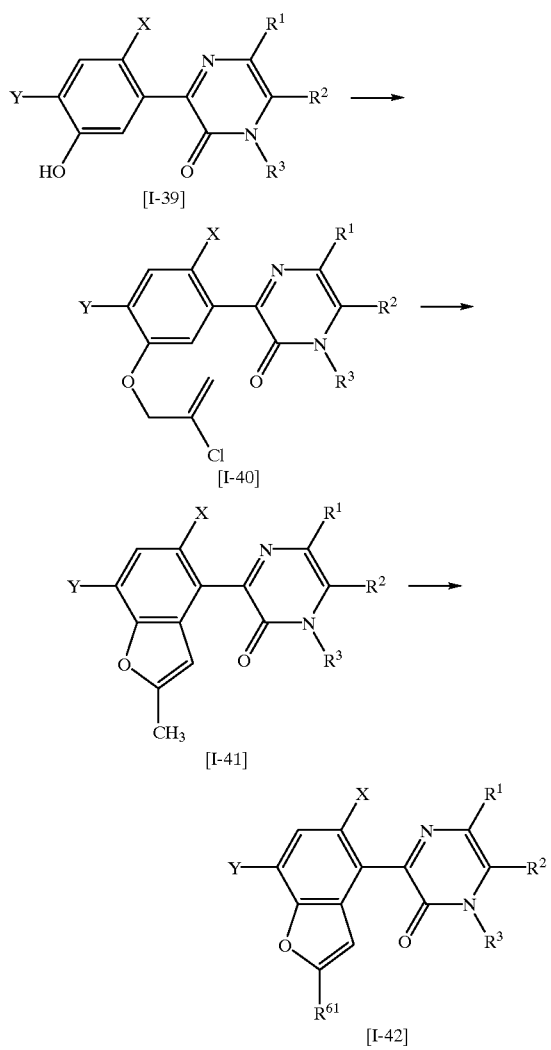

wherein $R^{61}$ is a substituent other than methyl, which is included in the definition of $R^6$; and X, Y, $R^1$, $R^2$, and $R^3$ are as defined above.

Process for Producing Compound [I-40] from Compound [I-39]

Compound [I-40] can be produced by reacting compound [I-39] with 2,3-dichloropropene in the presence of a base in a solvent.

Amount of 2,3-dichloropropene: 1 to 3 moles per mole of compound [I-39]
Base: inorganic bases such as potassium carbonate
Amount of base: 1 to 5 moles per mole of compound [I-39]
Solvent: N,N-dimethylformamide or the like
Temperature: 0° to 100° C.
Time: a moment to 24 hours

Process for Producing Compound [I-41] from Compound [I-40]

Compound [I-41] can be produced by heating compound [I-40] in a solvent.

Solvent: N,N-dimethylformamide, N,N-dimethylaniline, N,N-diethylaniline, p-diisopropylbenzene, or the like
Temperature: 70° to 200° C.
Time: a moment to 24 hours

Process for Producing Compound [I-42] from Compound [I-41]

Compound [I-42] can be produced from compound [I-41] according to the method in which the methyl group in position 2 on the benzofuran ring is replaced with another substituent, as described in U.S. Pat. No. 5,308,829, columns 2–11.

Production Process 15

This is the production process according to the following scheme:

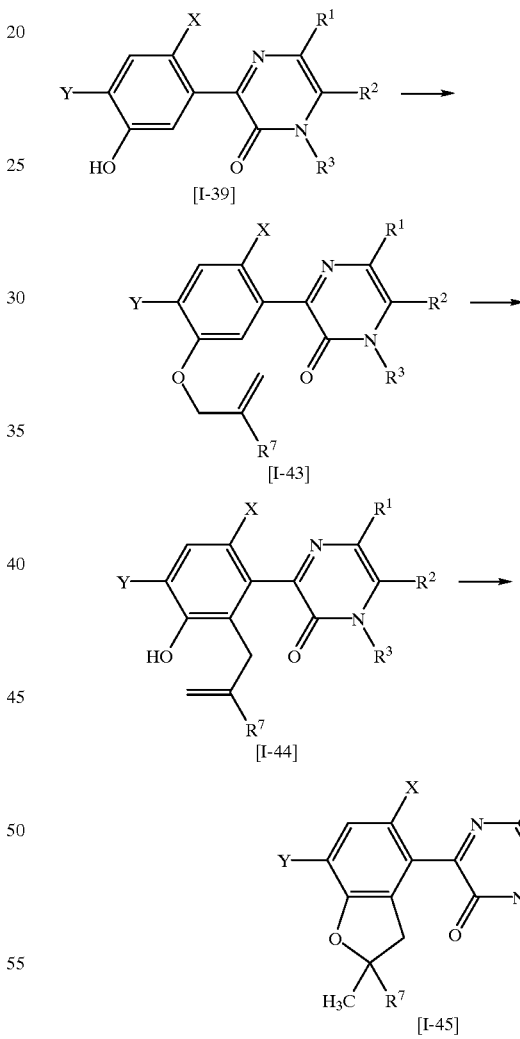

wherein X, Y, $R^1$, $R^2$, $R^3$, and $R^7$ are as defined above.

Process for Producing Compound [I-43] from Compound [I-39]

Compound [I-43] can be produced by reacting compound [I-39] with a compound of the formula:

$$CH_2=CR^7CH_2W^2 \qquad [22]$$

wherein W² and R⁷ are as defined above, in the presence of a base in a solvent.

Amount of compound [22]: 1 to 5 moles per mole of compound [I-39]
Base: inorganic bases such as potassium carbonate
Amount of base: 1 to 5 moles per mole of compound [I-39]
Solvent: N,N-dimethylformamide, 1,4-dioxane, or the like
Temperature: 0° to 100° C.
Time: a moment to 24 hours

Process for Producing Compound [I-44] from Compound [I-43]

Compound [I-44] can be produced by heating compound [I-43] in a solvent.

Solvent: N,N-dimethylaniline, N,N-diethylaniline, p-diisopropylbenzene, or the like
Temperature: 100° to 200° C.
Time: a moment to 24 hours

Process for Producing Compound [I-45] from Compound [I-44]

Compound [I-45] can be produced by heating compound [I-44] in the presence of an acid in a solvent.

Acid: organic acids such as p-toluenesulfonic acid; and inorganic acids such as sulfuric acid
Amount of acid: a catalytic amount to 1 mole per mole of compound [I-44]
Solvent: toluene, xylene, or the like
Temperature: 100° to 250° C.
Time: a moment to 24 hours

Production Process 16

This is the production process according to the following scheme:

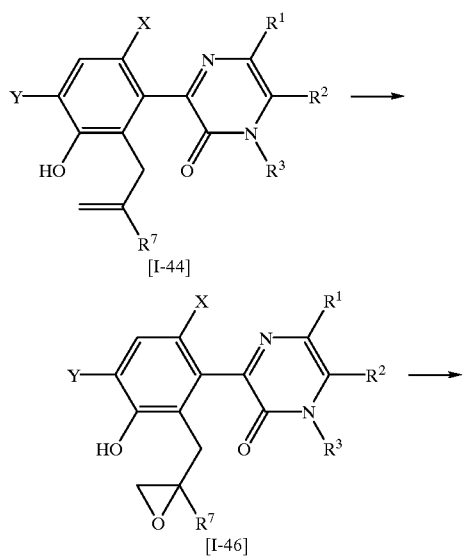

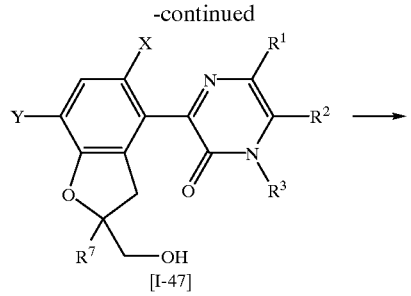

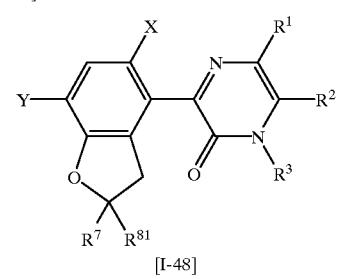

wherein R⁸¹ is a substituent other than methyl and hydroxymethyl, which is included in the definition of R⁸; and X, Y, R¹, R², R³, and R⁷ are as defined above.

Process for Producing Compound [I-46] from Compound [I-44]

Compound [I-46] can be produced by reacting compound [I-44] with a peracid in a solvent.

Peracid: m-chloroperbenzoic acid, peracetic acid, or the like
Amount of peracid: 1 mole to an excess per mole of compound [I-44]
Solvent: halogenated hydrocarbons such as dichloromethane; and organic acids such as acetic acid
Temperature: −20° C. to room temperature
Time: a moment to 24 hours

Process for Producing Compound [I-47] from Compound [I-46]

Compound [I-47] can be produced by reacting compound [I-46] in the presence of a base in a solvent.

Base: potassium carbonate or the like
Amount of base: 1 to 2 moles per mole of compound [I-46]
Solvent: methanol, ethanol, or the like
Temperature: 0° to 50° C.
Time: a moment to 5 hours

Process for Producing Compound [I-48] from Compound [I-47]

Compound [I-48] can be produced from compound [I-47] according to the method in which the hydroxyalkyl group in position 2 on the dihydrobenzofuran ring is replaced with another substituent, as described in U.S. Pat. No. 5,411,935, columns 5–10.

Production Process 17

This is the production process according to the following scheme:

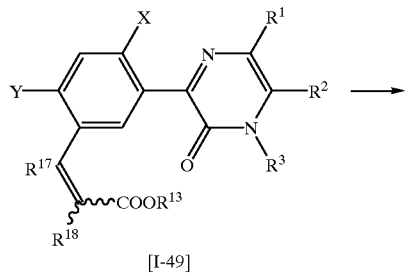

[I-49]

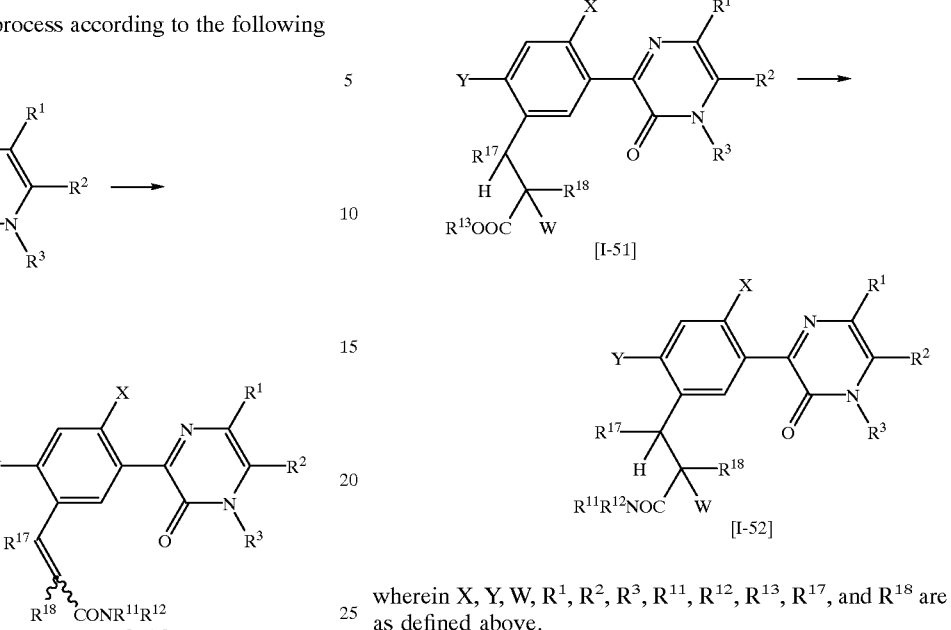

wherein X, Y, W, $R^1$, $R^2$, $R^3$, $R^{11}$, $R^{12}$, $R^{13}$, $R^{17}$, and $R^{18}$ are as defined above.

wherein X, Y, $R^1$, $R^2$, $R^3$, $R^{11}$, $R^{12}$, $R^{13}$, $R^{17}$, and $R^{18}$ are as defined above.

Compound [I-50] can be produced by reacting compound [I-49] with a compound of the formula:

$$R^{11}(R^{12})NH \quad [21]$$

wherein $R^{11}$ and $R^{12}$ are as defined above, in the presence or absence of a base without any solvent or in a solvent.

Amount of compound [21]: 1 mole to an excess per mole of compound [I-49]

Base: organic bases such as triethylamine; and inorganic bases such as potassium carbonate Amount of base: 1 mole to an excess per mole of compound [I-49]

Solvent: N,N-dimethylformamide, 1,4-dioxane, or the like

Temperature: 0° to 100° C.

Time: a moment to 24 hours

Process for Producing Compound [I-51] from Compound [I-49]

Compound [I-51] can be produced by reacting compound [I-49] with a compound of the formula:

$$HW \quad [23]$$

wherein W is as defined above, in the presence or absence of a catalyst without any solvent or in a solvent.

Amount of compound [23]: 1 mole to an excess per mole of compound [I-49]

Catalyst: aluminum chloride, aluminum bromide, or the like

Solvent: chloroform, acetic acid, or the like

Temperature: −20° to 120° C.

Time: a moment to 24 hours

Process for Producing Compound [I-52] from Compound [I-51]

Compound [I-52] can be produced by reacting compound [I-51] with a compound of the formula:

$$(R^{11})R^{12}NH \quad [21]$$

wherein $R^{11}$ and $R^{12}$ are as defined above, in the presence or absence of a base without any solvent or in a solvent.

Amount of compound [21]: 1 mole to an excess per mole of compound [I-51]

Base: organic bases such as triethylamine; and inorganic bases such as potassium carbonate Amount of base: 1 mole to an excess per mole of compound [I-51]

Solvent: N,N-dimethylformamide, 1,4-dioxane, or the like

Temperature: 0° to 100° C.

Time: a moment to 24 hours

Production Process 18

This is the production process according to the following scheme:

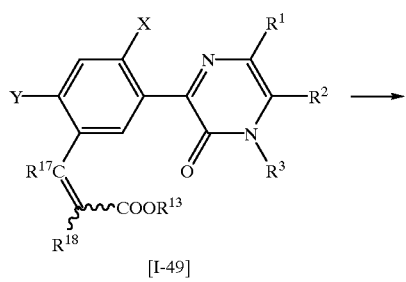

[I-49]

Compound [2], which is an intermediate compound for the production of the present compounds, can be produced by reacting a compound of the formula:

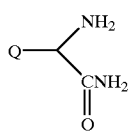

[24]

wherein Q is as defined above, with a compound of the formula:

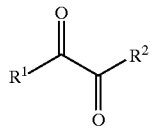

[25]

wherein $R^1$ and $R^2$ are as defined above.

The reaction is effected without any solvent or in a solvent. The reaction temperature is usually in the range of −20° to 150° C., preferably 0° to 60° C. The reaction time is usually in the range of a moment to 240 hours.

The amounts of the reagents to be used in the reaction, although the proportion of 1 mole of compound [25] to 1 mole of compound [24] is ideal, can be freely changed depending upon the reaction conditions.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, 1,2-dichloroethane, chlorobenzene, and dichlorobenzene; ethers such as diethyl ether, diisopropyl ether, dioxane, tetrahydrofuran, and ethylene glycol dimethyl ether; nitro compounds such as nitromethane and nitrobenzene; acid amides such as formamide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof.

After completion of the reaction, the reaction mixture is poured into water, if necessary, and subjected to ordinary post-treatments such as extraction with an organic solvent and concentration, or purified by a technique such as column chromatography or recrystallization. Thus the desired compound can be isolated.

The reaction conditions in the above step for the production of compound [2] are described in, for example, Journal of the American Chemical Society, 71, 78–81 (1949).

Among the examples of compound [2], those wherein $R^1$ is hydrogen can also be produced by reacting a compound of the formula:

[26]

wherein $R^2$ is as defined above and V is iodine, bromine, or chlorine, with water in the presence of a base to give a compound of the formula:

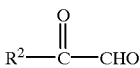

[27]

wherein $R^2$ is as defined above, or its hydrate (hereinafter referred to as reaction 1), and then reacting it with compound [24].

The reaction 1 is usually effected in a solvent. The reaction temperature is usually in the range of 20° to 100° C. The reaction time is usually in the range of a moment to 10 hours.

The amounts of the compounds to be used in the reaction, although the proportion of 2 moles of water and 2 moles of the base to 1 mole of compound [26] is ideal, can be freely changed depending upon the reaction conditions.

As the base, there can be used either organic bases or inorganic bases, examples of which include sodium acetate, potassium acetate, sodium carbonate, sodium hydrogencarbonate, and potassium carbonate.

Examples of the solvent which can be used include aliphatic hydrocarbons such as hexane, heptane, ligroin, cyclohexane, and petroleum ether; aromatic hydrocarbons such as benzene, toluene, and xylene; halogenated hydrocarbons such as chloroform, carbon tetrachloride, dichloromethane, 1,2-dichloroethane, chlorobenzene, and dichlorobenzene; ethers such as diethyl ether, diisopropyl ether, dioxane, tetrahydrofuran, and ethylene glycol dimethyl ether; esters such as ethyl formate, ethyl acetate, butyl acetate, and diethyl carbonate; nitro compounds such as nitromethane and nitrobenzene; nitriles such as acetonitrile and isobutyronitrile; acid amides such as formamnide, N,N-dimethylformamide, and acetamide; tertiary amines such as pyridine, triethylamine, diisopropylethylamine, N,N-dimethylaniline, N,N-diethylaniline, and N-methylmorpholine; sulfur compounds such as dimethylsulfoxide and sulforane; alcohols such as methanol, ethanol, ethylene glycol, and isopropanol; water; and mixtures thereof.

Compound [27] or its hydrate, which is formed by the above reaction, can be used without isolation or purification for the subsequent reaction with compound [24].

Compound [25] can be produced, for example, from the corresponding compound of the formula:

[28]

wherein $R^1$ and $R^2$ are as defined above, according to the method as described in Organic Synthesis Collective Volume, 2, 363 (1943) or Organic Synthesis Collective Volume, 3, 20 (1955).

Compound [28] can be produced from commercially available materials, for example, according to the method as described in Shin-Jikken Kagaku Koza 14, edited by the Chemical Society of Japan, Maruzen K. K., pp. 751–875.

Compound [26] can be obtained from various commercial sources or can be produced, for example, from the corresponding compound of the formula:

wherein $R^2$ is as defined above, according to the method as described in Journal of the American Chemical Society, 74, 3902 (1952).

Compound [24] can be produced according to the following scheme:

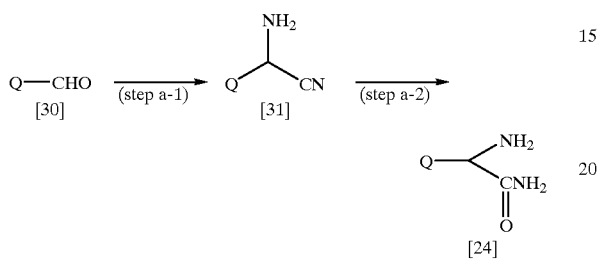

wherein Q is as defined above.

(Step a-1) can be conducted according to the method as described in Organic Synthesis Collective Volume, 1, 21 (1941); and (Step a-2), Journal of Organic Chemistry, 29, 1800 (1964).

Compound [30] can be obtained from various commercial sources or can be produced, for example, according to the following scheme:

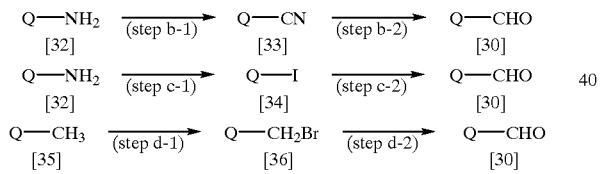

wherein Q is as defined above.

(Step b-1) can be conducted according to the method as described in Organic Synthesis Collective Volume, 1, 514 (1941);

(Step b-2), Jikken Kagaku Koza (4th ed.) 21, edited by the Chemical Society of Japan, Maruzen K. K., pp. 89–97;

(Step c-1), Organic Synthesis, 40, 105 (1960);

(Step c-2), Bulletin of the Chemical Society of Japan, 67, 2329 (1994);

(Step d-1), Synthesis, 1000 (1983); and (Step d-2), Journal of Organic Chemistry, 33, 3277 (1968).

Compound [32] is known in, or can be produced according to the method as described in, EP-61741-A; U.S. Pat. Nos. 4,670,046, 4,770,695, 4,709,049, 4,640,707, 4,720,927, 5,169,431; and JP-A 63-156787/1988.

Some examples of compound [32] can also be produced according to the following scheme:

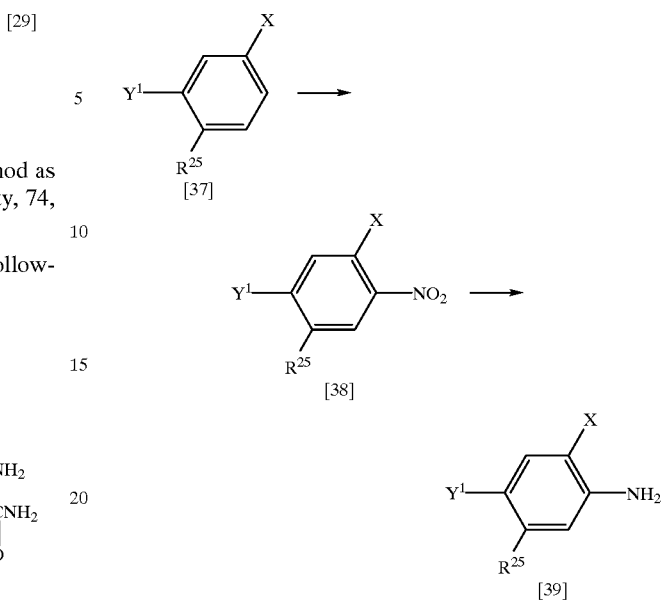

wherein $R^{25}$ is $-COR^{26}$ or $-COOR^{13}$; $R^{26}$ is hydrogen or $C_1$-$C_6$ alkyl; and X, $Y^1$, and $R^{13}$ are as defined above.

Process for Producing Compound [38] from Compound [37]

Compound [38] can be produced by reacting compound [37] with a nitrating agent in a solvent.

Nitrating agent: nitric acid or the like

Amount of nitrating agent: 1 to 10 moles per mole of compound [37]

Solvent: sulfuric acid or the like

Temperature: $-10°$ C. to room temperature

Time: a moment to 24 hours

Process for Producing Compound [39] from Compound [38]

Compound [39] can be produced by reducing compound [38] with iron powder or the like in the presence of an acid in a solvent.

Amount of iron powder or the like: 3 moles to an excess per mole of compound [38]

Acid: acetic acid or the like

Amount of acid: 1 to 10 moles per mole of compound [38]

Solvent: water, ethyl acetate, or the like

Temperature: room temperature to refluxing temperature under heating

Time: a moment to 24 hours

The present compounds have excellent herbicidal activity, and some of them exhibit excellent selectivity between crop plants and unfavorable weeds. In particular, the present compounds have herbicidal activity against various unfavorable weeds as recited below, which may cause trouble in the foliar treatment and soil treatment on upland fields.

Polygonaceae:

wild buckwheat (*Polygonum convolvulus*), pale smartweed (*Polygonum lapathifolium*), Pennsylvania smartweed (*Polygonum pensylvanicum*), ladysthumb (*Polygonum persicaria*), curly dock (*Rumex crispus*), broadleaf dock (*Rumex obtusifolius*), Japanese knotweed (*Polygonum cuspidatum*)

Portulacaceae:
  common purslane (*Portulaca oleracea*)
Caryophyllaceae:
  common chickweed (*Stellaria media*)
Chenopodiaceae:
  common lambsquarters (*Chenopodium album*), kochia (*Kochia scoparia*)
Amaranthaceae:
  redroot pigweed (*Amaranthus retroflexus*), smooth pigweed (*Amaranthus hybridus*)
Cruciferae:
  wild radish (*Raphanus raphanistrum*), wild mustard (*Sinapis arvensis*), shepherdspurse (*Capsella bursa-pastoris*)
Leguminosae:
  hemp sesbania (*Sesbania exaltata*), sicklepod (*Cassia obtusifolia*), Florida beggarweed (*Desmodium tortuosum*), white clover (*Trifolium repens*)
Malvaceae:
  velvetleaf (*Abutilon theophrasti*), prickly sida (*Sida spinosa*)
Violaceae:
  field pansy (*Viola arvensis*), wild pansy (*Viola tricolor*)
Rubiaceae:
  catchweed bedstraw (cleavers) (*Galium aparine*)
Convolvulaceae:
  ivyleaf morningglory (*Ipomoea hederacea*), tall morningglory (*Ipomoea purpurea*), entireleaf morningglory (*Ipomoea hederacea* var. *integriuscula*), pitted morningglory (*Ipomoea lacunosa*), field bindweed (*Convolvulus arvensis*)
Labiatae:
  red deadnettle (*Lamium purpureum*), henbit (*Lamium amplexicaule*)
Solanaceae:
  jimsonweed (*Datura stramonium*), black nightshade (*Solanum nigrum*)
Scrophulariaceae:
  birdseye speedwell (*Veronica persica*), ivyleaf speedwell (*Veronica hederaefolia*)
Compositae:
  common cocklebur (*Xanthium pensylvanicum*), common sunflower (*Helianthus annuus*), scentless chamomile (*Matricariaperforata* or *inodora*), corn marigold (*Chrysanthemum segetum*), pineappleweed (*Matricaria matricarioides*), common ragweed (*Ambrosia artemisiifolia*), giant ragweed (*Ambrosia trifida*), horseweed (*Erigeron canadensis*), Japanese mugwort (*Artemisia princeps*), tall goldenrod (*Solidago altissima*)
Boraginaceae:
  field forget-me-not (*Myosotis arvensis*)
Asclepiadaceae:
  common milkweed (*Asclepias syriaca*)
Euphorbiaceae:
  sun spurge (*Euphorbia helioscopia*), spotted spurge (*Euphorbia maculata*)
Gramineae:
  barnyardgrass (*Echinochloa crus-galli*), green foxtail (*Setaria viridis*), giant foxtail (*Setaria faberi*), large crabgrass (*Digitaria sanguinalis*), goosegrass (*Eleusine indica*), annual bluegrass (*Poa annua*), blackgrass (*Alopecurus myosuroides*), wild oat (*Avena fatua*), johnsongrass (*Sorghum halepense*), quackgrass (*Agropyron repens*), downy brome (*Bromus tectorum*), bermudagrass (*Cynodon dactylon*), fall panicum (*Panicum dichotomiflorum*), Texas panicum (*Panicum texanum*), shattercane (*Sorghum vulgare*)
Commelinaceae:
  common dayflower (*Commelina communis*)
Equisetaceae:
  field horsetail (*Equisetum arvense*)
Cyperaceae:
  rice flatsedge (*Cyperus iria*), purple nutsedge (*Cyperus rotundus*), yellow nutsedge (*Cyperus esculentus*)

Furthermore, some of the present compounds have no problematic phytotoxicity on main crops such as corn (*Zea mays*), wheat (*Triticum aestivum*), barley (*Hordeum vulgare*), rice (*Oryza saliva*), sorghum (*Sorghum bicolor*), soybean (*Glycine max*), cotton (Gossypium spp.), sugar beet (*Beta vulgaris*), peanut (*Arachis hypogaea*), sunflower (*Helianthus annuus*) and canola (*Brassica napus*); garden crops such as flowers and ornamental plants; and vegetable crops.

The present compounds can attain effective control of unfavorable weeds in the no-tillage cultivation of soybean (*Glycine max*), corn (*Zea mays*), and wheat (*Triticum aestivum*). Furthermore, some of them exhibit no problematic phytotoxicity on crop plants.

The present compounds have herbicidal activity against various unfavorable weeds as recited below under the flooding treatment on paddy fields.
Gramineae:
  barnyardgrass (*Echinochloa oryzicola*)
Scrophulariaceae:
  common falsepimpernel (*Lindernia procumbens*)
Lythraceae:
  *Rotala indica, Ammannia multiflora*
Elatinaceae:
  *Elatine triandra*
Cyperaceae:
  smallflower umbrellaplant (*Cyperus difformis*), hardstem bulrush (*Scirpus juncoides*), needle spikerush (*Eleocharis acicularis*), *Cyperus serotinus, Eleocharis kuroguwai*
Pontederiaceae:
  *Monochoria vaginalis*
Alismataceae:
  *Sagittaria pygmaea, Sagittaria trifolia, Alisma canaliculatum*
Potamogetonaceae:
  roundleaf pondweed (*Potamogeton distinctus*)
Umbelliferae:
  *Oenanthe javanica*

Furthermore, some of the present compounds have no problematic phytotoxicity on transplanted paddy rice.

The present compounds can attain effective control of various unfavorable weeds in orchards, grasslands, lawns, forests, waterways, canals, or other non-cultivated lands.

The present compounds also have herbicidal activity against various aquatic plants such as water hyacinth (*Eichhornia crassipes*), which will grow in waterways, canals, or the like.

The present compounds have substantially the same characteristics as those of the herbicidal compounds described in the publication of International Patent Application, W095/34659. In the case where crop plants with tolerance imparted by introducing a herbicide tolerance gene described in the publication are cultivated, the present compounds can be used at greater doses than those used when ordinary crop plants without tolerance are cultivated, and it is, therefore, possible to attain effective control of other unfavorable plants.

When the present compounds are used as active ingredients of herbicides, they are usually mixed with solid or liquid carriers or diluents, surfactants, and other auxiliary agents to give formulations such as emulsifiable concentrates, wettable powders, flowables, granules, concentrated emulsions, and water-dispersible granules.

These formulations may contain any of the present compounds as an active ingredient at an amount of 0.001% to 80% by weight, preferably 0.003% to 70% by weight, based on the total weight of the formulation.

Examples of the solid carrier or diluent may include fine powders or granules of the following materials: mineral matters such as kaolin clay, attapulgite clay, bentonite, terra alba, pyrophyllite, talc, diatomaceous earth, and calcite; organic substances such as walnut shell powder; water-soluble organic substances such as urea; inorganic salts such as ammonium sulfate; and synthetic hydrated silicon oxide. Examples of the liquid carrier or diluent may include aromatic hydrocarbons such as methylnaphthalene, phenylxylylethane, and alkylbenzenes (e.g., xylene); alcohols such as isopropanol, ethylene glycol, and 2-ethoxyethanol; esters such as phthalic acid dialkyl esters; ketones such as acetone, cyclohexanone, and isophorone; mineral oils such as machine oil; vegetable oils such as soybean oil and cotton seed oil; dimethylsulfoxide, N,N-dimethylformamide, acetonitrile, N-methylpyrrolidone, water, and the like.

Examples of the surfactant used for emulsification, dispersing, or spreading may include surfactants of the anionic type, such as alkylsulfates, alkylsulfonates, alkylarylsulfonates, dialkylsulfosuccinates, and phosphates of polyoxyethylene alkyl aryl ethers; and surfactants of the nonionic type, such as polyoxyethylene alkyl ethers, polyoxyethylene alkyl aryl ethers, polyoxyethylene polyoxypropylene block copolymers, sorbitan fatty acid esters, and polyoxyethylene sorbitan fatty acid esters.

Examples of the auxiliary agent used for formulation may include ligninsulfonates, alginates, polyvinyl alcohol, gum arabic, carboxymethyl cellulose (CMC), and isopropyl acid phosphate (PAP).

The present compounds are usually formulated as described above and then used for the pre- or post-emergence soil, foliar, or flooding treatment of unfavorable weeds. The soil treatment may include soil surface treatment and soil incorporation. The foliar treatment may include application over the plants and directed application in which a chemical is applied only to the unfavorable weeds so as to keep off the crop plants.

The present compounds can be used, if necessary, in combination with other compounds having herbicidal activity. Examples of the compounds which can be used in combination with the present compounds may include various compounds described in Catalog 1995 Edition of Farm Chemicals Handbook (Meister Publishing Company); AG CHEM NEW COMPOUND REVIEW, VOL. 13, 1995 (AG CHEM INFORMATION SERVICE); JOSOUZAI KENKYU SOURAN (Hakuyu-sha); or HERBICIDE HANDBOOK, Seven Edition (Weed Science Society of America). Typical examples of such compounds are as follows: atrazin, cyanazine, metribuzin, prometryn, simazine, chlorotoluron, diuron, dymrone, fluometuron, isoproturon, methabenzthiazuron, bromoxynil, ioxynil, pendimethalin, trifluralin, acifluorfen, acifluorfen-sodium, chlomethoxynil, fomesafen, lactofen, oxyfluorfen, carfentrazone, flumiclorac-pentyl, flumioxazine, fluthiacetmethyl, sulfentrazone, diquat, paraquat, 2,4-D, 2,4-DB, DCPA, MCPA, MCPB, clomeprop, clopyralid, dicamba, dithiopyr, fluroxypyr, mecoprop, naproanilide, quinclorac, triclopyr, acetochlor, alachlor, diethatyl-ethyl, metolachlor, pretilachlor, bensulfuron-methyl, chlorsulfuron, chlorimuron-ethyl, halosulfuron-methyl, metsulfuron-methyl, nicosulfuron, primisulfuron, pyrazosulfuron-ethyl, sulfometuron-methyl, thifensulfuron-methyl, triasulfuron, tribenuron-methyl, azimsulfuron, cloransulam-methyl, cyclosulfamuron, flumetsulam, flupyrsulfuron, flazasulfuron, imazosulfuron, metosulam, prosulfuron, rimsulfuron, triflusulfuron-methyl, imazapyr, imazaquin, imazethapyr, imazamox, bispyribac-sodium, pyrithiobac-sodium, clethodim, sethoxydim, tralkoxydim, diclofop-methyl, fenoxaprop-ethyl, fenoxaprop-p-ethyl, fluazifop-butyl, fluazifop-p-butyl, haloxyfop-methyl, quizalofop-p-ethyl, cyhalofop-butyl, clodinafop-propargyl, clomazone, diflufenican, norflurazon, pyrazolate, pyrazoxyfen, isoxaflutole, sulcotrione, glufosinate-ammonium, glyphosate, bentazon, bromobutide, butamifos, dimepiperate, dimethenamid, DSMA, mefenacet, molinate, MSMA, pyributicarb, propanil, pyridate, triallate, cafenstrol, and thiafluamide.

The present compounds may also be used in admixture with insecticides, acaricides, nematocides, fungicides, plant growth regulators, fertilizers, soil improvers, and the like.

When the present compounds are used as active ingredients of herbicides, the application amount is usually in the range of 0.01 to 10,000 g, preferably 0.5 to 8000 g, per hectare, although it may vary depending upon the weather conditions, formulation type, application timing, application method, soil conditions, crop plants, unfavorable weeds, and the like. In the case of emulsifiable concentrates, wettable powders, flowables, concentrated emulsions, water-dispersible granules, or the like, the formulation is usually applied at a prescribed amount after diluted with water having a volume of about 10 to 1000 liters per hectare, if necessary, with the addition of an adjuvant such as a spreading agent. In the case of granules or some types of flowables, the formulation is usually applied as such without any dilution.

Examples of the adjuvant used, if necessary, may include, in addition to the surfactants recited above, polyoxyethylene resin acids (esters), ligninsulfonates, abietates, dinaphthylmethanedisulfonates, silicone polymers, crop oil concentrates, and vegetable oils such as soybean oil, corn oil, cotton seed oil, and sunflower oil.

The present compounds can also be used as active ingredients of harvesting aids such as defoliants and desiccating agents for cotton (Gossypium spp.), and desiccating agents for potato (*Solanum tuberosum*). In these cases, the present compounds are usually formulated in the same manner as the case where they are used as active ingredients of herbicides, and used alone or in combination with other harvesting aids for foliar treatment before the harvesting of crops.

The present invention will be further illustrated by the following production examples, formulation examples, and test examples; however, the present invention is not limited to these examples.

The following will describe production examples for the present compounds, where the present compounds are designated by their compound numbers shown in Tables 1 to 5 and some of the starting compounds are designated by their compound numbers shown in Tables 6 to 8.

PRODUCTION EXAMPLE 1

(1) First, 23.3 g of 3-(2,4-difluorophenyl)-6-trifluoromethyl-2-oxo-1,2-dihydropyrazine (compound 1-1004) was dissolved in 150 ml of acetone, to which 17.5 g of potassium carbonate and 14.3 g of methyl iodide were added, and the mixture was stirred at room temperature for 15 hours. After completion of the reaction, most of the acetone was distilled out under reduced pressure, and the residue was poured into water, followed by extraction with ethyl acetate. The organic layer was washed with saturated sodium chloride solution, dried with anhydrous magnesium sulfate, and concentrated. The residue was subjected to silica gel column chromatography (eluent, hexane/ethyl acetate= 19:1), which afforded 16.1 g of 3-(2,4-difluorophenyl)-2-methoxy-6-trifluoromethylpyrazine (m.p., 55.3° C.) as the earlier eluted O-methylated compound and 7.13 g (yield, 29%) of 3-(2,4-difluorophenyl)-1-methyl-6-trifluoromethyl-2-oxo-1,2-dihydropyrazine (present compound 1-10; m.p., 73.0° C.) as the later eluted desired compound.

(2) To 85 ml of concentrated sulfuric acid was added 7.0 g of 3-(2,4-difluorophenyl)-1-methyl-6-trifluoromethyl-2-oxo-1,2-dihydropyrazine (present compound 1-10) at 5° C. Furthermore, 9 ml of 70% nitric acid was added, and the mixture was stirred at 5° to 10° C. for 8 hours. After completion of the reaction, the reaction mixture was added to ice water, followed by extraction with ethyl acetate. The organic layer was washed with water and then saturated sodium chloride solution, dried with anhydrous magnesium sulfate, and concentrated. The residue was subjected to silica gel column chromatography, which afforded 7.76 g (yield, 96%) of 3-(2,4-difluoro-5-nitrophenyl)-1-methyl-6-trifluoromethyl-2-oxo-1,2-dihydropyrazine (present compound 1-16; m.p., 93.2° C.).

(3) Then, 7.61 g of 3-(2,4-difluoro-5-nitrophenyl)-1-methyl-6-trifluoromethyl-2-oxo-1,2-dihydropyrazine (present compound 1-16) was dissolved in 10 ml of 1,4-dioxane, to which 5.28 g of potassium fluoride and 9.0 g of butyl glycolate were added, and the mixture was heated under reflux for 1.5 hours. After completion of the reaction, the reaction mixture was left cooling to room temperature. The reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 8.37 g (yield, 82%) of 3-[4-(butoxycarbonylmethoxy)-2-fluoro5-nitrophenyl]-1-methyl-6-trifluoromethyl-2-oxo-1,2-dihydropyrazine (the present compound depicted below; m.p., 109.5° C.).

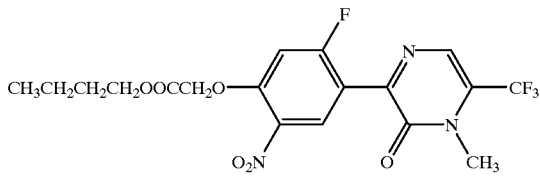

(4) Then, 2.8 g of iron powder was added to a mixture of 5 ml of acetic acid and 50 ml of water, and the mixture was heated to 50° C. To this was slowly added dropwise a solution of 2.8 g of 3-[4-(butoxycarbonylmethoxy)-2-fluoro-5-nitrophenyl]-1-methyl-6-trifluoromethyl-2-oxo-1,2-dihydropyrazine (the present compound obtained in step (3) above) in 25 ml of ethyl acetate and 25 ml of acetic acid. The mixture was stirred at an internal temperature of 60° to 70° C. for 1 hour. After completion of the reaction, the reaction mixture was poured into ice water, followed by extraction with ethyl acetate. The organic layer was washed with saturated sodium hydrogencarbonate solution, water, and saturated sodium chloride solution, dried with anhydrous magnesium sulfate, and concentrated, which afforded 1.22 g of 3-(7-fluoro-3-oxo-2H-1,4-benzoxazin-6-yl)-1-methyl-6-trifluoromethyl-2-oxo-1,2-dihydropyrazine (present compound 2-49; m.p., 182.5° C.).

(5) Then, 1.22 g of 3-(7-fluoro-3-oxo-2H-1,4-benzoxazin-6-yl)-1-methyl-6-trifluoromethyl-2-oxo-1,2-dihydropyrazine (present compound 2-49) was dissolved in 15 ml of N,N-dimethylformamide, to which 0.59 g of potassium carbonate and 0.47 g of propargyl bromide were added, and the mixture was stirred at room temperature for 3 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 0.60 g (total yield in two steps (4) and (5), 25%) of 3-(7-fluoro-3-oxo-4-propargyl-2H-1,4-benzoxazin-6-yl)-1-methyl-6-trifluoromethyl-2-oxo-1,2-dihydropyrazine (present compound 2-61; m.p., 141.4° C.).

PRODUCTION EXAMPLE 2

(1) First, 3.61 g of 3-(4-chloro-2-fluoro-5-methoxyphenyl)-6-trifluoromethyl-2-oxo-1,2-dihydropyrazine (compound 1-1008) was dissolved in 16 ml of N,N-dimethylformamide, to which 2.35 g of potassium carbonate and 1.39 ml of methyl iodide were added, and the mixture was stirred at 100° C. for 2 days. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography (eluent, hexane/ethyl acetate=5:1), which afforded 2.04 g (yield, 55%) of 3-(4-chloro-2-fluoro-5-methoxyphenyl)-1-methyl-6-trifluoromethyl-2-oxo-1,2-dihydropyrazine (present compound 1-144; m.p., 108.7° C.).

(2) A mixture of 2.04 g of 3-(4-chloro-2-fluoro-5-methoxyphenyl)- 1-methyl-6-trifluoromethyl-2-oxo-1,2-dihydropyrazine (present compound 1-144) and 35 ml of 48% hydrobromic acid was dissolved in 12 ml of acetic acid, and the solution was stirred at 140° C. for 1 hour. After completion of the reaction, the reaction mixture was poured into water, followed by extraction with ethyl acetate. The organic layer was washed with saturated sodium hydrogencarbonate solution, water, and then saturated sodium chloride solution, dried with anhydrous magnesium sulfate, and concentrated. The residue was subjected to silica gel column chromatography, which afforded 1.55 g (yield, 79%) of 3-(4-chloro-2-fluoro-5-hydroxyphenyl)-1-methyl-6-trifluoromethyl-2-oxo-1,2-dihydropyrazine (present compound 1-61; m.p., 188.1° C.).

(3) Then, 0.148 g of 3-(4-chloro-2-fluoro-5-hydroxyphenyl)-1-methyl-6-trifluoromethyl-2-oxo-1,2-dihydropyrazine (present compound 1-61) was dissolved in 0.90 ml of N,N-dimethylformamide, to which 0.097 g of potassium carbonate and 57 µl of methyl 2-bromopropionate were added, and the mixture was stirred at room temperature for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 0.180 g (yield, 96%) of 3-(4-chloro-2-fluoro-5-(1-methoxycarbonylethoxy) phenyl)-1methyl-6-trifluoromethyl-2-oxo-1,2-dihydropyrazine (present compound 1-173).

$^1$H-NMR (CDCl$_3$/TMS, 250 MHz, δ (ppm)) 1.68 (d, 3H, J=6.8 Hz), 3.67 (s, 3H), 3.6 (s, 3H), 4.76 (q, 1H, J=6.8 Hz), 7.2–7.3 (m, 2H), 7.83 (s, 1H)

PRODUCTION EXAMPLE 3

According to the procedure in step (3) of Production Example 2, 0.184 g (yield, 95%) of 3-(4-chloro-2-fluoro-5-(1-ethoxycarbonylethoxy)phenyl)-1-methyl-6-trifluoromethyl-2-oxo-1,2-dihydropyrazine (present compound 1-174) was obtained using 0.150 g of 3-(4-chloro-2-fluoro-5-hydroxyphenyl)-1-methyl-6-trifluoromethyl-2-oxo-1,2-dihydropyrazine (present compound 1-61), 0.90 ml of N,N-dimethylformamide, 0.097 g of potassium carbonate, and 73 μl of ethyl 2-bromopropionate.

$^1$H-NMR (CDCl$_3$/TMS, 300 MHz, δ (ppm)) 1.26 (t, 3H, J=7.1 Hz), 1.67 (d, 3H, J=6.9 Hz), 3.67 (s, 3H), 4.22 (q, 2H, J=7.1 Hz), 4.76 (q, 1H, J=6.9 Hz), 7.2–7.3 (m, 2H), 7.82 (s, 1H)

PRODUCTION EXAMPLE 4

(1) First, 0.659 g of 3-(4-fluorophenyl)-6-trifluoromethyl-2-oxo-1,2-dihydropyrazine (compound 1-1001) was dissolved in 3.8 ml of N,N-dimethylformamide, to which 0.529 g of potassium carbonate and 0.32 ml of methyl iodide were added, and the mixture was stirred at 100° C. for 1.5 days. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography (eluent, hexane/ethyl acetate=8:1), which afforded 0.480 g (yield, 69%) of 3-(4-fluorophenyl)-1-methyl-6-trifluoromethyl-2-oxo-1,2-dihydropyrazine (present compound 1-4; m.p., 121.1° C.).

(2) To 2.5 ml of concentrated sulfuric acid was added 0.34 g of 3-(4-fluorophenyl)-1-methyl-6-trifluoromethyl-2-oxo-1,2-dihydropyrazine (present compound 1-4) at 5° C. Furthermore, 0.13 ml of 61% nitric acid was added, and the mixture was stirred at room temperature for 1 hour. After completion of the reaction, the reaction mixture was added to ice water, followed by extraction with ethyl acetate. The organic layer was washed with water and then saturated sodium chloride solution, dried with anhydrous magnesium sulfate, and concentrated. The residue was subjected to silica gel column chromatography, which afforded 0.337 g (yield, 85%) of 3-(4-fluoro-5-nitrophenyl)-1-methyl-6-trifluoromethyl-2-oxo-1,2-dihydropyrazine (present compound 1-13; m.p., 134.4° C.).

(3) Then, 1.10 g of 3-(4-fluoro-5-nitrophenyl)-1-methyl-6-trifluoromethyl-2-oxo-1,2-dihydropyrazine (present compound 1-13) was dissolved in 4.0 ml of 1,4-dioxane, to which 0.812 g of potassium fluoride and 0.925 g of butyl glycolate, and the mixture was heated under reflux for 1.5 hours. After completion of the reaction, the reaction mixture was left cooling to room temperature. The reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 1.25 g (yield, 83%) of 3-[4-(butoxycarbonylmethoxy)-5-nitrophenyl]-1-methyl-6-trifluoromethyl-2-oxo-1,2-dihydropyrazine (the present compound depicted below).

$^1$H-NMR (CDCl$_3$/TMS, 300 MHz, δ (ppm)) 0.8–1.0 (m, 3H), 1.2–1.4 (m, 2H), 1.6–1.8 (m, 2H), 3.69 (s, 3H), 4.2–4.3 (m, 2H), 4.85 (s, 2H), 7.02 (d, 1H, J=9.0 Hz), 7.85 (s, 1H), 8.73 (dd, 1H, J=9.0 Hz, 2.3 Hz), 9.08 (d, 1H, J=2.3 Hz)

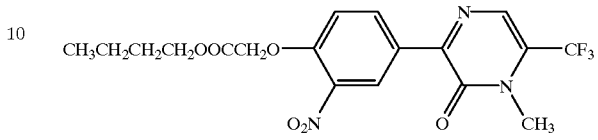

(4) Then, 0.24 g of 10% palladium/carbon was added to a solution of 1.25 g of 3-[4-(butoxycarbonylmethoxy)-5-nitrophenyl]-1-methyl-6-trifluoromethyl-2-oxo-1,2-dihydropyrazine in 36 ml of ethyl acetate under an atmosphere of nitrogen, which was then replaced with hydrogen under a pressure of 1 atm., and the mixture was stirred at room temperature for 2 hours. After completion of the reaction, the reaction mixture was filtered through celite and concentrated. To the crude product obtained was added 2.0 ml of acetic acid, and the mixture was stirred at room temperature for 1 hour. After completion of the reaction, the reaction mixture was poured into water, followed by extraction with ethyl acetate. The organic layer was washed with saturated sodium hydrogencarbonate solution, water, and then saturated sodium chloride solution, dried with anhydrous magnesium sulfate, and concentrated. The residue was subjected to silica gel column chromatography, which afforded 0.45 g (yield, 48%) of 3-(3-oxo-2H-1,4-benzoxazin-6-yl)-1-methyl-6-trifluoromethyl-2-oxo-1,2-dihydropyrazine (present compound 2-1; m.p., 191.1° C.).

(5) Then, 0.15 g of 3-(3-oxo-2H-1,4-benzoxazin-6-yl)-1-methyl-6-trifluoromethyl-2-oxo-1,2-dihydropyrazine (present compound 2-1) was dissolved in 0.92 ml of N,N-dimethylformamide, to which 0.127 g of potassium carbonate and 70 μl of propargyl bromide were added, and the mixture was stirred at 60° C. for 2 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 0.12 g (yield, 74%) of 3-(3-oxo-4-propargyl-2H-1,4-benzoxazin-6-yl)-1-methyl-6-trifluoromethyl-2-oxo-1,2-dihydropyrazine (present compound 2-13; m.p., 129.2° C.).

PRODUCTION EXAMPLE 5

(1) First, 2.93 g of 3-(4-chloro-2-fluorophenyl)-6-trifluoromethyl-2-oxo-1,2-dihydropyrazine (compound 1-1005) was dissolved in 15 ml of N,N-dimethylformamide, to which 2.07 g of potassium carbonate and 1.25 ml of methyl iodide were added, and the mixture was stirred at 100° C. for 2 days. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography (eluent, hexane/ethyl acetate=6:1), which afforded 1.98 g (yield, 65%) of 3-(4-chloro-2-fluorophenyl)-1-methyl-6-trifluoromethyl-2-oxo-1,2-dihydropyrazine (present compound 1-11; m.p., 83.2° C.).

(2) To 3.3 ml of concentrated sulfuric acid was added 0.50 g of 3-(4chloro-2-fluorophenyl)-1-methyl-6-trifluoromethyl-2-oxo-1,2-dihydropyrazine (present compound 1-11) at 5° C. Furthermore, 0.17 ml of 61% nitric acid was added, and the mixture was stirred at room temperature for 1 hour. After completion of the reaction, the reaction mixture was added to ice water, followed by extraction with ethyl acetate. The organic layer was washed with water and then saturated sodium chloride solution, dried with anhydrous magnesium sulfate, and concentrated. The residue was subjected to silica gel column chromatography, which afforded 0.55 g (yield, 95%) of 3-(4-chloro-2-fluoro-5-nitrophenyl)- 1-methyl-6-trifluoromethyl-2-oxo-1,2-dihydropyrazine (present compound 1-17; m.p., 98.3° C.).

(3) Then, 0.37 g of iron powder was added to a mixture of 5.3 ml of acetic acid and 2.0 ml of water, to which a solution of 0.39 g of 3-(4-chloro-2-fluoro-5-nitrophenyl)-1-methyl-6-trifluoromethyl-2-oxo-1,2-dihydropyrazine (present compound 1-17) in 1.0 ml of acetic acid was slowly added dropwise, and the mixture was stirred at room temperature for 3.5 hours. After completion of the reaction, the reaction mixture was poured into water, followed by extraction with ethyl acetate. The organic layer was washed twice with water and further with saturated sodium chloride solution, dried with anhydrous magnesium sulfate, and concentrated, which afforded 0.16 g (yield, 46%) of 3-(5-amino-4-chloro-2-fluorophenyl)-1-methyl-6-trifluoromethyl-2-oxo-1,2-dihydropyrazine (present compound 1-23).

$^1$H-NMR (CDCl$_3$/TMS, 300 MHz, δ (ppm)) 3.66 (s, 3H), 4.1–4.5 (br, 2H), 7.01 (d, 1H, J=6.4 Hz), 7.11 (d, 1H, J=9.5 Hz), 7.82 (s, 1H)

(4) Then, 0.10 g of 3-(5-amino-4-chloro-2-fluorophenyl)-1-methyl-6-trifluoromethyl-2-oxo-1,2-dihydropyrazine (present compound 1-23) was dissolved in 0.62 ml of pyridine, to which 36 μl of methanesulfonyl chloride was added dropwise, and the mixture was stirred at room temperature for 5 hours. After completion of the reaction, the reaction mixture was poured into water, followed by extraction with chloroform. The organic layer was washed with 2N hydrochloric acid, water, saturated sodium hydrogencarbonate solution, and then saturated sodium chloride solution, dried with anhydrous magnesium sulfate, and concentrated. The residue was subjected to silica gel column chromatography, which afforded 91 mg (yield, 73%) of 3-[4-chloro-2-fluoro-5-(methanesulfonylamino)phenyl]-1-methyl-6-trifluoromethyl-2-oxo-1,2-dihydropyrazine (present compound 1-37; m.p., 168.5° C.).

PRODUCTION EXAMPLE 6

A mixture of 0.12 g of 3-(5-amino-4-chloro-2-fluorophenyl)-1-methyl-6-trifluoromethyl-2-oxo-1,2-dihydropyrazine (present compound 1-23) and 70 μl of ethyl 2-bromopropionate was stirred at 140° C. for 3 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 80 mg (yield, 51%) of 3-{4-chloro-5-[1-(ethoxycarbonyl)ethylamino]-2-fluorophenyl}-1-methyl-6-trifluoromethyl-2-oxo-1,2-dihydropyrazine (present compound 1-90).

$^1$H-NMR (CDCl$_3$/TMS, 300 MHz, δ (ppm)) 1.26 (t, 3H, J=7.1 Hz), 1.52 (d, 3H, J=6.8 Hz), 3.67 (s, 3H), 4.1–4.3 (m, 3H), 4.7–4.8 (br, 1H), 6.83 (d, 1H, J=6.2 Hz), 7.17 (d, 1H, J=9.6 Hz), 7.81 (s, 1H)

PRODUCTION EXAMPLE 7

(1) First, 79 mg of 10% palladium/carbon was added to a solution of 0.30 g of 3-(4-fluoro-5-nitrophenyl)-1-methyl-6-trifluoromethyl-2-oxo-1,2-dihydropyrazine (present compound 1-13) in 12 ml of ethyl acetate under an atmosphere of nitrogen, which was then replaced with hydrogen under a pressure of 1 atm., and the mixture was stirred at room temperature for 3 hours. After completion of the reaction, the reaction mixture was filtered through celite and concentrated. The residue was subjected to silica gel column chromatography, which afforded 0.13 g (yield, 47%) of 3-(5-amino-4-fluorophenyl)-1-methyl-6-trifluoromethyl-2-oxo-1,2-dihydropyrazine (present compound 1-19).

$^1$H-NMR (CDCl$_3$/TMS, 250 MHz, δ (ppm)) 3.66 (s, 3H), 3.7–3.9 (br, 2H), 7.05 (dd, 1H, J=10.7 Hz, 8.7 Hz), 7.80 (s, 1H), 7.7–7.9 (m, 1H), 7.89 (dd, 1H, J=8.9, 2.2 Hz)

(2) A mixture of 0.12 g of 3-(5-amino-4-fluorophenyl)-1-methyl-6-trifluoromethyl-2-oxo-1,2-dihydropyrazine (present compound 1-19) and 0.23 g of ethyl 2-bromopropionate was stirred at 130° C. for 3 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 52 mg (yield, 32%) of 3-{5-[1-(ethoxycarbonyl)ethylamino]-4-fluorophenyl}-1-methyl-6-trifluoromethyl-2-oxo-1,2-dihydropyrazine (present compound 1-355; m.p., 78.2° C.).

PRODUCTION EXAMPLE 8

(1) First, 1.20 g of 3-(2,4-dichlorophenyl)-6-trifluoromethyl-2-oxo-1,2-dihydropyrazine (compound 1-1007) was dissolved in 6.0 ml of N,N-dimethylformamide, to which 0.83 g of potassium carbonate and 0.51 ml of methyl iodide were added, and the mixture was stirred at 100° C. for 2 days. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography (eluent, hexane/ethyl acetate=5:1), which afforded 0.81 g (yield, 62%) of 3-(2,4-dichlorophenyl)-1-methyl-6-trifluoromethyl-2-oxo-1,2-dihydropyrazine (present compound 1-332).

$^1$H-NMR (CDCl$_3$/TMS, 250 MHz, δ (ppm)) 3.68 (s, 3H), 7.35 (dd, 1H, J=8.3 Hz, 1.9 Hz), 7.42 (d, 1H, J=8.3 Hz), 7.50 (d, 1H, J=1.9 Hz), 7.84 (s, 1H)

(2) To 1.7 ml of concentrated sulfuric acid was added 0.26 g of 3-(2,4-dichlorophenyl)-1-methyl-6-trifluoromethyl-2-oxo-1,2-dihydropyrazine (present compound 1-332) at 5° C. Furthermore, 85 til of 61% nitric acid was added, and the mixture was stirred at room temperature for 1 hour. After completion of the reaction, the reaction mixture was added to ice water, followed by extraction with chloroform. The organic layer was washed with water and then saturated sodium chloride solution, dried with anhydrous magnesium sulfate, and concentrated. The residue was subjected to silica gel column chromatography, which afforded 0.29 g (yield, 95%) of 3-(2,4dichloro-5-nitrophenyl)-1-methyl-6-trifluoromethyl-2-oxo-1,2-dihydropyrazine (present compound 1-333; m.p., 114.3° C.).

(3) Then, 0.59 g of iron powder was added to a mixture of 5.3 ml of acetic acid and 3.2 ml of water, to which a solution of 0.65 g of 3-(2,4-dichloro-5-nitrophenyl)-1-methyl-6-trifluoromethyl-2-oxo-1,2-dihydropyrazine (present compound 1-333) in 1.6 ml of acetic acid was slowly added dropwise, and the mixture was stirred at room temperature for 2 hours. After completion of the reaction, the reaction mixture was poured into ice water, followed by extraction with ethyl acetate. The organic layer was washed with saturated sodium hydrogencarbonate solution, water, and then saturated sodium chloride solution, dried with anhydrous magnesium sulfate, and concentrated, which afforded 0.49 g (yield, 82%) of 3-(5-amino-2,4-dichlorophenyl)-1-methyl-6-trifluoromethyl-2-oxo-1,2-dihydropyrazine (present compound 1-334; m.p., 188.7° C.).

(4) Then, 0.15 g of 3-(5-amino-2,4-dichlorophenyl)-1-methyl-6-trifluoromethyl-2-oxo-1,2-dihydropyrazine (present compound 1-334) was dissolved in 0.88 ml of pyridine, to which 52 µl of methanesulfonyl chloride was added dropwise, and the mixture was stirred at room temperature for 5 hours. After completion of the reaction, the reaction mixture was poured into water, followed by extraction with chloroform. The organic layer was washed with 2N hydrochloric acid, water, saturated sodium hydrogencarbonate solution, and then saturated sodium chloride solution, dried with anhydrous magnesium sulfate, and concentrated. The residue was subjected to silica gel column chromatography, which afforded 45 mg (yield, 25%) of 3-(2,4-dichloro-5-methanesulfonylaminophenyl)1-methyl-6-trifluoromethyl-2-oxo-1,2-dihydropyrazine (present compound 1-343; m.p., 189.2° C.).

PRODUCTION EXAMPLE 9

A mixture of 0.15 g of 3-(5-amino-2,4-dichlorophenyl)-1-methyl-6-trifluoromethyl-2-oxo-1,2-dihydropyrazine (present compound 1-334) and 172 µl of ethyl 2-bromopropionate was stirred at 150° C. for 3 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 92 mg (yield, 48%) of 3-{2,4-dichloro-5-[1-(ethoxycarbonyl)ethylamino]phenyl}-1-methyl-6-trifluoromethyl-2-oxo-1,2-dihydropyrazine (present compound 1-336).

$^1$H-NMR (CDCl$_3$/TMS, 300 MHz, δ (ppm)) 1.26 (t, 3H, J=7.2 Hz), 1.51 (d, 3H, J=7.0 Hz), 3.67 (s, 3H), 4.1–4.2 (m, 1H), 4.21 (dq, 2H, J=7.2 Hz, 1.6 Hz), 4.94 (d, 1H, J=7.7 Hz), 6.65 (s, 1H), 7.40 (s, 1H), 7.81 (s, 1H)

PRODUCTION EXAMPLE 10

(1) A mixture of 0.35 g of 3-(5-amino-2,4-dichlorophenyl)-1-methyl-6-trifluoromethyl-2-oxo-1,2-dihydropyrazine (present compound 1-334) and 3.1 ml of ethyl chloroformate was stirred at 100° C. for 2 hours. After completion of the reaction, the reaction mixture was left cooling to room temperature, and the excess ethyl chloroformate was distilled out under reduced pressure. The residue was recrystallized from hexane, which afforded 0.32 g (yield, 79%) of 3-(2,4-dichloro-5-ethoxycarbonylaminophenyl)-1-methyl-6-trifluoromethyl-2-oxo-1,2-dihydropyrazine (present compound 1-346; m.p., 116.2–C).

(2) Then, a mixture of 20 mg of sodium hydride (60% in oil) and 1.3 ml of tetrahydrofuran was cooled to 0° C. To this was added dropwise a solution of 0.21 g of 3-(2,4-dichloro-5-ethoxycarbonylaminophenyl)-1-methyl-6-trifluoromethyl-2-oxo-1,2-dihydropyrazine (present compound 1-346) in 1.3 ml of tetrahydrofuran. After stirring at 0° C. for 10 minutes, 42 µl of propargyl bromide was added, and the mixture was stirred at 0° C. for 1 hour. After completion of the reaction, the reaction mixture was poured into saturated ammonium chloride solution, followed by extraction with diethyl ether. The organic layer was dried with anhydrous magnesium sulfate and concentrated. The residue was subjected to silica gel column chromatography, which afforded 36 mg (yield, 16%) of 3-{2,4-dichloro-5-[N-(ethoxycarbonyl)propargylamino]phenyl}-1-methyl-6-trifluoromethyl-2-oxo-1,2-dihydropyrazine (present compound 1-351; m.p., 132.3° C.).

PRODUCTION EXAMPLE 11

First, 0.15 g of 3-(4-chloro-2-fluoro-5-hydroxyphenyl)-1-methyl-6-trifluoromethyl-2-oxo-1,2-dihydropyrazine (present compound 1-61) was dissolved in 0.50 ml of N,N-dimethylformamide, to which 97 mg of potassium carbonate and 48 µl of methyl bromoacetate were added, and the mixture was stirred at room temperature for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 97 mg (yield, 53%) of 3-{4-chloro-2-fluoro-5-[(methoxycarbonyl)methoxy]phenyl}-1-methyl-6-trifluoromethyl-2-oxo-1,2-dihydropyrazine (present compound 1-165; m.p., 116.6° C.).

PRODUCTION EXAMPLE 12

According to the procedure in Production Example 11, 83 mg (yield, 94%) of 3-{4-chloro-2-fluoro-5-[(ethoxycarbonyl)methoxy]phenyl}-1-methyl-6-trifluoromethyl-2-oxo-1,2-dihydropyrazine (present compound 1-166; m.p., 87.5–87.9° C.) was obtained using 70 mg of 3-(4-chloro-2-fluoro-5-hydroxyphenyl)-1-methyl-6-trifluoromethyl-2-oxo-1,2-dihydropyrazine (present compound 1-61), 0.25 ml of N,N-dimethylformamide, 36 mg of potassium carbonate, and 38 mg of ethyl bromoacetate.

PRODUCTION EXAMPLE 13

According to the procedure in Production Example 11, 116 mg (yield, 83%) of 3-{4-chloro-2-fluoro-5-[(pentoxycarbonyl)methoxy]phenyl}-1-methyl-6-trifluoromethyl-2-oxo-1,2-dihydropyrazine (present compound 1-169) was obtained using 100 mg of 3-(4-chloro-2-fluoro-5-hydroxyphenyl)-1-methyl-6-trifluoromethyl-2-oxo-1,2-dihydropyrazine (present compound 1-61), 0.60 ml of N,N-dimethylformamide, 64 mg of potassium carbonate, and 56 mg of pentyl chloroacetate.

$^1$H-NMR (CDCl$_3$/TMS, 300 MHz, δ (ppm)) 0.88 (t, 3H, J=6.9 Hz), 1.2–1.4 (m, 4H), 1.65 (tt, 2H, J=7.0 Hz, 6.9 Hz), 3.68 (s, 3H), 4.20 (t, 2H, J=6.9 Hz), 4.70 (s, 2H), 7.22 (d, 1H, J=6.0 Hz), 7.27 (d, 1H, J=9.4 Hz), 7.83 (s, 1H)

PRODUCTION EXAMPLE 14

According to the procedure in Production Example 11, 130 mg (yield, 96%) of 3-{4-chloro-2-fluoro-5-[(t-butoxycarbonyl)methoxy]phenyl}-1-methyl-6-trifluoromethyl-2-oxo-1,2-dihydropyrazine (present compound 1-356) was obtained using 100 mg of 3-(4-chloro-2-fluoro-5-hydroxyphenyl)-1-methyl-6-trifluoromethyl-2-oxo-1,2-dihydropyrazine (present compound 1-61), 0.60 ml of N,N-dimethylformamide, 64 mg of potassium carbonate, and 66 mg of t-butyl bromoacetate.

$^1$H-NMR (CDCl$_3$/TMS, 300 MHz, δ (ppm)) 1.48 (s, 9H), 3.68 (s, 3H), 4.59 (s, 2H), 7.20 (d, 1H, J=6.2 Hz), 7.26 (d, 1H, J=9.4 Hz), 7.82 (s, 1H)

PRODUCTION EXAMPLE 15

To a solution of 100 mg of 3-{4-chloro-2-fluoro-5-[(methoxycarbonyl)methoxy]phenyl}-1-methyl-6-trifluoromethyl-2-oxo-1,2-dihydropyrazine (present compound 1-165) in 1.0 ml of propanol was added 10 mg of p-toluenesulfonic acid monohydrate, and the mixture was heated under reflux for 5 hours. After completion of the reaction, the reaction mixture was cooled to room temperature, and the excess propanol was distilled out under reduced pressure. The residue was subjected to silica gel column chromatography, which afforded 76 mg (yield, 71%) of 3-{4-chloro-2-fluoro-5-[(propoxycarbonyl)methoxy]phenyl}-1-methyl-6-trifluoromethyl-2-oxo -1,2-dihydropyrazine (present compound 1-167).

$^1$H-NMR (CDCl$_3$/TMS, 250 MHz, δ (ppm)) 0.92 (t, 3H, J=7.4 Hz), 1.68 (tq, 2H, J=7.4 Hz, 6.7 Hz), 3.67 (s, 3H), 4.16 (t, 2H, J=6.7 Hz), 4.71 (s, 2H), 7.23 (d, 1H, J=6.2 Hz), 7.26 (d, 1H, J=9.5 Hz), 7.83 (s, 1H)

PRODUCTION EXAMPLE 16

First, 70 mg of 3-(4-chloro-2-fluoro-5-hydroxyphenyl)-1-methyl-6-trifluoromethyl-2-oxo-1,2-dihydropyrazine (present compound 1-61) was dissolved in 0.25 ml of N,N-dimethylformamide, to which 36 mg of potassium carbonate and 27 mg of propargyl bromide were added, and the mixture was stirred at 50° C. for 2 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 76 mg (yield, 96%) of 3-[4-chloro-2-fluoro-5-(propargyloxy)phenyl]-1-methyl-6-trifluoromethyl-2-oxo-1,2-dihydropyrazine (present compound 1-156; m.p., 106.9–107.1° C.).

PRODUCTION EXAMPLE 17

First, 100 mg of 3-(4-chloro-2-fluoro-5-hydroxyphenyl)-1-methyl-6-trifluoromethyl-2-oxo-1,2-dihydropyrazine (present compound 1-61) was dissolved in 0.60 ml of N,N-dimethylformamide, to which 64 mg of potassium carbonate and 45 mg of 3-bromo-1-butyne were added, and the mixture was stirred at 70° C. for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 96 mg (yield, 83%) of 3-{4-chloro-2-fluoro-5-(3-butyn-2-yloxy)phenyl}-1-methyl-6-trifluoromethyl-2-oxo-1,2-dihydropyrazine (present compound 1-157).

$^1$H-NMR (CDCl$_3$/TMS, 300 MHz, δ (ppm)) 1.72 (d, 3H, J=6.7 Hz), 2.52 (d, 1H, J=2.1 Hz), 3.69 (s, 3H), 4.88 (dq, 1H, J=6.7 Hz, 2.1 Hz), 7.25 (d, 1H, J=9.5 Hz), 7.46 (d, 1H, J=6.2 Hz), 7.84 (s, 1H)

PRODUCTION EXAMPLE 18

(1) First, 2.20 g of 3-(2,4-dichloro-5-methoxyphenyl)-6-trifluoromethyl-2-oxo-1,2-dihydropyrazin (compound 1-1009) was dissolved in 12 ml of N,N-dimethylformamide, to which 1.34 g of potassium carbonate and 0.81 ml of methyl iodide were added, and the mixture was stirred at 100° C. for 2 days. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography (eluent, hexane/ethyl acetate=5:1), which afforded 1.11 g (yield, 48%) of 3-(2,4-dichloro-5-methoxyphenyl)-1-methyl-6-trifluoromethyl-2-oxo-1,2-dihydropyrazine (present compound 1-358; m.p., 130.6° C.).

(2) A mixture of 1.00 g of 3-(2,4-dichloro-5-methoxyphenyl)-1-methyl-6-trifluoromethyl-2-oxo-1,2-dihydropyrazine (present compound 1-358) and 16 ml of 48% hydrobromic acid was dissolved in 5.7 ml of acetic acid, and the solution was stirred at 140° C. for 1 hour. After completion of the reaction, the reaction mixture was poured into water, followed by extraction with ethyl acetate. The organic layer was washed with saturated sodium hydrogencarbonate, water, and then saturated sodium chloride solution, dried with anhydrous magnesium sulfate, and concentrated. The residue was subjected to silica gel column chromatography, which afforded 0.74 g (yield, 77%) of 3-(2,4-dichloro-5-hydroxyphenyl)-1-methyl-6-trifluoromethyl-2-oxo-1,2-dihydropyrazine (present compound 1-357; m.p., 173.5° C.).

(3) Then, 0.15 g of 3-(2,4-dichloro-5-hydroxyphenyl)-1-methyl-6-trifluoromethyl-2-oxo-1,2-dihydropyrazine (present compound 1-357) was dissolved in 0.90 ml of N,N-dimethylformamide, to which 0.092 g of potassium carbonate and 54 µl of methyl 2-bromopropionate were added, and the mixture was stirred at room temperature for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 0.184 g (yield, 98%) of 3-(2,4-dichloro-5-(1-methoxycarbonylethoxy)phenyl)-1-methyl-6-trifluoromethyl-2-oxo-1,2-dihydropyrazine (present compound 1-387).

$^1$H-NMR (CDCl$_3$/TMS, 300 MHz, δ (ppm)) 1.68 (d, 3H, J=6.8 Hz), 3.68 (s, 3H), 3.75 (s, 3H), 4.77 (q, 1H, J=6.8 Hz), 6.99 (s, 1H), 7.51 (s, 1H), 7.83 (s, 1H)

PRODUCTION EXAMPLE 19

First, 0.15 g of 3-(2,4-dichloro-5-hydroxyphenyl)-1-methyl-6-trifluoromethyl-2-oxo-1,2-dihydropyrazine (present compound 1-357) was dissolved in 0.90 ml of N,N-dimethylformamide, to which 92 mg of potassium carbonate and 82 mg of ethyl bromoacetate were added, and the mixture was stirred at room temperature for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 179 mg (yield, 96%) of 3-{2,4-dichloro-5-[(ethoxycarbonyl)methoxy]phenyl}-1-methyl-6-trifluoromethyl-2-oxo-1,2-dihydropyrazine (present compound 1-380).

$^1$H-NMR (CDCl$_3$/TMS, 300 MHz, δ (ppm)) 1.28 (t, 3H, J=7.4 Hz), 3.68 (s, 3H), 4.26 (q, 2H, J=7.4 Hz), 4.69 (s, 2H), 7.00 (s, 1H), 7.52 (s, 1H), 7.83 (s, 1H)

PRODUCTION EXAMPLE 20

First, 150 mg of 3-(2,4-dichloro-5-hydroxyphenyl)-1-methyl-6-trifluoromethyl-2-oxo-1,2-dihydropyrazine (present compound 1-357) was dissolved in 0.90 ml of N,N-dimethylformamide, to which 92 mg of potassium carbonate and 58 mg of propargyl bromide were added, and the mixture was stirred at room temperature for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 160 mg (yield, 96%) of 3-[2,4-dichloro-5-(propargyloxy)phenyl]-1-methyl-6-trifluoromethyl-2-oxo-1,2-dihydropyrazine (present compound 1-370; m.p., 123.7° C.).

$^1$H-NMR (CDCl$_3$/TMS, 250 MHz, δ (ppm)) 2.56 (t, 1H, J=2.4 Hz), 3.69 (s, 3H), 4.78 (d, 2H, J=2.4 Hz), 7.18 (s, 1H), 7.52 (s, 1H), 7.85 (s, 1H)

PRODUCTION EXAMPLE 21

First, 150 mg of 3-(2,4-dichloro-5-hydroxyphenyl)-1-methyl-6-trifluoromethyl-2-oxo-1,2-dihydropyrazine (present compound 1-357) was dissolved in 0.90 ml of N,N-dimethylformamide, to which 92 mg of potassium carbonate and 65 mg of 3-bromo-1-butyne were added, and the mixture was stirred at room temperature for 1 hour. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 159 mg (yield, 92%) of 3-{2,4-dichloro-5-(3-butyn-2-yloxy)phenyl}-1-methyl-6-trifluoromethyl-2-oxo-1,2-dihydropyrazine (present compound 1-371).

$^1$H-NMR (CDCl$_3$/TMS, 250 MHz, δ (ppm)) 1.72 (d, 3H, J=6.6 Hz), 2.52 (d, 1H, J=2.0 Hz), 3.69 (s, 3H), 4.87 (dq, 1H, J=6.6 Hz, 2.0 Hz), 7.26 (s, 1H), 7.51 (s, 1H), 7.84 (s, 1H)

PRODUCTION EXAMPLE 22

A mixture of 0.12 g of 3-(5-amino-4-chloro-2-fluorophenyl)-1-methyl-6-trifluoromethyl-2-oxo-1,2-dihydropyrazine (present compound 1-23) and 247 mg of methyl 2-bromopropionate was stirred at 140° C. for 3 hours. After completion of the reaction, the reaction mixture was poured into water, followed by extraction with ethyl acetate. The organic layer was washed with saturated sodium chloride solution, dried with anhydrous magnesium sulfate, and concentrated. The residue was subjected to silica gel column chromatography, which afforded 125 mg (yield, 83%) of 3-{4-chloro-5-[1-(methoxycarbonyl)ethylamino]-2-fluorophenyl}-1-methyl-6-trifluoromethyl-2-oxo-1,2-dihydropyrazine (present compound 1-89).

$^1$H-NMR (CDCl$_3$/TMS, 300 MHz, δ (ppm)) 1.53 (d, 3H, J=6.9 Hz), 3.67 (s, 3H), 3.75 (s, 3H), 4.1–4.2 (m, 1H), 4.7–4.8 (br, 1H), 6.82 (d, 1H, J=6.2 Hz), 7.17 (d, 1H, J=9.5 Hz), 7.82 (s, 1H)

Some of the present compounds are shown with their compound numbers in Tables 1 to 5, where the symbol "n" refers to normal-; "i", iso-; "c", cyclo-; and "t", tertiary-.

TABLE 1

Compounds of the formula:

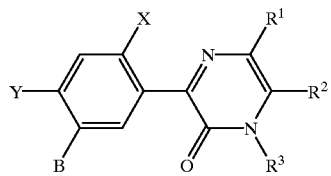

| Compound No. | X | Y | R$^1$ | R$^2$ | R$^3$ | B |
|---|---|---|---|---|---|---|
| 1-1 | H | F | H | CF$_3$ | C$_2$H$_5$ | H |
| 1-2 | H | Cl | H | CF$_3$ | C$_2$H$_5$ | H |
| 1-3 | H | Br | H | CF$_3$ | C$_2$H$_5$ | H |
| 1-4 | H | F | H | CF$_3$ | CH$_3$ | H |
| 1-5 | H | Cl | H | CF$_3$ | CH$_3$ | H |
| 1-6 | H | Br | H | CF$_3$ | CH$_3$ | H |
| 1-7 | F | F | H | CF$_3$ | C$_2$H$_5$ | H |
| 1-8 | F | Cl | H | CF$_3$ | C$_2$H$_5$ | H |
| 1-9 | F | Br | H | CF$_3$ | C$_2$H$_5$ | H |
| 1-10 | F | F | H | CF$_3$ | CH$_3$ | H |
| 1-11 | F | Cl | H | CF$_3$ | CH$_3$ | H |
| 1-12 | F | Br | H | CF$_3$ | CH$_3$ | H |
| 1-13 | H | F | H | CF$_3$ | CH$_3$ | NO$_2$ |
| 1-14 | H | Cl | H | CF$_3$ | CH$_3$ | NO$_2$ |
| 1-15 | H | Br | H | CF$_3$ | CH$_3$ | NO$_2$ |
| 1-16 | F | F | H | CF$_3$ | CH$_3$ | NO$_2$ |
| 1-17 | F | Cl | H | CF$_3$ | CH$_3$ | NO$_2$ |
| 1-18 | F | Br | H | CF$_3$ | CH$_3$ | NO$_2$ |
| 1-19 | H | F | H | CF$_3$ | CH$_3$ | NH$_2$ |
| 1-20 | H | Cl | H | CF$_3$ | CH$_3$ | NH$_2$ |
| 1-21 | H | Br | H | CF$_3$ | CH$_3$ | NH$_2$ |
| 1-22 | F | F | H | CF$_3$ | CH$_3$ | NH$_2$ |
| 1-23 | F | Cl | H | CF$_3$ | CH$_3$ | NH$_2$ |
| 1-24 | H | Cl | H | CF$_3$ | CH$_3$ | NHCH(CH$_3$)COOCH$_3$ |
| 1-25 | H | Cl | H | CF$_3$ | CH$_3$ | NHCH(CH$_3$)COOC$_2$H$_5$ |
| 1-26 | H | Cl | H | CF$_3$ | CH$_3$ | NHCH(CH$_3$)COO$^n$C$_3$H$_7$ |
| 1-27 | H | Cl | H | CF$_3$ | CH$_3$ | NHCH(CH$_3$)COO$^n$C$_4$H$_9$ |
| 1-28 | H | Cl | H | CF$_3$ | CH$_3$ | NHCH(CH$_3$)COO$^n$C$_5$H$_{11}$ |
| 1-29 | H | Cl | H | CF$_3$ | CH$_3$ | NHCH(CH$_3$)COO$^i$C$_3$H$_7$ |
| 1-30 | H | Cl | H | CF$_3$ | CH$_3$ | NHCH(CH$_3$)COO$^c$C$_5$H$_9$ |
| 1-31 | H | Cl | H | CF$_3$ | CH$_3$ | NHCH(CH$_3$)COO$^c$C$_6$H$_{11}$ |
| 1-32 | F | Cl | H | CF$_3$ | CH$_3$ | NHCH$_3$ |
| 1-33 | F | Cl | H | CF$_3$ | CH$_3$ | NHC$_2$H$_5$ |
| 1-34 | F | Cl | H | CF$_3$ | CH$_3$ | NHCH$_2$CH=CH$_2$ |
| 1-35 | F | Cl | H | CF$_3$ | CH$_3$ | NHCH$_2$C≡CH |
| 1-36 | F | Cl | H | CF$_3$ | CH$_3$ | NHCH(CH$_3$)C≡CH |
| 1-37 | F | Cl | H | CF$_3$ | CH$_3$ | NHSO$_2$CH$_3$ |
| 1-38 | F | Cl | H | CF$_3$ | CH$_3$ | NHSO$_2$C$_2$H$_5$ |
| 1-39 | F | Cl | H | CF$_3$ | CH$_3$ | NHSO$_2$CH$_2$Cl |
| 1-40 | F | Cl | H | CF$_3$ | CH$_3$ | NHSO$_2$CF$_3$ |
| 1-41 | F | Cl | H | CF$_3$ | CH$_3$ | N(CH$_3$)SO$_2$CH$_3$ |
| 1-42 | F | Cl | H | CF$_3$ | CH$_3$ | N(CH$_2$C≡CH)SO$_2$CH$_3$ |
| 1-43 | F | Cl | H | CF$_3$ | CH$_3$ | NHCOOCH$_3$ |
| 1-44 | F | Cl | H | CF$_3$ | CH$_3$ | NHCOOC$_2$H$_5$ |
| 1-45 | F | Cl | H | CF$_3$ | CH$_3$ | NHCOO$^n$C$_3$H$_7$ |
| 1-46 | F | Cl | H | CF$_3$ | CH$_3$ | NHCOO$^i$C$_3$H$_7$ |
| 1-47 | F | Cl | H | CF$_3$ | CH$_3$ | NHCOO$^n$C$_4$H$_9$ |
| 1-48 | F | Cl | H | CF$_3$ | CH$_3$ | NHCOO$^n$C$_5$H$_{11}$ |
| 1-49 | F | Cl | H | CF$_3$ | CH$_3$ | NHCH$_2$COOCH$_3$ |
| 1-50 | F | Cl | H | CF$_3$ | CH$_3$ | NHCH$_2$COOC$_2$H$_5$ |
| 1-51 | F | Cl | H | CF$_3$ | CH$_3$ | NHCH$_2$COO$^n$C$_3$H$_7$ |
| 1-52 | F | Cl | H | CF$_3$ | CH$_3$ | NHCH$_2$COO$^n$C$_4$H$_9$ |
| 1-53 | F | Cl | H | CF$_3$ | CH$_3$ | NHCH$_2$COO$^n$C$_5$H$_{11}$ |
| 1-54 | F | Cl | H | CF$_3$ | CH$_3$ | NHCH$_2$COO$^i$C$_3$H$_7$ |
| 1-55 | F | Cl | H | CF$_3$ | CH$_3$ | NHCH$_2$COO$^c$C$_5$H$_9$ |
| 1-56 | F | Br | H | CF$_3$ | CH$_3$ | NH$_2$ |
| 1-57 | H | F | H | CF$_3$ | CH$_3$ | OH |
| 1-58 | H | Cl | H | CF$_3$ | CH$_3$ | OH |
| 1-59 | H | Br | H | CF$_3$ | CH$_3$ | OH |
| 1-60 | F | F | H | CF$_3$ | CH$_3$ | OH |
| 1-61 | F | Cl | H | CF$_3$ | CH$_3$ | OH |
| 1-62 | F | Br | H | CF$_3$ | CH$_3$ | OH |
| 1-63 | H | Cl | H | CF$_3$ | CH$_3$ | NHCH$_3$ |

TABLE 1-continued

Compounds of the formula:

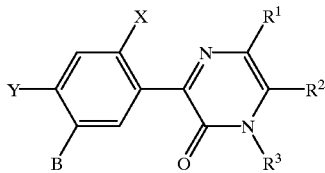 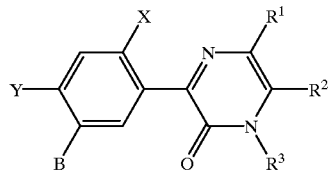

| Compound No. | X | Y | $R^1$ | $R^2$ | $R^3$ | B |
|---|---|---|---|---|---|---|
| 1-64 | H | Cl | H | $CF_3$ | $CH_3$ | $NHC_2H_5$ |
| 1-65 | H | Cl | H | $CF_3$ | $CH_3$ | $NHCH_2CH=CH_2$ |
| 1-66 | H | Cl | H | $CF_3$ | $CH_3$ | $NHCH_2C\equiv CH$ |
| 1-67 | H | Cl | H | $CF_3$ | $CH_3$ | $NHCH(CH_3)C\equiv CH$ |
| 1-68 | H | Cl | H | $CF_3$ | $CH_3$ | $NHSO_2CH_3$ |
| 1-69 | H | Cl | H | $CF_3$ | $CH_3$ | $NHSO_2C_2H_5$ |
| 1-70 | H | Cl | H | $CF_3$ | $CH_3$ | $NHSO_2CH_2Cl$ |
| 1-71 | H | Cl | H | $CF_3$ | $CH_3$ | $NHSO_2CF_3$ |
| 1-72 | H | Cl | H | $CF_3$ | $CH_3$ | $N(CH_3)SO_2CH_3$ |
| 1-73 | H | Cl | H | $CF_3$ | $CH_3$ | $N(CH_2C\equiv CH)SO_2CH_3$ |
| 1-74 | H | Cl | H | $CF_3$ | $CH_3$ | $NHCOOCH_3$ |
| 1-75 | H | Cl | H | $CF_3$ | $CH_3$ | $NHCOOC_2H_5$ |
| 1-76 | H | Cl | H | $CF_3$ | $CH_3$ | $NHCOO^nC_3H_7$ |
| 1-77 | H | Cl | H | $CF_3$ | $CH_3$ | $NHCOO^iC_3H_7$ |
| 1-78 | H | Cl | H | $CF_3$ | $CH_3$ | $NHCOO^nC_4H_9$ |
| 1-79 | H | Cl | H | $CF_3$ | $CH_3$ | $NHCOO^nC_5H_{11}$ |
| 1-80 | H | Cl | H | $CF_3$ | $CH_3$ | $NHCH_2COOCH_3$ |
| 1-81 | H | Cl | H | $CF_3$ | $CH_3$ | $NHCH_2COOC_2H_5$ |
| 1-82 | H | Cl | H | $CF_3$ | $CH_3$ | $NHCH_2COO^nC_3H_7$ |
| 1-83 | H | Cl | H | $CF_3$ | $CH_3$ | $NHCH_2COO^nC_4H_9$ |
| 1-84 | H | Cl | H | $CF_3$ | $CH_3$ | $NHCH_2COO^nC_5H_{11}$ |
| 1-85 | H | Cl | H | $CF_3$ | $CH_3$ | $NHCH_2COO^iC_3H_7$ |
| 1-86 | H | Cl | H | $CF_3$ | $CH_3$ | $NHCH_2COO^cC_5H_9$ |
| 1-87 | H | Cl | H | $CF_3$ | $CH_3$ | $NHCH_2COO^cC_6H_{11}$ |
| 1-88 | F | Cl | H | $CF_3$ | $CH_3$ | $NHCH_2COO^cC_6H_{11}$ |
| 1-89 | F | Cl | H | $CF_3$ | $CH_3$ | $NHCH(CH_3)COOCH_3$ |
| 1-90 | F | Cl | H | $CF_3$ | $CH_3$ | $NHCH(CH_3)COOC_2H_5$ |
| 1-91 | F | Cl | H | $CF_3$ | $CH_3$ | $NHCH(CH_3)COO^nC_3H_7$ |
| 1-92 | F | Cl | H | $CF_3$ | $CH_3$ | $NHCH(CH_3)COO^nC_4H_9$ |
| 1-93 | F | Cl | H | $CF_3$ | $CH_3$ | $NHCH(CH_3)COO^nC_5H_{11}$ |
| 1-94 | F | Cl | H | $CF_3$ | $CH_3$ | $NHCH(CH_3)COO^iC_3H_7$ |
| 1-95 | F | Cl | H | $CF_3$ | $CH_3$ | $NHCH(CH_3)COO^cC_5H_9$ |
| 1-96 | F | Cl | H | $CF_3$ | $CH_3$ | $NHCH(CH_3)COO^cC_6H_{11}$ |
| 1-97 | H | Cl | H | $CF_3$ | $CH_3$ | $OCH_3$ |
| 1-98 | H | Cl | H | $CF_3$ | $CH_3$ | $OC_2H_5$ |
| 1-99 | H | Cl | H | $CF_3$ | $CH_3$ | $O^iC_3H_7$ |
| 1-100 | H | Cl | H | $CF_3$ | $CH_3$ | $O^nC_3H_7$ |
| 1-101 | H | Cl | H | $CF_3$ | $CH_3$ | $OCH_2CH_2Cl$ |
| 1-102 | H | Cl | H | $CF_3$ | $CH_3$ | $OCF_2CF_2H$ |
| 1-103 | H | Cl | H | $CF_3$ | $CH_3$ | $O^cC_5H_9$ |
| 1-104 | H | Cl | H | $CF_3$ | $CH_3$ | $O^cC_6H_{11}$ |
| 1-105 | H | Cl | H | $CF_3$ | $CH_3$ | $OCH_2CH=CH_2$ |
| 1-106 | H | Cl | H | $CF_3$ | $CH_3$ | $OCH_2CCl=CH_2$ |
| 1-107 | H | Cl | H | $CF_3$ | $CH_3$ | $OCH_2CCl=CHCl$ |
| 1-108 | H | Cl | H | $CF_3$ | $CH_3$ | $OCH(CH_3)CH=CH_2$ |
| 1-109 | H | Cl | H | $CF_3$ | $CH_3$ | $OCH_2C\equiv CH$ |
| 1-110 | H | Cl | H | $CF_3$ | $CH_3$ | $OCH(CH_3)C\equiv CH$ |
| 1-111 | H | Cl | H | $CF_3$ | $CH_3$ | $OCH_2C\equiv CBr$ |
| 1-112 | H | Cl | H | $CF_3$ | $CH_3$ | $OCH_2C\equiv CCl$ |
| 1-113 | H | Cl | H | $CF_3$ | $CH_3$ | $OCH_2C\equiv CCH_2Cl$ |
| 1-114 | H | Cl | H | $CF_3$ | $CH_3$ | $OCH_2CN$ |
| 1-115 | H | Cl | H | $CF_3$ | $CH_3$ | $OCH_2OCH_3$ |
| 1-116 | H | Cl | H | $CF_3$ | $CH_3$ | $OCH_2OC_2H_5$ |
| 1-117 | H | Cl | H | $CF_3$ | $CH_3$ | $OCH_2SCH_3$ |
| 1-118 | H | Cl | H | $CF_3$ | $CH_3$ | $OCH_2COOCH_3$ |
| 1-119 | H | Cl | H | $CF_3$ | $CH_3$ | $OCH_2COOC_2H_5$ |
| 1-120 | H | Cl | H | $CF_3$ | $CH_3$ | $OCH_2COO^nC_3H_7$ |
| 1-121 | H | Cl | H | $CF_3$ | $CH_3$ | $OCH_2COO^nC_4H_9$ |
| 1-122 | H | Cl | H | $CF_3$ | $CH_3$ | $OCH_2COO^nC_5H_{11}$ |
| 1-123 | H | Cl | H | $CF_3$ | $CH_3$ | $OCH_2COO^iC_3H_7$ |
| 1-124 | H | Cl | H | $CF_3$ | $CH_3$ | $OCH_2COO^cC_5H_9$ |
| 1-125 | H | Cl | H | $CF_3$ | $CH_3$ | $OCH_2COO^cC_6H_{11}$ |
| 1-126 | H | Cl | H | $CF_3$ | $CH_3$ | $OCH(CH_3)COOCH_3$ |
| 1-127 | H | Cl | H | $CF_3$ | $CH_3$ | $OCH(CH_3)COOC_2H_5$ |
| 1-128 | H | Cl | H | $CF_3$ | $CH_3$ | $OCH(CH_3)COO^nC_3H_7$ |
| 1-129 | H | Cl | H | $CF_3$ | $CH_3$ | $OCH(CH_3)COO^nC_4H_9$ |
| 1-130 | H | Cl | H | $CF_3$ | $CH_3$ | $OCH(CH_3)COO^nC_5H_{11}$ |
| 1-131 | H | Cl | H | $CF_3$ | $CH_3$ | $OCH(CH_3)COO^iC_3H_7$ |
| 1-132 | H | Cl | H | $CF_3$ | $CH_3$ | $OCH(CH_3)COO^cC_5H_9$ |
| 1-133 | H | Cl | H | $CF_3$ | $CH_3$ | $OCH(CH_3)COO^cC_6H_{11}$ |
| 1-134 | H | Cl | H | $CF_3$ | $CH_3$ | $OCH_2CON(CH_3)_2$ |
| 1-135 | H | Cl | H | $CF_3$ | $CH_3$ | $OCH_2CON(C_2H_5)_2$ |
| 1-136 | H | Cl | H | $CF_3$ | $CH_3$ | $OCH_2CON(CH_3)C_2H_5$ |
| 1-137 | H | Cl | H | $CF_3$ | $CH_3$ | $OCH(CH_3)CON(CH_3)_2$ |
| 1-138 | H | Cl | H | $CF_3$ | $CH_3$ | $OCH(CH_3)CON(C_2H_5)_2$ |
| 1-139 | H | Cl | H | $CF_3$ | $CH_3$ | $OCH(CH_3)CON(CH_3)C_2H_5$ |
| 1-140 | H | Cl | H | $CF_3$ | $CH_3$ | $OCH_2COON(CH_3)_2$ |
| 1-141 | H | Cl | H | $CF_3$ | $CH_3$ | $OCH_2COON(C_2H_5)_2$ |
| 1-142 | H | Cl | H | $CF_3$ | $CH_3$ | $OCH(CH_3)COON(CH_3)_2$ |
| 1-143 | H | Cl | H | $CF_3$ | $CH_3$ | $OCH(CH_3)COON(C_2H_5)_2$ |
| 1-144 | F | Cl | H | $CF_3$ | $CH_3$ | $OCH_3$ |
| 1-145 | F | Cl | H | $CF_3$ | $CH_3$ | $OC_2H_5$ |
| 1-146 | F | Cl | H | $CF_3$ | $CH_3$ | $O^iC_3H_5$ |
| 1-147 | F | Cl | H | $CF_3$ | $CH_3$ | $O^nC_3H_7$ |
| 1-148 | F | Cl | H | $CF_3$ | $CH_3$ | $OCH_2CH_2Cl$ |
| 1-149 | F | Cl | H | $CF_3$ | $CH_3$ | $OCF_2CF_2H$ |
| 1-150 | F | Cl | H | $CF_3$ | $CH_3$ | $O^cC_5H_9$ |
| 1-151 | F | Cl | H | $CF_3$ | $CH_3$ | $O^cC_6H_{11}$ |
| 1-152 | F | Cl | H | $CF_3$ | $CH_3$ | $OCH_2CH=CH_2$ |
| 1-153 | F | Cl | H | $CF_3$ | $CH_3$ | $OCH_2CCl=CH_2$ |
| 1-154 | F | Cl | H | $CF_3$ | $CH_3$ | $OCH_2CCl=CHCl$ |
| 1-155 | F | Cl | H | $CF_3$ | $CH_3$ | $OCH(CH_3)CH=CH_2$ |
| 1-156 | F | Cl | H | $CF_3$ | $CH_3$ | $OCH_2C\equiv CH$ |
| 1-157 | F | Cl | H | $CF_3$ | $CH_3$ | $OCH(CH_3)C\equiv CH$ |
| 1-158 | F | Cl | H | $CF_3$ | $CH_3$ | $OCH_2C\equiv CBr$ |
| 1-159 | F | Cl | H | $CF_3$ | $CH_3$ | $OCH_2C\equiv CCl$ |
| 1-160 | F | Cl | H | $CF_3$ | $CH_3$ | $OCH_2C\equiv CCH_2Cl$ |
| 1-161 | F | Cl | H | $CF_3$ | $CH_3$ | $OCH_2CN$ |
| 1-162 | F | Cl | H | $CF_3$ | $CH_3$ | $OCH_2OCH_3$ |
| 1-163 | F | Cl | H | $CF_3$ | $CH_3$ | $OCH_2OC_2H_5$ |
| 1-164 | F | Cl | H | $CF_3$ | $CH_3$ | $OCH_2SCH_3$ |
| 1-165 | F | Cl | H | $CF_3$ | $CH_3$ | $OCH_2COOCH_3$ |
| 1-166 | F | Cl | H | $CF_3$ | $CH_3$ | $OCH_2COOC_2H_5$ |
| 1-167 | F | Cl | H | $CF_3$ | $CH_3$ | $OCH_2COO^nC_3H_7$ |
| 1-168 | F | Cl | H | $CF_3$ | $CH_3$ | $OCH_2COO^nC_4H_9$ |
| 1-169 | F | Cl | H | $CF_3$ | $CH_3$ | $OCH_2COO^nC_5H_{11}$ |
| 1-170 | F | Cl | H | $CF_3$ | $CH_3$ | $OCH_2COO^iC_3H_7$ |
| 1-171 | F | Cl | H | $CF_3$ | $CH_3$ | $OCH_2COO^cC_5H_9$ |
| 1-172 | F | Cl | H | $CF_3$ | $CH_3$ | $OCH_2COO^cC_6H_{11}$ |
| 1-173 | F | Cl | H | $CF_3$ | $CH_3$ | $OCH(CH_3)COOCH_3$ |
| 1-174 | F | Cl | H | $CF_3$ | $CH_3$ | $OCH(CH_3)COOC_2H_5$ |
| 1-175 | F | Cl | H | $CF_3$ | $CH_3$ | $OCH(CH_3)COO^nC_3H_7$ |
| 1-176 | F | Cl | H | $CF_3$ | $CH_3$ | $OCH(CH_3)COO^nC_4H_9$ |
| 1-177 | F | Cl | H | $CF_3$ | $CH_3$ | $OCH(CH_3)COO^nC_5H_{11}$ |
| 1-178 | F | Cl | H | $CF_3$ | $CH_3$ | $OCH(CH_3)COO^iC_3H_7$ |
| 1-179 | F | Cl | H | $CF_3$ | $CH_3$ | $OCH(CH_3)COO^cC_5H_9$ |
| 1-180 | F | Cl | H | $CF_3$ | $CH_3$ | $OCH(CH_3)COO^cC_6H_{11}$ |
| 1-181 | F | Cl | H | $CF_3$ | $CH_3$ | $OCH_2CON(CH_3)_2$ |
| 1-182 | F | Cl | H | $CF_3$ | $CH_3$ | $OCH_2CON(C_2H_5)_2$ |
| 1-183 | F | Cl | H | $CF_3$ | $CH_3$ | $OCH_2CON(CH_3)C_2H_5$ |
| 1-184 | F | Cl | H | $CF_3$ | $CH_3$ | $OCH(CH_3)CON(CH_3)_2$ |
| 1-185 | F | Cl | H | $CF_3$ | $CH_3$ | $OCH(CH_3)CON(C_2H_5)_2$ |
| 1-186 | F | Cl | H | $CF_3$ | $CH_3$ | $OCH(CH_3)CON(CH_3)C_2H_5$ |
| 1-187 | F | Cl | H | $CF_3$ | $CH_3$ | $OCH_2COON(CH_3)_2$ |
| 1-188 | F | Cl | H | $CF_3$ | $CH_3$ | $OCH_2COON(C_2H_5)_2$ |
| 1-189 | F | Cl | H | $CF_3$ | $CH_3$ | $OCH(CH_3)COON(CH_3)_2$ |

TABLE 1-continued

Compounds of the formula:

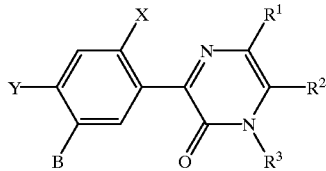

| Compound No. | X | Y | $R^1$ | $R^2$ | $R^3$ | B |
|---|---|---|---|---|---|---|
| 1-190 | F | Cl | H | $CF_3$ | $CH_3$ | $OCH(CH_3)COON(C_2H_5)_2$ |
| 1-191 | H | F | H | $CF_3$ | $CH_3$ | SH |
| 1-192 | H | Cl | H | $CF_3$ | $CH_3$ | SH |
| 1-193 | H | Br | H | $CF_3$ | $CH_3$ | SH |
| 1-194 | F | F | H | $CF_3$ | $CH_3$ | SH |
| 1-195 | F | Cl | H | $CF_3$ | $CH_3$ | SH |
| 1-196 | F | Br | H | $CF_3$ | $CH_3$ | SH |
| 1-197 | H | Cl | H | $CF_3$ | $CH_3$ | $SCH_3$ |
| 1-198 | H | Cl | H | $CF_3$ | $CH_3$ | $SC_2H_5$ |
| 1-199 | H | Cl | H | $CF_3$ | $CH_3$ | $Si^iC_3H_7$ |
| 1-200 | H | Cl | H | $CF_3$ | $CH_3$ | $SCH_2CH_2Cl$ |
| 1-201 | H | Cl | H | $CF_3$ | $CH_3$ | $S^cC_5H_9$ |
| 1-202 | H | Cl | H | $CF_3$ | $CH_3$ | $S^cC_6H_{11}$ |
| 1-203 | H | Cl | H | $CF_3$ | $CH_3$ | $SCH_2CH=CH_2$ |
| 1-204 | H | Cl | H | $CF_3$ | $CH_3$ | $SCH_2CCl=CH_2$ |
| 1-205 | H | Cl | H | $CF_3$ | $CH_3$ | $SCH_2CCl=CHCl$ |
| 1-206 | H | Cl | H | $CF_3$ | $CH_3$ | $SCH(CH_3)CH=CH_2$ |
| 1-207 | H | Cl | H | $CF_3$ | $CH_3$ | $SCH_2C\equiv CH$ |
| 1-208 | H | Cl | H | $CF_3$ | $CH_3$ | $SCH(CH_3)C\equiv CH$ |
| 1-209 | H | Cl | H | $CF_3$ | $CH_3$ | $SCH_2COOCH_3$ |
| 1-210 | H | Cl | H | $CF_3$ | $CH_3$ | $SCH_2COOC_2H_5$ |
| 1-211 | H | Cl | H | $CF_3$ | $CH_3$ | $SCH_2COO^nC_3H_7$ |
| 1-212 | H | Cl | H | $CF_3$ | $CH_3$ | $SCH_2COO^nC_4H_9$ |
| 1-213 | H | Cl | H | $CF_3$ | $CH_3$ | $SCH_2COO^nC_5H_{11}$ |
| 1-214 | H | Cl | H | $CF_3$ | $CH_3$ | $SCH_2COO^iC_3H_7$ |
| 1-215 | H | Cl | H | $CF_3$ | $CH_3$ | $SCH_2COO^cC_5H_9$ |
| 1-216 | H | Cl | H | $CF_3$ | $CH_3$ | $SCH_2COO^cC_6H_{11}$ |
| 1-217 | H | Cl | H | $CF_3$ | $CH_3$ | $SCH(CH_3)COOCH_3$ |
| 1-218 | H | Cl | H | $CF_3$ | $CH_3$ | $SCH(CH_3)COOC_2H_5$ |
| 1-219 | H | Cl | H | $CF_3$ | $CH_3$ | $SCH(CH_3)COO^nC_3H_7$ |
| 1-220 | H | Cl | H | $CF_3$ | $CH_3$ | $SCH(CH_3)COO^nC_4H_9$ |
| 1-221 | H | Cl | H | $CF_3$ | $CH_3$ | $SCH(CH_3)COO^nC_5H_{11}$ |
| 1-222 | H | Cl | H | $CF_3$ | $CH_3$ | $SCH(CH_3)COO^iC_3H_7$ |
| 1-223 | H | Cl | H | $CF_3$ | $CH_3$ | $SCH(CH_3)COO^cC_5H_9$ |
| 1-224 | H | Cl | H | $CF_3$ | $CH_3$ | $SCH(CH_3)COO^cC_6H_{11}$ |
| 1-225 | H | Cl | H | $CF_3$ | $CH_3$ | $SCH_2CON(CH_3)_2$ |
| 1-226 | H | Cl | H | $CF_3$ | $CH_3$ | $SCH_2CON(C_2H_5)_2$ |
| 1-227 | H | Cl | H | $CF_3$ | $CH_3$ | $SCH_2CON(tetramethylene)$ |
| 1-228 | H | Cl | H | $CF_3$ | $CH_3$ | $SCH_2CON(pentamethylene)$ |
| 1-229 | H | Cl | H | $CF_3$ | $CH_3$ | $SCH_2CON(ethyleneoxyethylene)$ |
| 1-230 | H | Cl | H | $CF_3$ | $CH_3$ | $SCH(CH_3)CON(CH_3)_2$ |
| 1-231 | H | Cl | H | $CF_3$ | $CH_3$ | $SCH(CH_3)CON(C_2H_5)_2$ |
| 1-232 | H | Cl | H | $CF_3$ | $CH_3$ | $SCH(CH_3)CON(tetramethylene)$ |
| 1-233 | H | Cl | H | $CF_3$ | $CH_3$ | $SCH(CH_3)CON(pentamethylene)$ |
| 1-234 | F | Cl | H | $CF_3$ | $CH_3$ | $SCH_3$ |
| 1-235 | F | Cl | H | $CF_3$ | $CH_3$ | $SC_2H_5$ |
| 1-236 | F | Cl | H | $CF_3$ | $CH_3$ | $Si^iC_3H_7$ |
| 1-237 | F | Cl | H | $CF_3$ | $CH_3$ | $SCH_2CH_2Cl$ |
| 1-238 | F | Cl | H | $CF_3$ | $CH_3$ | $S^cC_5H_9$ |
| 1-239 | F | Cl | H | $CF_3$ | $CH_3$ | $S^cC_6H_{11}$ |
| 1-240 | F | Cl | H | $CF_3$ | $CH_3$ | $SCH_2CH=CH_2$ |
| 1-241 | F | Cl | H | $CF_3$ | $CH_3$ | $SCH_2CCl=CH_2$ |
| 1-242 | F | Cl | H | $CF_3$ | $CH_3$ | $SCH_2CCl=CHCl$ |
| 1-243 | F | Cl | H | $CF_3$ | $CH_3$ | $SCH(CH_3)CH=CH_2$ |
| 1-244 | F | Cl | H | $CF_3$ | $CH_3$ | $SCH_2C\equiv CH$ |
| 1-245 | F | Cl | H | $CF_3$ | $CH_3$ | $SCH(CH_3)C\equiv CH$ |
| 1-246 | F | Cl | H | $CF_3$ | $CH_3$ | $SCH_2COOCH_3$ |
| 1-247 | F | Cl | H | $CF_3$ | $CH_3$ | $SCH_2COOC_2H_5$ |
| 1-248 | F | Cl | H | $CF_3$ | $CH_3$ | $SCH_2COO^nC_3H_7$ |
| 1-249 | F | Cl | H | $CF_3$ | $CH_3$ | $SCH_2COO^nC_4H_9$ |
| 1-250 | F | Cl | H | $CF_3$ | $CH_3$ | $SCH_2COO^nC_5H_{11}$ |
| 1-251 | F | Cl | H | $CF_3$ | $CH_3$ | $SCH_2COO^iC_3H_7$ |
| 1-252 | F | Cl | H | $CF_3$ | $CH_3$ | $SCH_2COO^cC_5H_9$ |
| 1-253 | F | Cl | H | $CF_3$ | $CH_3$ | $SCH_2COO^cC_6H_{11}$ |
| 1-254 | F | Cl | H | $CF_3$ | $CH_3$ | $SCH(CH_3)COOCH_3$ |
| 1-255 | F | Cl | H | $CF_3$ | $CH_3$ | $SCH(CH_3)COOC_2H_5$ |
| 1-256 | F | Cl | H | $CF_3$ | $CH_3$ | $SCH(CH_3)COO^nC_3H_7$ |
| 1-257 | F | Cl | H | $CF_3$ | $CH_3$ | $SCH(CH_3)COO^nC_4H_9$ |
| 1-258 | F | Cl | H | $CF_3$ | $CH_3$ | $SCH(CH_3)COO^nC_5H_{11}$ |
| 1-259 | F | Cl | H | $CF_3$ | $CH_3$ | $SCH(CH_3)COO^iC_3H_7$ |
| 1-260 | F | Cl | H | $CF_3$ | $CH_3$ | $SCH(CH_3)COO^cC_5H_9$ |
| 1-261 | F | Cl | H | $CF_3$ | $CH_3$ | $SCH(CH_3)COO^cC_6H_{11}$ |
| 1-262 | F | Cl | H | $CF_3$ | $CH_3$ | $SCH_2CON(CH_3)_2$ |
| 1-263 | F | Cl | H | $CF_3$ | $CH_3$ | $SCH_2CON(C_2H_5)_2$ |
| 1-264 | F | Cl | H | $CF_3$ | $CH_3$ | $SCH_2CON(tetramethylene)$ |
| 1-265 | F | Cl | H | $CF_3$ | $CH_3$ | $SCH_2CON(pentamethylene)$ |
| 1-266 | F | Cl | H | $CF_3$ | $CH_3$ | $SCH_2CON(ethyleneoxyethylene)$ |
| 1-267 | F | Cl | H | $CF_3$ | $CH_3$ | $SCH(CH_3)CON(CH_3)_2$ |
| 1-268 | F | Cl | H | $CF_3$ | $CH_3$ | $SCH(CH_3)CON(C_2H_5)_2$ |
| 1-269 | F | Cl | H | $CF_3$ | $CH_3$ | $SCH(CH_3)CON(tetramethylene)$ |
| 1-270 | F | Cl | H | $CF_3$ | $CH_3$ | $SCH(CH_3)CON(pentamethylene)$ |
| 1-271 | H | F | H | $CF_3$ | $CH_3$ | $SO_2Cl$ |
| 1-272 | H | Cl | H | $CF_3$ | $CH_3$ | $SO_2Cl$ |
| 1-273 | H | Br | H | $CF_3$ | $CH_3$ | $SO_2Cl$ |
| 1-274 | F | F | H | $CF_3$ | $CH_3$ | $SO_2Cl$ |
| 1-275 | F | Cl | H | $CF_3$ | $CH_3$ | $SO_2Cl$ |
| 1-276 | F | Br | H | $CF_3$ | $CH_3$ | $SO_2Cl$ |
| 1-277 | H | Cl | H | $CF_3$ | $CH_3$ | $SO_2OCH_3$ |
| 1-278 | H | Cl | H | $CF_3$ | $CH_3$ | $SO_2OC_2H_5$ |
| 1-279 | H | Cl | H | $CF_3$ | $CH_3$ | $SO_2O^iC_3H_7$ |
| 1-280 | H | Cl | H | $CF_3$ | $CH_3$ | $SO_2OCH_2CH=CH_2$ |
| 1-281 | F | Cl | H | $CF_3$ | $CH_3$ | $SO_2OCH_3$ |
| 1-282 | F | Cl | H | $CF_3$ | $CH_3$ | $SO_2OC_2H_5$ |
| 1-283 | F | Cl | H | $CF_3$ | $CH_3$ | $SO_2O^iC_3H_7$ |
| 1-284 | F | Cl | H | $CF_3$ | $CH_3$ | $SO_2OCH_2CH=CH_2$ |
| 1-285 | H | Cl | H | $CF_3$ | $CH_3$ | $SO_2N(CH_3)_2$ |
| 1-286 | H | Cl | H | $CF_3$ | $CH_3$ | $SO_2N(C_2H_5)_2$ |
| 1-287 | F | Cl | H | $CF_3$ | $CH_3$ | $SO_2N(CH_3)_2$ |
| 1-288 | F | Cl | H | $CF_3$ | $CH_3$ | $SO_2N(C_2H_5)_2$ |
| 1-289 | H | Cl | H | $CF_3$ | $CH_3$ | COOH |
| 1-290 | H | Cl | H | $CF_3$ | $CH_3$ | $COOCH_3$ |
| 1-291 | H | Cl | H | $CF_3$ | $CH_3$ | $COOC_2H_5$ |
| 1-292 | H | Cl | H | $CF_3$ | $CH_3$ | $COO^nC_3H_7$ |
| 1-293 | H | Cl | H | $CF_3$ | $CH_3$ | $COO^n4C_4H_9$ |
| 1-294 | H | Cl | H | $CF_3$ | $CH_3$ | $COO^nC_5H_{11}$ |
| 1-295 | H | Cl | H | $CF_3$ | $CH_3$ | $COO^iC_3H_7$ |
| 1-296 | H | Cl | H | $CF_3$ | $CH_3$ | $COOCH_2CH_2Cl$ |
| 1-297 | H | Cl | H | $CF_3$ | $CH_3$ | $COOCH_2CH_2Br$ |
| 1-298 | H | Cl | H | $CF_3$ | $CH_3$ | $CON(CH_3)_2$ |
| 1-299 | H | Cl | H | $CF_3$ | $CH_3$ | $CONHCH_3$ |
| 1-300 | H | Cl | H | $CF_3$ | $CH_3$ | $CON(C_2H_5)_2$ |
| 1-301 | H | Cl | H | $CF_3$ | $CH_3$ | $CONHC_2H_5$ |
| 1-302 | H | Cl | H | $CF_3$ | $CH_3$ | $COCH_3$ |
| 1-303 | H | Cl | H | $CF_3$ | $CH_3$ | $COC_2H_5$ |
| 1-304 | H | Cl | H | $CF_3$ | $CH_3$ | $COCH_2Cl$ |
| 1-305 | H | Cl | H | $CF_3$ | $CH_3$ | CHO |
| 1-306 | H | Cl | H | $CF_3$ | $CH_3$ | $CH=CHCOOCH_3$ |
| 1-307 | H | Cl | H | $CF_3$ | $CH_3$ | $CH=CHCOOC_2H_5$ |
| 1-308 | H | Cl | H | $CF_3$ | $CH_3$ | $CH_2CH_2COOCH_3$ |
| 1-309 | H | Cl | H | $CF_3$ | $CH_3$ | $CH_2CH_2COOC_2H_5$ |
| 1-310 | F | Cl | H | $CF_3$ | $CH_3$ | COOH |
| 1-311 | F | Cl | H | $CF_3$ | $CH_3$ | $COOCH_3$ |
| 1-312 | F | Cl | H | $CF_3$ | $CH_3$ | $COOC_2H_5$ |
| 1-313 | F | Cl | H | $CF_3$ | $CH_3$ | $COO^nC_3H_7$ |

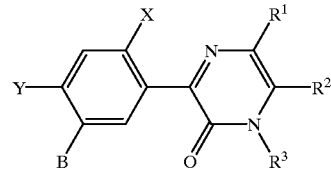

TABLE 1-continued

Compounds of the formula:

(structure: phenyl with X, Y, B substituents connected to pyrimidinone ring with $R^1$, $R^2$, $R^3$)

| Compound No. | X | Y | $R^1$ | $R^2$ | $R^3$ | B |
|---|---|---|---|---|---|---|
| 1-314 | F | Cl | H | $CF_3$ | $CH_3$ | $COO^nC_4H_9$ |
| 1-315 | F | Cl | H | $CF_3$ | $CH_3$ | $COO^nC_5H_{11}$ |
| 1-316 | F | Cl | H | $CF_3$ | $CH_3$ | $COO^iC_3H_7$ |
| 1-317 | F | Cl | H | $CF_3$ | $CH_3$ | $COOCH_2CH_2Cl$ |
| 1-318 | F | Cl | H | $CF_3$ | $CH_3$ | $COOCH_2CH_2Br$ |
| 1-319 | F | Cl | H | $CF_3$ | $CH_3$ | $CON(CH_3)_2$ |
| 1-320 | F | Cl | H | $CF_3$ | $CH_3$ | $CONHCH_3$ |
| 1-321 | F | Cl | H | $CF_3$ | $CH_3$ | $CON(C_2H_5)_2$ |
| 1-322 | F | Cl | H | $CF_3$ | $CH_3$ | $CONHC_2H_5$ |
| 1-323 | F | Cl | H | $CF_3$ | $CH_3$ | $COCH_3$ |
| 1-324 | F | Cl | H | $CF_3$ | $CH_3$ | $COC_2H_5$ |
| 1-325 | F | Cl | H | $CF_3$ | $CH_3$ | $COCH_2Cl$ |
| 1-326 | F | Cl | H | $CF_3$ | $CH_3$ | $CHO$ |
| 1-327 | F | Cl | H | $CF_3$ | $CH_3$ | $CH=CHCOOCH_3$ |
| 1-328 | F | Cl | H | $CF_3$ | $CH_3$ | $CH=CHCOOC_2H_5$ |
| 1-329 | F | Cl | H | $CF_3$ | $CH_3$ | $CH_2CH_2COOCH_3$ |
| 1-330 | F | Cl | H | $CF_3$ | $CH_3$ | $CH_2CH_2COOC_2H_5$ |
| 1-331 | Cl | Cl | H | $CF_3$ | $C_2H_5$ | H |
| 1-332 | Cl | Cl | H | $CF_3$ | $CH_3$ | H |
| 1-333 | Cl | Cl | H | $CF_3$ | $CH_3$ | $NO_2$ |
| 1-334 | Cl | Cl | H | $CF_3$ | $CH_3$ | $NH_2$ |
| 1-335 | Cl | Cl | H | $CF_3$ | $CH_3$ | $NHCH(CH_3)COOCH_3$ |
| 1-336 | Cl | Cl | H | $CF_3$ | $CH_3$ | $NHCH(CH_3)COOC_2H_5$ |
| 1-337 | Cl | Cl | H | $CF_3$ | $CH_3$ | $NHCH(CH_3)COO^nC_3H_7$ |
| 1-338 | Cl | Cl | H | $CF_3$ | $CH_3$ | $NHCH(CH_3)COO^nC_4H_9$ |
| 1-339 | Cl | Cl | H | $CF_3$ | $CH_3$ | $NHCH(CH_3)COO^nC_5H_{11}$ |
| 1-340 | Cl | Cl | H | $CF_3$ | $CH_3$ | $NHCH(CH_3)COO^iC_3H_7$ |
| 1-341 | Cl | Cl | H | $CF_3$ | $CH_3$ | $NHCH(CH_3)COO^cC_5H_9$ |
| 1-342 | Cl | Cl | H | $CF_3$ | $CH_3$ | $NHCH(CH_3)COO^cC_6H_{11}$ |
| 1-343 | Cl | Cl | H | $CF_3$ | $CH_3$ | $NHSO_2CH_3$ |
| 1-344 | Cl | Cl | H | $CF_3$ | $CH_3$ | $NHSO_2C_2H_5$ |
| 1-345 | Cl | Cl | H | $CF_3$ | $CH_3$ | $NHCOOCH_3$ |
| 1-346 | Cl | Cl | H | $CF_3$ | $CH_3$ | $NHCOOC_2H_5$ |
| 1-347 | Cl | Cl | H | $CF_3$ | $CH_3$ | $NHCOO^nC_3H_7$ |
| 1-348 | Cl | Cl | H | $CF_3$ | $CH_3$ | $NHCOO^iC_3H_7$ |
| 1-349 | Cl | Cl | H | $CF_3$ | $CH_3$ | $NHCOO^nC_4H_9$ |
| 1-350 | Cl | Cl | H | $CF_3$ | $CH_3$ | $NHCOO^nC_5H_{11}$ |
| 1-351 | Cl | Cl | H | $CF_3$ | $CH_3$ | $N(CH_2C\equiv CH)COOC_2H_5$ |
| 1-352 | Cl | Cl | H | $CF_3$ | $CH_3$ | $NHCH_2C\equiv CH$ |
| 1-353 | Cl | Cl | H | $CF_3$ | $CH_3$ | $NHCH(CH_3)C\equiv CH$ |
| 1-354 | H | F | H | $CF_3$ | $CH_3$ | $NHCH(CH_3)COOCH_3$ |
| 1-355 | H | F | H | $CF_3$ | $CH_3$ | $NHCH(CH_3)COOC_2H_5$ |
| 1-356 | F | Cl | H | $CF_3$ | $CH_3$ | $OCH_2COO^iC_4H_9$ |
| 1-357 | Cl | Cl | H | $CF_3$ | $CH_3$ | OH |
| 1-358 | Cl | Cl | H | $CF_3$ | $CH_3$ | $OCH_3$ |
| 1-359 | Cl | Cl | H | $CF_3$ | $CH_3$ | $OC_2H_5$ |
| 1-360 | Cl | Cl | H | $CF_3$ | $CH_3$ | $O^iC_3H_7$ |
| 1-361 | Cl | Cl | H | $CF_3$ | $CH_3$ | $O^nC_3H_7$ |
| 1-362 | Cl | Cl | H | $CF_3$ | $CH_3$ | $OCH_2CH_2Cl$ |
| 1-363 | Cl | Cl | H | $CF_3$ | $CH_3$ | $OCF_2CF_2H$ |
| 1-364 | Cl | Cl | H | $CF_3$ | $CH_3$ | $O^cC_5H_9$ |
| 1-365 | Cl | Cl | H | $CF_3$ | $CH_3$ | $O^cC_6H_{11}$ |
| 1-366 | Cl | Cl | H | $CF_3$ | $CH_3$ | $OCH_2CH=CH_2$ |
| 1-367 | Cl | Cl | H | $CF_3$ | $CH_3$ | $OCH_2CCl=CH_2$ |
| 1-368 | Cl | Cl | H | $CF_3$ | $CH_3$ | $OCH_2CCl=CHCl$ |
| 1-369 | Cl | Cl | H | $CF_3$ | $CH_3$ | $OCH(CH_3)CH=CH_2$ |
| 1-370 | Cl | Cl | H | $CF_3$ | $CH_3$ | $OCH_2C\equiv CH$ |
| 1-371 | Cl | Cl | H | $CF_3$ | $CH_3$ | $OCH(CH_3)C\equiv CH$ |
| 1-372 | Cl | Cl | H | $CF_3$ | $CH_3$ | $OCH_2C\equiv CBr$ |
| 1-373 | Cl | Cl | H | $CF_3$ | $CH_3$ | $OCH_2C\equiv CCl$ |
| 1-374 | Cl | Cl | H | $CF_3$ | $CH_3$ | $OCH_2C\equiv CCH_2Cl$ |
| 1-375 | Cl | Cl | H | $CF_3$ | $CH_3$ | $OCH_2CN$ |
| 1-376 | Cl | Cl | H | $CF_3$ | $CH_3$ | $OCH_2OCH_3$ |
| 1-377 | Cl | Cl | H | $CF_3$ | $CH_3$ | $OCH_2OC_2H_5$ |
| 1-378 | Cl | Cl | H | $CF_3$ | $CH_3$ | $OCH_2SCH_3$ |
| 1-379 | Cl | Cl | H | $CF_3$ | $CH_3$ | $OCH_2COOCH_3$ |
| 1-380 | Cl | Cl | H | $CF_3$ | $CH_3$ | $OCH_2COOC_2H_5$ |
| 1-381 | Cl | Cl | H | $CF_3$ | $CH_3$ | $OCH_2COO^nC_3H_7$ |
| 1-382 | Cl | Cl | H | $CF_3$ | $CH_3$ | $OCH_2COO^nC_4H_9$ |
| 1-383 | Cl | Cl | H | $CF_3$ | $CH_3$ | $OCH_2COO^nC_5H_{11}$ |
| 1-384 | Cl | Cl | H | $CF_3$ | $CH_3$ | $OCH_2COO^iC_3H_7$ |
| 1-385 | Cl | Cl | H | $CF_3$ | $CH_3$ | $OCH_2COO^cC_5H_9$ |
| 1-386 | Cl | Cl | H | $CF_3$ | $CH_3$ | $OCH_2COO^cC_6H_{11}$ |
| 1-387 | Cl | Cl | H | $CF_3$ | $CH_3$ | $OCH(CH_3)COOCH_3$ |
| 1-388 | Cl | Cl | H | $CF_3$ | $CH_3$ | $OCH(CH_3)COOC_2H_5$ |
| 1-389 | Cl | Cl | H | $CF_3$ | $CH_3$ | $OCH(CH_3)COO^nC_3H_7$ |
| 1-390 | Cl | Cl | H | $CF_3$ | $CH_3$ | $OCH(CH_3)COO^nC_4H_9$ |
| 1-391 | Cl | Cl | H | $CF_3$ | $CH_3$ | $OCH(CH_3)COO^nC_5H_{11}$ |
| 1-392 | Cl | Cl | H | $CF_3$ | $CH_3$ | $OCH(CH_3)COO^iC_3H_7$ |
| 1-393 | Cl | Cl | H | $CF_3$ | $CH_3$ | $OCH(CH_3)COO^cC_5H_9$ |
| 1-394 | Cl | Cl | H | $CF_3$ | $CH_3$ | $OCH(CH_3)COO^cC_6H_{11}$ |
| 1-395 | Cl | Cl | H | $CF_3$ | $CH_3$ | $OCH_2CON(CH_3)_2$ |
| 1-396 | Cl | Cl | H | $CF_3$ | $CH_3$ | $OCH_2CON(C_2H_5)_2$ |
| 1-397 | Cl | Cl | H | $CF_3$ | $CH_3$ | $OCH_2CON(CH_3)C_2H_5$ |
| 1-398 | Cl | Cl | H | $CF_3$ | $CH_3$ | $OCH(CH_3)CON(CH_3)_2$ |
| 1-399 | Cl | Cl | H | $CF_3$ | $CH_3$ | $OCH(CH_3)CON(C_2H_5)_2$ |
| 1-400 | Cl | Cl | H | $CF_3$ | $CH_3$ | $OCH(CH_3)CON(CH_3)C_2H_5$ |
| 1-401 | Cl | Cl | H | $CF_3$ | $CH_3$ | $OCH_2COON(CH_3)_2$ |
| 1-402 | Cl | Cl | H | $CF_3$ | $CH_3$ | $OCH_2COON(C_2H_5)_2$ |
| 1-403 | Cl | Cl | H | $CF_3$ | $CH_3$ | $OCH(CH_3)COON(CH_3)_2$ |
| 1-404 | Cl | Cl | H | $CF_3$ | $CH_3$ | $OCH(CH_3)COON(C_2H_5)_2$ |
| 1-405 | H | Cl | H | $CF_3$ | $CH_3$ | $CH_2CHClCOOCH_3$ |
| 1-406 | H | Cl | H | $CF_3$ | $CH_3$ | $CH_2CHClCOOC_2H_5$ |
| 1-407 | H | Cl | H | $CF_3$ | $CH_3$ | $CH_2CHClCOO^nC_3H_7$ |
| 1-408 | H | Cl | H | $CF_3$ | $CH_3$ | $CH_2CHBrCOOCH_3$ |
| 1-409 | H | Cl | H | $CF_3$ | $CH_3$ | $CH_2CHBrCOOC_2H_5$ |
| 1-410 | H | Cl | H | $CF_3$ | $CH_3$ | $CH_2CHBrCOO^nC_3H_7$ |
| 1-411 | F | Cl | H | $CF_3$ | $CH_3$ | $CH_2CHClCOOCH_3$ |
| 1-412 | F | Cl | H | $CF_3$ | $CH_3$ | $CH_2CHClCOOC_2H_5$ |
| 1-413 | F | Cl | H | $CF_3$ | $CH_3$ | $CH_2CHClCOO^nC_3H_7$ |
| 1-414 | F | Cl | H | $CF_3$ | $CH_3$ | $CH_2CHBrCOOCH_3$ |
| 1-415 | F | Cl | H | $CF_3$ | $CH_3$ | $CH_2CHBrCOOC_2H_5$ |
| 1-416 | F | Cl | H | $CF_3$ | $CH_3$ | $CH_2CHBrCOO^nC_3H_7$ |
| 1-417 | Cl | Cl | H | $CF_3$ | $CH_3$ | $CH_2CHClCOOCH_3$ |
| 1-418 | Cl | Cl | H | $CF_3$ | $CH_3$ | $CH_2CHClCOOC_2H_5$ |
| 1-419 | Cl | Cl | H | $CF_3$ | $CH_3$ | $CH_2CHClCOO^nC_3H_7$ |
| 1-420 | Cl | Cl | H | $CF_3$ | $CH_3$ | $CH_2CHBrCOOCH_3$ |
| 1-421 | Cl | Cl | H | $CF_3$ | $CH_3$ | $CH_2CHBrCOOC_2H_5$ |
| 1-422 | Cl | Cl | H | $CF_3$ | $CH_3$ | $CH_2CHBrCOO^nC_3H_7$ |
| 1-423 | Cl | Cl | H | $CF_3$ | $CH_3$ | COOH |
| 1-424 | Cl | Cl | H | $CF_3$ | $CH_3$ | $COOCH_3$ |
| 1-425 | Cl | Cl | H | $CF_3$ | $CH_3$ | $COOC_2H_5$ |
| 1-426 | Cl | Cl | H | $CF_3$ | $CH_3$ | $COO^nC_3H_7$ |
| 1-427 | Cl | Cl | H | $CF_3$ | $CH_3$ | $COO^nC_4H_9$ |
| 1-428 | Cl | Cl | H | $CF_3$ | $CH_3$ | $COO^nC_5H_{11}$ |
| 1-429 | Cl | Cl | H | $CF_3$ | $CH_3$ | $COO^iC_3H_7$ |
| 1-430 | Cl | Cl | H | $CF_3$ | $CH_3$ | $COOCH_2CH_2Cl$ |
| 1-431 | Cl | Cl | H | $CF_3$ | $CH_3$ | $COOCH_2CH_2Br$ |
| 1-432 | Cl | Cl | H | $CF_3$ | $CH_3$ | $CON(CH_3)_2$ |
| 1-433 | Cl | Cl | H | $CF_3$ | $CH_3$ | $CONHCH_3$ |
| 1-434 | Cl | Cl | H | $CF_3$ | $CH_3$ | $CON(C_2H_5)_2$ |
| 1-435 | Cl | Cl | H | $CF_3$ | $CH_3$ | $CONHC_2H_5$ |
| 1-436 | Cl | Cl | H | $CF_3$ | $CH_3$ | $COCH_3$ |
| 1-437 | Cl | Cl | H | $CF_3$ | $CH_3$ | $COC_2H_5$ |
| 1-438 | Cl | Cl | H | $CF_3$ | $CH_3$ | $COCH_2Cl$ |
| 1-439 | Cl | Cl | H | $CF_3$ | $CH_3$ | CHO |

TABLE 1-continued

Compounds of the formula:

[Structure: phenyl ring with X, Y, B substituents connected to a pyrazinone ring with R¹, R², R³ substituents]

| Compound No. | X | Y | R¹ | R² | R³ | B |
|---|---|---|---|---|---|---|
| 1-440 | Cl | Cl | H | CF₃ | CH₃ | CH=CHCOOCH₃ |
| 1-441 | Cl | Cl | H | CF₃ | CH₃ | CH=CHCOOC₂H₅ |
| 1-442 | Cl | Cl | H | CF₃ | CH₃ | CH₂CH₂COOCH₃ |
| 1-443 | Cl | Cl | H | CF₃ | CH₃ | CH₂CH₂COOC₂H₅ |
| 1-444 | F | F | CH₃ | CF₃ | CH₃ | H |
| 1-445 | F | F | CH₃ | CF₃ | CH₃ | NO₂ |
| 1-446 | F | F | CH₃ | CF₃ | CH₃ | NH₂ |
| 1-447 | F | Cl | CH₃ | CF₃ | CH₃ | H |
| 1-448 | F | Cl | CH₃ | CF₃ | CH₃ | NO₂ |
| 1-449 | F | Cl | CH₃ | CF₃ | CH₃ | NH₂ |
| 1-450 | F | Cl | CH₃ | CF₃ | CH₃ | NHCH(CH₃)COOCH₃ |
| 1-451 | F | Cl | CH₃ | CF₃ | CH₃ | NHCH(CH₃)COOC₂H₅ |
| 1-452 | F | Cl | CH₃ | CF₃ | CH₃ | NHCH(CH₃)COOⁿC₃H₇ |
| 1-453 | F | Cl | CH₃ | CF₃ | CH₃ | NHCH(CH₃)COOⁿC₄H₉ |
| 1-454 | F | Cl | CH₃ | CF₃ | CH₃ | NHCH(CH₃)COOⁿC₅H₁₁ |
| 1-455 | F | Cl | CH₃ | CF₃ | CH₃ | NHCH(CH₃)COOⁱC₃H₇ |
| 1-456 | F | Cl | CH₃ | CF₃ | CH₃ | NHCH₃ |
| 1-457 | F | Cl | CH₃ | CF₃ | CH₃ | NHC₂H₅ |
| 1-458 | F | Cl | CH₃ | CF₃ | CH₃ | NHCH₂CH=CH₂ |
| 1-459 | F | Cl | CH₃ | CF₃ | CH₃ | NHCH₂C≡CH |
| 1-460 | F | Cl | CH₃ | CF₃ | CH₃ | NHCH₂COOCH₃ |
| 1-461 | F | Cl | CH₃ | CF₃ | CH₃ | NHCH₂COOC₂H₅ |
| 1-462 | F | Cl | CH₃ | CF₃ | CH₃ | NHCH(CH₃)C≡CH |
| 1-463 | F | Cl | CH₃ | CF₃ | CH₃ | NHCOOCH₃ |
| 1-464 | F | Cl | CH₃ | CF₃ | CH₃ | NHCOOC₂H₅ |
| 1-465 | F | Cl | CH₃ | CF₃ | CH₃ | NHSO₂CH₃ |
| 1-466 | F | Cl | CH₃ | CF₃ | CH₃ | NHSO₂C₂H₅ |
| 1-467 | F | Cl | CH₃ | CF₃ | CH₃ | NHSO₂CH₂Cl |
| 1-468 | F | Cl | CH₃ | CF₃ | CH₃ | NHSO₂CF₃ |
| 1-469 | F | Cl | CH₃ | CF₃ | CH₃ | OH |
| 1-470 | F | Cl | CH₃ | CF₃ | CH₃ | OCH₃ |
| 1-471 | F | Cl | CH₃ | CF₃ | CH₃ | OC₂H₅ |
| 1-472 | F | Cl | CH₃ | CF₃ | CH₃ | OⁱC₃H₇ |
| 1-473 | F | Cl | CH₃ | CF₃ | CH₃ | OᶜC₅H₉ |
| 1-474 | F | Cl | CH₃ | CF₃ | CH₃ | OCH₂CH=CH₂ |
| 1-475 | F | Cl | CH₃ | CF₃ | CH₃ | OCH₂C(CH₃)CH=CH₂ |
| 1-476 | F | Cl | CH₃ | CF₃ | CH₃ | OCH₂C≡CH |
| 1-477 | F | Cl | CH₃ | CF₃ | CH₃ | OCH(CH₃)C≡CH |
| 1-478 | F | Cl | CH₃ | CF₃ | CH₃ | OCH₂COOCH₃ |
| 1-479 | F | Cl | CH₃ | CF₃ | CH₃ | OCH₂COOC₂H₅ |
| 1-480 | F | Cl | CH₃ | CF₃ | CH₃ | OCH₂COOⁿC₃H₇ |
| 1-481 | F | Cl | CH₃ | CF₃ | CH₃ | OCH₂COOⁿC₄H₉ |
| 1-482 | F | Cl | CH₃ | CF₃ | CH₃ | OCH₂COOⁿC₅H₁₁ |
| 1-483 | F | Cl | CH₃ | CF₃ | CH₃ | OCH₂COOⁱC₃H₇ |
| 1-484 | F | Cl | CH₃ | CF₃ | CH₃ | OCH(CH₃)COOCH₃ |
| 1-485 | F | Cl | CH₃ | CF₃ | CH₃ | OCH(CH₃)COOC₂H₅ |
| 1-486 | F | Cl | CH₃ | CF₃ | CH₃ | OCH(CH₃)COOⁿC₃H₇ |
| 1-487 | F | Cl | CH₃ | CF₃ | CH₃ | OCH(CH₃)COOⁿC₄H₉ |
| 1-488 | F | Cl | CH₃ | CF₃ | CH₃ | OCH(CH₃)COOⁿC₅H₁₁ |
| 1-489 | F | Cl | CH₃ | CF₃ | CH₃ | OCH(CH₃)COOⁱC₃H₇ |
| 1-490 | F | Cl | CH₃ | CF₃ | CH₃ | COOH |
| 1-491 | F | Cl | CH₃ | CF₃ | CH₃ | COOCH₃ |
| 1-492 | F | Cl | CH₃ | CF₃ | CH₃ | COOC₂H₅ |
| 1-493 | F | Cl | CH₃ | CF₃ | CH₃ | COOⁿC₃H₇ |
| 1-494 | F | Cl | CH₃ | CF₃ | CH₃ | COOⁿC₄H₉ |
| 1-495 | F | Cl | CH₃ | CF₃ | CH₃ | COOⁿC₅H₁₁ |
| 1-496 | F | Cl | CH₃ | CF₃ | CH₃ | COOⁱC₃H₇ |
| 1-497 | F | Cl | CH₃ | CF₃ | CH₃ | COOCH₂CH₂Cl |
| 1-498 | F | Cl | CH₃ | CF₃ | CH₃ | COOCH₂CH₂Br |
| 1-499 | F | Cl | CH₃ | CF₃ | CH₃ | CON(CH₃)₂ |
| 1-500 | F | Cl | CH₃ | CF₃ | CH₃ | CONHCH₃ |
| 1-501 | F | Cl | CH₃ | CF₃ | CH₃ | CON(C₂H₅)₂ |
| 1-502 | F | Cl | CH₃ | CF₃ | CH₃ | CONHC₂H₅ |
| 1-503 | F | Cl | CH₃ | CF₃ | CH₃ | COCH₃ |
| 1-504 | F | Cl | CH₃ | CF₃ | CH₃ | COC₂H₅ |
| 1-505 | F | Cl | CH₃ | CF₃ | CH₃ | COCH₂Cl |
| 1-506 | F | Cl | CH₃ | CF₃ | CH₃ | CHO |
| 1-507 | F | Cl | CH₃ | CF₃ | CH₃ | CH=CHCOOCH₃ |
| 1-508 | F | Cl | CH₃ | CF₃ | CH₃ | CH=CHCOOC₂H₅ |
| 1-509 | F | Cl | CH₃ | CF₃ | CH₃ | CH₂CH₂COOCH₃ |
| 1-510 | F | Cl | CH₃ | CF₃ | CH₃ | CH₂CH₂COOC₂H₅ |
| 1-511 | F | Cl | CH₃ | CF₃ | CH₃ | CH₂CHClCOOCH₃ |
| 1-512 | F | Cl | CH₃ | CF₃ | CH₃ | CH₂CHClCOOC₂H₅ |
| 1-513 | F | Cl | CH₃ | CF₃ | CH₃ | CH₂CHBrCOOCH₃ |
| 1-514 | F | Cl | CH₃ | CF₃ | CH₃ | CH₂CHBrCOOC₂H₅ |
| 1-515 | Cl | Cl | CH₃ | CF₃ | CH₃ | H |
| 1-516 | Cl | Cl | CH₃ | CF₃ | CH₃ | NO₂ |
| 1-517 | Cl | Cl | CH₃ | CF₃ | CH₃ | NH₂ |
| 1-518 | Cl | Cl | CH₃ | CF₃ | CH₃ | NHCH(CH₃)COOCH₃ |
| 1-519 | Cl | Cl | CH₃ | CF₃ | CH₃ | NHCH(CH₃)COOC₂H₅ |
| 1-520 | Cl | Cl | CH₃ | CF₃ | CH₃ | NHCH(CH₃)COOⁿC₃H₇ |
| 1-521 | Cl | Cl | CH₃ | CF₃ | CH₃ | NHCH(CH₃)COOⁿC₄H₉ |
| 1-522 | Cl | Cl | CH₃ | CF₃ | CH₃ | NHCH(CH₃)COOⁿC₅H₁₁ |
| 1-523 | Cl | Cl | CH₃ | CF₃ | CH₃ | NHCH(CH₃)COOⁱC₃H₇ |
| 1-524 | Cl | Cl | CH₃ | CF₃ | CH₃ | NHCH₃ |
| 1-525 | Cl | Cl | CH₃ | CF₃ | CH₃ | NHC₂H₅ |
| 1-526 | Cl | Cl | CH₃ | CF₃ | CH₃ | NHCH₂CH=CH₂ |
| 1-527 | Cl | Cl | CH₃ | CF₃ | CH₃ | NHCH₂C≡CH |
| 1-528 | Cl | Cl | CH₃ | CF₃ | CH₃ | NHCH₂COOCH₃ |
| 1-529 | Cl | Cl | CH₃ | CF₃ | CH₃ | NHCH₂COOC₂H₅ |
| 1-530 | Cl | Cl | CH₃ | CF₃ | CH₃ | NHCH(CH₃)C≡CH |
| 1-531 | Cl | Cl | CH₃ | CF₃ | CH₃ | NHCOOCH₃ |
| 1-532 | Cl | Cl | CH₃ | CF₃ | CH₃ | NHCOOC₂H₅ |
| 1-533 | Cl | Cl | CH₃ | CF₃ | CH₃ | NHSO₂CH₃ |
| 1-534 | Cl | Cl | CH₃ | CF₃ | CH₃ | NHSO₂C₂H₅ |
| 1-535 | Cl | Cl | CH₃ | CF₃ | CH₃ | NHSO₂CH₂Cl |
| 1-536 | Cl | Cl | CH₃ | CF₃ | CH₃ | NHSO₂CF₃ |
| 1-537 | Cl | Cl | CH₃ | CF₃ | CH₃ | OH |
| 1-538 | Cl | Cl | CH₃ | CF₃ | CH₃ | OCH₃ |
| 1-539 | Cl | Cl | CH₃ | CF₃ | CH₃ | OC₂H₅ |
| 1-540 | Cl | Cl | CH₃ | CF₃ | CH₃ | OⁱC₃H₇ |
| 1-541 | Cl | Cl | CH₃ | CF₃ | CH₃ | OCH₂CH=CH₂ |
| 1-542 | Cl | Cl | CH₃ | CF₃ | CH₃ | OCH₂C(CH₃)CH=CH₂ |
| 1-543 | Cl | Cl | CH₃ | CF₃ | CH₃ | OCH₂C≡CH |
| 1-544 | Cl | Cl | CH₃ | CF₃ | CH₃ | OCH(CH₃)C≡CH |
| 1-545 | Cl | Cl | CH₃ | CF₃ | CH₃ | OCH₂COOCH₃ |
| 1-546 | Cl | Cl | CH₃ | CF₃ | CH₃ | OCH₂COOC₂H₅ |
| 1-547 | Cl | Cl | CH₃ | CF₃ | CH₃ | OCH₂COOⁿC₃H₇ |
| 1-548 | Cl | Cl | CH₃ | CF₃ | CH₃ | OCH₂COOⁿC₄H₉ |
| 1-549 | Cl | Cl | CH₃ | CF₃ | CH₃ | OCH₂COOⁿC₅H₁₁ |
| 1-550 | Cl | Cl | CH₃ | CF₃ | CH₃ | OCH₂COOⁱC₃H₇ |
| 1-551 | Cl | Cl | CH₃ | CF₃ | CH₃ | OCH(CH₃)COOCH₃ |
| 1-552 | Cl | Cl | CH₃ | CF₃ | CH₃ | OCH(CH₃)COOC₂H₅ |
| 1-553 | Cl | Cl | CH₃ | CF₃ | CH₃ | OCH(CH₃)COOⁿC₃H₇ |
| 1-554 | Cl | Cl | CH₃ | CF₃ | CH₃ | OCH(CH₃)COOⁿC₄H₉ |
| 1-555 | Cl | Cl | CH₃ | CF₃ | CH₃ | OCH(CH₃)COOⁿC₅H₁₁ |
| 1-556 | Cl | Cl | CH₃ | CF₃ | CH₃ | OCH(CH₃)COOⁱC₃H₇ |
| 1-557 | Cl | Cl | CH₃ | CF₃ | CH₃ | COOH |
| 1-558 | Cl | Cl | CH₃ | CF₃ | CH₃ | COOCH₃ |
| 1-559 | Cl | Cl | CH₃ | CF₃ | CH₃ | COOC₂H₅ |
| 1-560 | Cl | Cl | CH₃ | CF₃ | CH₃ | COOⁿC₃H₇ |
| 1-561 | Cl | Cl | CH₃ | CF₃ | CH₃ | COOⁿC₄H₉ |
| 1-562 | Cl | Cl | CH₃ | CF₃ | CH₃ | COOⁿC₅H₁₁ |
| 1-563 | Cl | Cl | CH₃ | CF₃ | CH₃ | COOⁱC₃H₇ |
| 1-564 | Cl | Cl | CH₃ | CF₃ | CH₃ | COOCH₂CH₂Cl |
| 1-565 | Cl | Cl | CH₃ | CF₃ | CH₃ | COOCH₂CH₂Br |

TABLE 1-continued

Compounds of the formula:

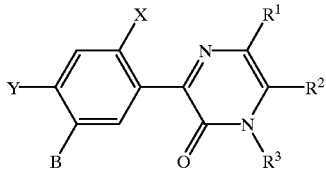

| Compound No. | X | Y | $R^1$ | $R^2$ | $R^3$ | B |
|---|---|---|---|---|---|---|
| 1-566 | Cl | Cl | $CH_3$ | $CF_3$ | $CH_3$ | $CON(CH_3)_2$ |
| 1-567 | Cl | Cl | $CH_3$ | $CF_3$ | $CH_3$ | $CONHCH_3$ |
| 1-568 | Cl | Cl | $CH_3$ | $CF_3$ | $CH_3$ | $CON(C_2H_5)_2$ |
| 1-569 | Cl | Cl | $CH_3$ | $CF_3$ | $CH_3$ | $CONHC_2H_5$ |
| 1-570 | Cl | Cl | $CH_3$ | $CF_3$ | $CH_3$ | $COCH_3$ |
| 1-571 | Cl | Cl | $CH_3$ | $CF_3$ | $CH_3$ | $COC_2H_5$ |
| 1-572 | Cl | Cl | $CH_3$ | $CF_3$ | $CH_3$ | $COCH_2Cl$ |
| 1-573 | Cl | Cl | $CH_3$ | $CF_3$ | $CH_3$ | $CHO$ |
| 1-574 | Cl | Cl | $CH_3$ | $CF_3$ | $CH_3$ | $CH=CHCOOCH_3$ |
| 1-575 | Cl | Cl | $CH_3$ | $CF_3$ | $CH_3$ | $CH=CHCOOC_2H_5$ |
| 1-576 | Cl | Cl | $CH_3$ | $CF_3$ | $CH_3$ | $CH_2CH_2COOCH_3$ |
| 1-577 | Cl | Cl | $CH_3$ | $CF_3$ | $CH_3$ | $CH_2CH_2COOC_2H_5$ |
| 1-578 | Cl | Cl | $CH_3$ | $CF_3$ | $CH_3$ | $CH_2CHClCOOCH_3$ |
| 1-579 | Cl | Cl | $CH_3$ | $CF_3$ | $CH_3$ | $CH_2CHClCOOC_2H_5$ |
| 1-580 | Cl | Cl | $CH_3$ | $CF_3$ | $CH_3$ | $CH_2CHBrCOOCH_3$ |
| 1-581 | Cl | Cl | $CH_3$ | $CF_3$ | $CH_3$ | $CH_2CHBrCOOC_2H_5$ |

TABLE 2

Compounds of the formula:

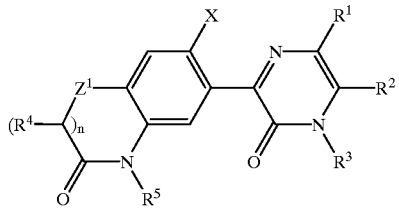

| Compound No | X | $Z^1$ | n | $R^1$ | $R^2$ | $R^3$ | $R^4$ | $R^5$ |
|---|---|---|---|---|---|---|---|---|
| 2-1 | H | O | 1 | H | $CF_3$ | $CH_3$ | H | H |
| 2-2 | H | O | 1 | H | $CF_3$ | $CH_3$ | H | $CH_3$ |
| 2-3 | H | O | 1 | H | $CF_3$ | EH3 | H | $C_2H_5$ |
| 2-4 | H | O | 1 | H | $CF_3$ | EH3 | H | $^nC_3H_7$ |
| 2-5 | H | O | 1 | H | $CF_3$ | $CH_3$ | H | $^iC_3H_7$ |
| 2-6 | H | O | 1 | H | $CF_3$ | $CH_3$ | H | $^iC_4H_9$ |
| 2-7 | H | O | 1 | H | $CF_3$ | $CH_3$ | H | $^nC_4H_9$ |
| 2-8 | H | C | 1 | H | $CF_3$ | $CH_3$ | H | $CH_2CH_2Cl$ |
| 2-9 | H | O | 1 | H | $CF_3$ | $CH_3$ | H | $CH_2CH_2Br$ |
| 2-10 | H | O | 1 | H | $CF_3$ | $CH_3$ | H | $CH_2CH=CH_2$ |
| 2-11 | H | O | 1 | H | $CF_3$ | $CH_3$ | H | $CH(CH_3)CH=CH_2$ |
| 2-12 | H | O | 1 | H | $CF_3$ | $CH_3$ | H | $CH_2CCl=CH_2$ |
| 2-13 | H | O | 1 | H | $CF_3$ | $CH_3$ | H | $CH_2C\equiv CH$ |
| 2-14 | H | O | 1 | H | $CF_3$ | $CH_3$ | H | $CH(CH_3)C\equiv CH$ |
| 2-15 | H | C | 1 | H | $CF_3$ | $CH_3$ | H | $CH_2CN$ |
| 2-16 | H | O | 1 | H | $CF_3$ | $CH_3$ | H | $CH_2OCH_3$ |
| 2-17 | H | O | 1 | H | $CF_3$ | $CH_3$ | H | $CH_2OC_2H_5$ |
| 2-18 | H | O | 1 | H | $CF_3$ | $CH_3$ | H | $CH_2COOH$ |
| 2-19 | H | O | 1 | H | $CF_3$ | $CH_3$ | H | $CH_2COOCH_3$ |
| 2-20 | H | O | 1 | H | $CF_3$ | $CH_3$ | H | $CH_2COOc_2H_5$ |
| 2-21 | H | O | 1 | H | $CF_3$ | $CH_3$ | H | $CH_2COO^nC_3H_7$ |
| 2-22 | H | O | 1 | H | $CF_3$ | $CH_3$ | H | $CH_2COO^nC_4H_9$ |
| 2-23 | H | O | 1 | H | $CF_3$ | $CH_3$ | H | $CH_2COO^nC_5H_{11}$ |
| 2-24 | H | O | 1 | H | $CF_3$ | $CH_3$ | 14 | $CH_2COO^iC_3H_7$ |

TABLE 2-continued

Compounds of the formula:

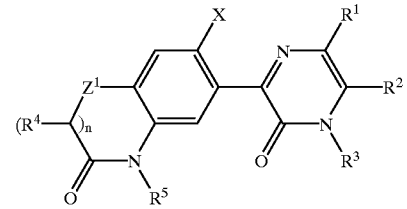

| Compound No | X | $Z^1$ | n | $R^1$ | $R^2$ | $R^3$ | $R^4$ | $R^5$ |
|---|---|---|---|---|---|---|---|---|
| 2-25 | H | O | 1 | H | $CF_3$ | $CH_3$ | H | $CH_2COO^cC_5H_9$ |
| 2-26 | H | O | 1 | H | $CF_3$ | $CH_3$ | H | $CH_2COO^cC_6H_{11}$ |
| 2-27 | H | C | 1 | H | $CF_3$ | $CH_3$ | H | $CH(CH_3)COOH$ |
| 2-28 | H | O | 1 | H | $CF_3$ | $CH_3$ | H | $CH(CH_3)COOCH_3$ |
| 2-29 | H | O | 1 | H | $CF_3$ | $CH_3$ | H | $CH(CH_3)COOC_2H_5$ |
| 2-30 | H | O | 1 | H | $CF_3$ | $CH_3$ | H | $CH(CH_3)COO^nC_3H_7$ |
| 2-31 | H | O | 1 | H | $CF_3$ | $CH_3$ | H | $CH(CH_3)COO^nC_4H_9$ |
| 2-32 | H | O | 1 | H | $CF_3$ | $CH_3$ | H | $CH(CH_3)COO^nC_5H_{11}$ |
| 2-33 | H | O | 1 | H | $CF_3$ | $CH_3$ | H | $CH(CH_3)COO^iC_3H_7$ |
| 2-34 | H | O | 1 | H | $CF_3$ | $CH_3$ | H | $CH(CH_3)COO^cC_5H_9$ |
| 2-35 | H | O | 1 | H | $CF_3$ | $CH_3$ | H | $CH(CH_3)COO^cC_6H_{11}$ |
| 2-36 | H | O | 1 | H | $CF_3$ | $CH_3$ | $CH_3$ | H |
| 2-37 | H | O | 1 | H | $CF_3$ | $CH_3$ | $CH_3$ | $CH_3$ |
| 2-38 | H | O | 1 | H | $CF_3$ | $CH_3$ | $CH_3$ | $C_2H_5$ |
| 2-39 | H | O | 1 | H | $CF_3$ | $CH_3$ | $CH_3$ | $^nC_3H_7$ |
| 2-40 | H | O | 1 | H | $CF_3$ | $CH_3$ | $CH_3$ | $^iC_3H_7$ |
| 2-41 | H | O | 1 | H | $CF_3$ | $CH_3$ | $CH_3$ | $^iC_4H_9$ |
| 2-42 | H | O | 1 | H | $CF_3$ | $CH_3$ | $CH_3$ | $^nC_4H_9$ |
| 2-43 | H | O | 1 | H | $CF_3$ | $CH_3$ | $CH_3$ | $CH_2CH=CH_2$ |
| 2-44 | H | O | 1 | H | $CF_3$ | $CH_3$ | $CH_3$ | $CH(CH_3)CH=CH_2$ |
| 2-45 | H | O | 1 | H | $CF_3$ | $CH_3$ | $CH_3$ | $CH_2C\equiv CH$ |
| 2-46 | H | Q | 1 | H | $CF_3$ | $CH_3$ | $CH_3$ | $CH(CH_3)C\equiv CH$ |
| 2-47 | H | O | 1 | H | $CF_3$ | $CH_3$ | $CH_3$ | $CH_2OCH_3$ |
| 2-48 | H | O | 1 | H | $CF_3$ | $CH_3$ | $CH_3$ | $CH_2OC_2H_5$ |
| 2-49 | F | O | 1 | H | $CF_3$ | $CH_3$ | H | H |
| 2-50 | F | O | 1 | H | $CF_3$ | $CH_3$ | H | $CH_3$ |
| 2-51 | F | O | 1 | H | $CF_3$ | $CH_3$ | H | $C_2H_5$ |
| 2-52 | F | O | 1 | H | $CF_3$ | $CH_3$ | H | $^nC_3H_7$ |
| 2-53 | F | O | 1 | H | $CF_3$ | $CH_3$ | H | $^iC_3H_7$ |
| 2-54 | F | O | 1 | H | $CF_3$ | $CH_3$ | H | $^iC_4H_9$ |
| 2-55 | F | O | 1 | H | $CF_3$ | $CH_3$ | H | $^nC_4H_9$ |
| 2-56 | F | O | 1 | H | $CF_3$ | $CH_3$ | H | $CH_2CH_2Cl$ |
| 2-57 | F | O | 1 | H | $CF_3$ | $CH_3$ | H | $CH_2CH_2Br$ |
| 2-58 | F | O | 1 | H | $CF_3$ | $CH_3$ | H | $CH_2CH=CH_2$ |
| 2-59 | F | O | 1 | H | $CF_3$ | $CH_3$ | H | $CH(CH_3)CH=CH_2$ |
| 2-60 | F | O | 1 | H | $CF_3$ | $CH_3$ | H | $CH_2CCl=CH_2$ |
| 2-61 | F | O | 1 | H | $CF_3$ | $CH_3$ | H | $CH_2C\equiv CH$ |
| 2-62 | F | O | 1 | H | $CF_3$ | $CH_3$ | H | $CH(CH_3)C\equiv CH$ |
| 2-63 | F | O | 1 | H | $CF_3$ | $CH_3$ | H | $CH_2CN$ |
| 2-64 | F | O | 1 | H | $CF_3$ | $CH_3$ | H | $CH_2OCH_3$ |
| 2-65 | F | O | 1 | H | $CF_3$ | $CH_3$ | H | $CH_2OC_2H_5$ |
| 2-66 | F | O | 1 | H | $CF_3$ | $CH_3$ | H | $CH_2COOH$ |
| 2-67 | F | O | 1 | H | $CF_3$ | $CH_3$ | H | $CH_2COOCH_3$ |
| 2-68 | F | O | 1 | H | $CF_3$ | $CH_3$ | H | $CH_2COOC_2H_5$ |
| 2-69 | F | O | 1 | H | $CF_3$ | $CH_3$ | H | $CH_2COO^nC_3H_7$ |
| 2-70 | F | O | 1 | H | $CF_3$ | $CH_3$ | H | $CH_2COO^nC_4H_9$ |
| 2-71 | F | O | 1 | H | $CF_3$ | $CH_3$ | H | $CH_2COO^nC_5H_{11}$ |
| 2-72 | F | O | 1 | H | $CF_3$ | $CH_3$ | H | $CH_2COO^iC_3H_7$ |
| 2-73 | F | O | 1 | H | $CF_3$ | $CH_3$ | H | $CH_2COO^cC_5H_9$ |
| 2-74 | F | O | 1 | H | $CF_3$ | $CH_3$ | H | $CH_2COO^cC_6H_{11}$ |
| 2-75 | F | O | 1 | H | $CF_3$ | $CH_3$ | H | $CH(CH_3)COOH$ |
| 2-76 | F | O | 1 | H | $CF_3$ | $CH_3$ | H | $CH(CH_3)COOCH_3$ |
| 2-77 | F | O | 1 | H | $CF_3$ | $CH_3$ | H | $CH(CH_3)COOC_2H_5$ |
| 2-78 | F | O | 1 | H | $CF_3$ | $CH_3$ | H | $CH(CH_3)COO^nC_3H_7$ |
| 2-79 | F | O | 1 | H | $CF_3$ | $CH_3$ | H | $CH(CH_3)COO^nC_4H_9$ |
| 2-80 | F | O | 1 | H | $CF_3$ | $CH_3$ | H | $CH(CH_3)COO^nC_5H_{11}$ |
| 2-81 | F | O | 1 | H | $CF_3$ | $CH_3$ | H | $CH(CH_3)COO^iC_3H_7$ |
| 2-82 | F | O | 1 | H | $CF_3$ | $CH_3$ | H | $CH(CH_3)COO^cC_5H_9$ |
| 2-83 | F | O | 1 | H | $CF_3$ | $CH_3$ | H | $CH(CH_3)COO^cC_6H_{11}$ |
| 2-84 | F | O | 1 | H | $CF_3$ | $CH_3$ | $CH_3$ | H |
| 2-85 | F | O | 1 | H | $CF_3$ | $CH_3$ | $CH_3$ | $CH_3$ |

TABLE 2-continued

Compounds of the formula:

(structure shown with substituents X, R¹, R², R³, R⁴, R⁵, Z¹, n)

| Compound No | X | Z¹ | n | R¹ | R² | R³ | R⁴ | R⁵ |
|---|---|---|---|---|---|---|---|---|
| 2-86 | F | O | 1 | H | $CF_3$ | $CH_3$ | $CH_3$ | $C_2H_5$ |
| 2-87 | F | O | 1 | H | $CF_3$ | $CH_3$ | $CH_3$ | $^nC_3H_7$ |
| 2-88 | F | O | 1 | H | $CF_3$ | $CH_3$ | $CH_3$ | $^iC_3H_7$ |
| 2-89 | F | O | 1 | H | $CF_3$ | $CH_3$ | $CH_3$ | $^iC_4H_9$ |
| 2-90 | F | O | 1 | H | $CF_3$ | $CH_3$ | $CH_3$ | $^nC_4H_9$ |
| 2-91 | F | O | 1 | H | $CF_3$ | $CH_3$ | $CH_3$ | $CH_2CH=CH_2$ |
| 2-92 | F | O | 1 | H | $CF_3$ | $CH_3$ | $CH_3$ | $CH(CH_3)CH=CH_2$ |
| 2-93 | F | O | 1 | H | $CF_3$ | $CH_3$ | $CH_3$ | $CH_2C\equiv CH$ |
| 2-94 | F | O | 1 | H | $CF_3$ | $CH_3$ | $CH_3$ | $CH(CH_3)C\equiv CH$ |
| 2-95 | F | O | 1 | H | $CF_3$ | $CH_3$ | $CH_3$ | $CH_2OCH_3$ |
| 2-96 | F | O | 1 | H | $CF_3$ | $CH_3$ | $CH_3$ | $CH_2OC_2H_5$ |
| 2-97 | H | S | 0 | H | $CF_3$ | $CH_3$ | — | H |
| 2-98 | H | S | 0 | H | $CF_3$ | $CH_3$ | — | $CH_3$ |
| 2-99 | H | S | 0 | H | $CF_3$ | $CH_3$ | — | $C_2H_5$ |
| 2-100 | H | S | 0 | H | $CF_3$ | $CH_3$ | — | $^nC_3H_7$ |
| 2-101 | H | S | 0 | H | $CF_3$ | $CH_3$ | — | $^nC_4H_9$ |
| 2-102 | H | S | 0 | H | $CF_3$ | $CH_3$ | — | $^iC_3H_7$ |
| 2-103 | H | S | 0 | H | $CF_3$ | $CH_3$ | — | $^iC_4H_9$ |
| 2-104 | H | S | 0 | H | $CF_3$ | $CH_3$ | — | $CH_2CH_2Cl$ |
| 2-105 | H | S | 0 | H | $CF_3$ | $CH_3$ | — | $CH_2CH_2Br$ |
| 2-106 | H | S | 0 | H | $CF_3$ | $CH_3$ | — | $CH_2CH=CH_2$ |
| 2-107 | H | S | 0 | H | $CF_3$ | $CH_3$ | — | $CH(CH_3)CH=CH_2$ |
| 2-108 | H | S | 0 | H | $CF_3$ | $CH_3$ | — | $CH_2CCl=CH_2$ |
| 2-109 | H | S | 0 | H | $CF_3$ | $CH_3$ | — | $CH_2C\equiv CH$ |
| 2-110 | H | S | 0 | H | $CF_3$ | $CH_3$ | — | $CH(CH_3)C\equiv CH$ |
| 2-111 | H | S | 0 | H | $CF_3$ | $CH_3$ | — | $CH_2CN$ |
| 2-112 | H | S | 0 | H | $CF_3$ | $CH_3$ | — | $CH_2OCH_3$ |
| 2-113 | H | S | 0 | H | $CF_3$ | $CH_3$ | — | $CH_2OC_2H_5$ |
| 2-114 | H | S | 0 | H | $CF_3$ | $CH_3$ | — | $CH_2COOH$ |
| 2-115 | H | S | 0 | H | $CF_3$ | $CH_3$ | — | $CH_2COOCH_3$ |
| 2-116 | H | S | 0 | H | $CF_3$ | $CH_3$ | — | $CH_2COOC_2H_5$ |
| 2-117 | H | S | 0 | H | $CF_3$ | $CH_3$ | — | $CH_2COO^nC_3H_7$ |
| 2-118 | H | S | 0 | H | $CF_3$ | $CH_3$ | — | $CH_2COO^nC_4H_9$ |
| 2-119 | H | S | 0 | H | $CF_3$ | $CH_3$ | — | $CH_2COO^nC_5H_{11}$ |
| 2-120 | H | S | 0 | H | $CF_3$ | $CH_3$ | — | $CH_2COO^iC_3H_7$ |
| 2-121 | H | S | 0 | H | $CF_3$ | $CH_3$ | — | $CH_2COO^cC_5H_9$ |
| 2-122 | H | S | 0 | H | $CF_3$ | $CH_3$ | — | $CH_2COO^cC_6H_{11}$ |
| 2-123 | H | S | 0 | H | $CF_3$ | $CH_3$ | — | $CH(CH_3)COOH$ |
| 2-124 | H | S | 0 | H | $CF_3$ | $CH_3$ | — | $CH(CH_3)COOCH_3$ |
| 2-125 | H | S | 0 | H | $CF_3$ | $CH_3$ | — | $CH(CH_3)COOC_2H_5$ |
| 2-126 | H | S | 0 | H | $CF_3$ | $CH_3$ | — | $CH(CH_3)COO^nC_3H_7$ |
| 2-127 | H | S | 0 | H | $CF_3$ | $CH_3$ | — | $CH(CH_3)COO^nC_4H_9$ |
| 2-128 | H | S | 0 | H | $CF_3$ | $CH_3$ | — | $CH(CH_3)COO^nC_5H_{11}$ |
| 2-129 | H | S | 0 | H | $CF_3$ | $CH_3$ | — | $CH(CH_3)COO^iC_3H_7$ |
| 2-130 | H | S | 0 | H | $CF_3$ | $CH_3$ | — | $CH(CH_3)COO^cC_5H_9$ |
| 2-131 | H | S | 0 | H | $CF_3$ | $CH_3$ | — | $CH(CH_3)COO^cC_6H_{11}$ |
| 2-132 | F | S | 0 | H | $CF_3$ | $CH_3$ | — | H |
| 2-133 | F | S | 0 | H | $CF_3$ | $CH_3$ | — | $CH_3$ |
| 2-134 | F | S | 0 | H | $CF_3$ | $CH_3$ | — | $C_2H_5$ |
| 2-135 | F | S | 0 | H | $CF_3$ | $CH_3$ | — | $^nC_3H_7$ |
| 2-136 | F | S | 0 | H | $CF_3$ | $CH_3$ | — | $^nC_4H_9$ |
| 2-137 | F | S | 0 | H | $CF_3$ | $CH_3$ | — | $^iC_3H_7$ |
| 2-138 | F | S | 0 | H | $CF_3$ | $CH_3$ | — | $^iC_4H_9$ |
| 2-139 | F | S | 0 | H | $CF_3$ | $CH_3$ | — | $CH_2CH_2Cl$ |
| 2-140 | F | S | 0 | H | $CF_3$ | $CH_3$ | — | $CH_2CH_2Br$ |
| 2-141 | F | S | 0 | H | $CF_3$ | $CH_3$ | — | $CH_2CH=CH_2$ |
| 2-142 | F | S | 0 | H | $CF_3$ | $CH_3$ | — | $CH(CH_3)CH=CH_2$ |
| 2-143 | F | S | 0 | H | $CF_3$ | $CH_3$ | — | $CH_2CCl=CH_2$ |
| 2-144 | F | S | 0 | H | $CF_3$ | $CH_3$ | — | $CH_2C\equiv CH$ |
| 2-145 | F | S | 0 | H | $CF_3$ | $CH_3$ | — | $CH(CH_3)C\equiv CH$ |
| 2-146 | F | S | 0 | H | $CF_3$ | $CH_3$ | — | $CH_2CN$ |
| 2-147 | F | S | 0 | H | $CF_3$ | $CH_3$ | — | $CH_2OCH_3$ |
| 2-148 | F | S | 0 | H | $CF_3$ | $CH_3$ | — | $CH_2OC_2H_5$ |
| 2-149 | F | S | 0 | H | $CF_3$ | $CH_3$ | — | $CH_2COOH$ |
| 2-150 | F | S | 0 | H | $CF_3$ | $CH_3$ | — | $CH_2COOCH_3$ |
| 2-151 | F | S | 0 | H | $CF_3$ | $CH_3$ | — | $CH_2COOC_2H_5$ |
| 2-152 | F | S | 0 | H | $CF_3$ | $CH_3$ | — | $CH_2COO^nC_3H_7$ |
| 2-153 | F | S | 0 | H | $CF_3$ | $CH_3$ | — | $CH_2COO^nC_4H_9$ |
| 2-154 | F | S | 0 | H | $CF_3$ | $CH_3$ | — | $CH_2COO^nC_5H_{11}$ |
| 2-155 | F | S | 0 | H | $CF_3$ | $CH_3$ | — | $CH_2COO^iC_3H_7$ |
| 2-156 | F | S | 0 | H | $CF_3$ | $CH_3$ | — | $CH_2COO^cC_5H_9$ |
| 2-157 | F | S | 0 | H | $CF_3$ | $CH_3$ | — | $CH_2COO^cC_6H_{11}$ |
| 2-158 | F | S | 0 | H | $CF_3$ | $CH_3$ | — | $CH(CH_3)COOH$ |
| 2-159 | F | S | 0 | H | $CF_3$ | $CH_3$ | — | $CH(CH_3)COOCH_3$ |
| 2-160 | F | S | 0 | H | $CF_3$ | $CH_3$ | — | $CH(CH_3)COOC_2H_5$ |
| 2-161 | F | S | 0 | H | $CF_3$ | $CH_3$ | — | $CH(CH_3)COO^nC_3H_7$ |
| 2-162 | F | S | 0 | H | $CF_3$ | $CH_3$ | — | $CH(CH_3)COO^nC_4H_9$ |
| 2-163 | F | S | 0 | H | $CF_3$ | $CH_3$ | — | $CH(CH_3)COO^nC_5H_{11}$ |
| 2-164 | F | S | 0 | H | $CF_3$ | $CH_3$ | — | $CH(CH_3)COO^iC_3H_7$ |
| 2-165 | F | S | 0 | H | $CF_3$ | $CH_3$ | — | $CH(CH_3)COO^cC_5H_9$ |
| 2-166 | F | S | 0 | H | $CF_3$ | $CH_3$ | — | $CH(CH_3)COO^cC_6H_{11}$ |
| 2-167 | H | O | 0 | H | $CF_3$ | $CH_3$ | — | H |
| 2-168 | H | O | 0 | H | $CF_3$ | $CH_3$ | — | $CH_3$ |
| 2-169 | H | O | 0 | H | $CF_3$ | $CH_3$ | — | $C_2H_5$ |
| 2-170 | H | O | 0 | H | $CF_3$ | $CH_3$ | — | $^nC_3H_7$ |
| 2-171 | H | O | 0 | H | $CF_3$ | $CH_3$ | — | $^nC_4H_9$ |
| 2-172 | H | O | 0 | H | $CF_3$ | $CH_3$ | — | $^iC_3H_7$ |
| 2-173 | H | O | 0 | H | $CF_3$ | $CH_3$ | — | $^iC_4H_9$ |
| 2-174 | H | O | 0 | H | $CF_3$ | $CH_3$ | — | $CH_2CH=CH_2$ |
| 2-175 | H | O | 0 | H | $CF_3$ | $CH_3$ | — | $CH(CH_3)CH=CH_2$ |
| 2-176 | H | O | 0 | H | $CF_3$ | $CH_3$ | — | $CH_2C\equiv CH$ |
| 2-177 | H | O | 0 | H | $CF_3$ | $CH_3$ | — | $CH(CH_3)C\equiv CH$ |
| 2-178 | H | O | 0 | H | $CF_3$ | $CH_3$ | — | $CH_2OCH_3$ |
| 2-179 | H | O | 0 | H | $CF_3$ | $CH_3$ | — | $CH_2OC_2H_5$ |
| 2-180 | F | O | 0 | H | $CF_3$ | $CH_3$ | — | H |
| 2-181 | F | O | 0 | H | $CF_3$ | $CH_3$ | — | $CH_3$ |
| 2-182 | F | O | 0 | H | $CF_3$ | $CH_3$ | — | $C_2H_5$ |
| 2-183 | F | O | 0 | H | $CF_3$ | $CH_3$ | — | $^nC_3H_7$ |
| 2-184 | F | O | 0 | H | $CF_3$ | $CH_3$ | — | $^nC_4H_9$ |
| 2-185 | F | O | 0 | H | $CF_3$ | $CH_3$ | — | $CH_2CH=CH_2$ |
| 2-186 | F | O | 0 | H | $CF_3$ | $CH_3$ | — | $CH(CH_3)CH=CH_2$ |
| 2-187 | F | O | 0 | H | $CF_3$ | $CH_3$ | — | $CH_2C\equiv CH$ |
| 2-188 | F | O | 0 | H | $CF_3$ | $CH_3$ | — | $CH(CH_3)C\equiv CH$ |
| 2-189 | F | O | 0 | H | $CF_3$ | $CH_3$ | — | $CH_2OCH_3$ |
| 2-190 | F | O | 0 | H | $CF_3$ | $CH_3$ | — | $CH_2OC_2H_5$ |
| 2-191 | H | O | 1 | $CH_3$ | $CF_3$ | $CH_3$ | H | H |
| 2-192 | H | O | 1 | $CH_3$ | $CF_3$ | $CH_3$ | H | $CH_3$ |
| 2-193 | H | O | 1 | $CH_3$ | $CF_3$ | $CH_3$ | H | $C_2H_5$ |
| 2-194 | H | O | 1 | $CH_3$ | $CF_3$ | $CH_3$ | H | $^nC_3H_7$ |
| 2-195 | H | O | 1 | $CH_3$ | $CF_3$ | $CH_3$ | H | $^iC_3H_7$ |
| 2-196 | H | O | 1 | $CH_3$ | $CF_3$ | $CH_3$ | H | $^nC_4H_9$ |
| 2-197 | H | O | 1 | $CH_3$ | $CF_3$ | $CH_3$ | H | $CH_2CH_2Cl$ |
| 2-198 | H | O | 1 | $CH_3$ | $CF_3$ | $CH_3$ | H | $CH_2CH_2Br$ |
| 2-199 | H | O | 1 | $CH_3$ | $CF_3$ | $CH_3$ | H | $CH_2CH=CH_2$ |
| 2-200 | H | O | 1 | $CH_3$ | $CF_3$ | $CH_3$ | H | $CH(CH_3)CH=CH_2$ |
| 2-201 | H | O | 1 | $CH_3$ | $CF_3$ | $CH_3$ | H | $CH_2CCl=CH_2$ |
| 2-202 | H | O | 1 | $CH_3$ | $CF_3$ | $CH_3$ | H | $CH_2C\equiv CH$ |
| 2-203 | H | O | 1 | $CH_3$ | $CF_3$ | $CH_3$ | H | $CH(CH_3)C\equiv CH$ |
| 2-204 | H | O | 1 | $CH_3$ | $CF_3$ | $CH_3$ | H | $CH_2CN$ |
| 2-205 | H | O | 1 | $CH_3$ | $CF_3$ | $CH_3$ | H | $CH_2COOH$ |
| 2-206 | H | O | 1 | $CH_3$ | $CF_3$ | $CH_3$ | H | $CH_2COOCH_3$ |
| 2-207 | H | O | 1 | $CH_3$ | $CF_3$ | $CH_3$ | H | $CH_2COOC_2H_5$ |

TABLE 2-continued

Compounds of the formula:

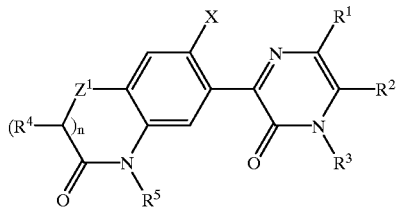

| Compound No | X | $Z^1$ | n | $R^1$ | $R^2$ | $R^3$ | $R^4$ | $R^5$ |
|---|---|---|---|---|---|---|---|---|
| 2-208 | H | O | 1 | $CH_3$ | $CF_3$ | $CH_3$ | H | $CH_2COO^nC_3H_7$ |
| 2-209 | H | O | 1 | $CH_3$ | $CF_3$ | $CH_3$ | H | $CH_2COO^nC_4H_9$ |
| 2-210 | H | O | 1 | $CH_3$ | $CF_3$ | $CH_3$ | H | $CH_2COO^nC_5H_{11}$ |
| 2-211 | H | O | 1 | $CH_3$ | $CF_3$ | $CH_3$ | H | $CH(CH_3)COOH$ |
| 2-212 | H | O | 1 | $CH_3$ | $CF_3$ | $CH_3$ | H | $CH(CH_3)COOH_3$ |
| 2-213 | H | O | 1 | $CH_3$ | $CF_3$ | $CH_3$ | H | $CH(CH_3)COOC_2H_5$ |
| 2-214 | H | O | 1 | $CH_3$ | $CF_3$ | $CH_3$ | H | $CH(CH_3)COO^nC_3H_7$ |
| 2-215 | H | O | 1 | $CH_3$ | $CF_3$ | $CH_3$ | H | $CH(CH_3)COO^nC_4H_9$ |
| 2-216 | H | O | 1 | $CH_3$ | $CF_3$ | $CH_3$ | H | $CH(CH_3)COO^nC_5H_{11}$ |
| 2-217 | F | O | 1 | $CH_3$ | $CF_3$ | $CH_3$ | H | H |
| 2-218 | F | O | 1 | $CH_3$ | $CF_3$ | $CH_3$ | H | $CH_3$ |
| 2-219 | F | O | 1 | $CH_3$ | $CF_3$ | $CH_3$ | H | $C_2H_5$ |
| 2-220 | F | O | 1 | $CH_3$ | $CF_3$ | $CH_3$ | H | $^nC_3H_7$ |
| 2-221 | F | O | 1 | $CH_3$ | $CF_3$ | $CH_3$ | H | $^iC_3H_7$ |
| 2-222 | F | O | 1 | $CH_3$ | $CF_3$ | $CH_3$ | H | $^nC_4H_9$ |
| 2-223 | F | O | 1 | $CH_3$ | $CF_3$ | $CH_3$ | H | $CH_2CH_2Cl$ |
| 2-224 | F | O | 1 | $CH_3$ | $CF_3$ | $CH_3$ | H | $CH_2CH_2Br$ |
| 2-225 | F | O | 1 | $CH_3$ | $CF_3$ | $CH_3$ | H | $CH_2CH=CH_2$ |
| 2-226 | F | O | 1 | $CH_3$ | $CF_3$ | $CH_3$ | H | $CH(CH_3)CH=CH_2$ |
| 2-227 | F | O | 1 | $CH_3$ | $CF_3$ | $CH_3$ | H | $CH_2CCl=CH_2$ |
| 2-228 | F | O | 1 | $CH_3$ | $CF_3$ | $CH_3$ | H | $CH_2C\equiv CH$ |
| 2-229 | F | O | 1 | $CH_3$ | $CF_3$ | $CH_3$ | H | $CH(CH_3)C\equiv CH$ |
| 2-230 | F | O | 1 | $CH_3$ | $CF_3$ | $CH_3$ | H | $CH_2CN$ |
| 2-231 | F | O | 1 | $CH_3$ | $CF_3$ | $CH_3$ | H | $CH_2COOH$ |
| 2-232 | F | O | 1 | $CH_3$ | $CF_3$ | $CH_3$ | H | $CH_2COOCH_3$ |
| 2-233 | F | O | 1 | $CH_3$ | $CF_3$ | $CH_3$ | H | $CH_2COOC_2H_5$ |
| 2-234 | F | O | 1 | $CH_3$ | $CF_3$ | $CH_3$ | H | $CH_2COO^nC_3H_7$ |
| 2-235 | F | O | 1 | $CH_3$ | $CF_3$ | $CH_3$ | H | $CH_2COO^nC_4H_9$ |
| 2-236 | F | O | 1 | $CH_3$ | $CF_3$ | $CH_3$ | H | $CH_2COO^nC_5H_{11}$ |
| 2-237 | F | O | 1 | $CH_3$ | $CF_3$ | $CH_3$ | H | $CH(CH_3)COOH$ |
| 2-238 | F | O | 1 | $CH_3$ | $CF_3$ | $CH_3$ | H | $CH(CH_3)COOCH_3$ |
| 2-239 | F | O | 1 | $CH_3$ | $CF_3$ | $CH_3$ | H | $CH(CH_3)COOC_2H_5$ |
| 2-240 | F | O | 1 | $CH_3$ | $CF_3$ | $CH_3$ | H | $CH(CH_3)COO^nC_3H_7$ |
| 2-241 | F | O | 1 | $CH_3$ | $CF_3$ | $CH_3$ | H | $CH(CH_3)COO^nC_4H_9$ |
| 2-242 | F | O | 1 | $CH_3$ | $CF_3$ | $CH_3$ | H | $CH(CH_3)COO^nC_5H_{11}$ |

TABLE 3

Compounds of the formula:

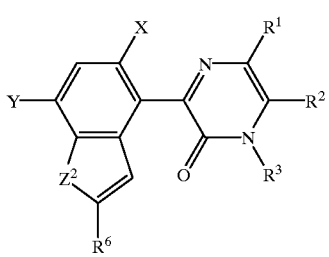

| Compound No. | X | Y | $Z^2$ | $R^1$ | $R^2$ | $R^3$ | $R^6$ |
|---|---|---|---|---|---|---|---|
| 3-1 | H | F | O | H | $CF_3$ | $C_2H_5$ | $CH_3$ |
| 3-2 | H | Cl | O | H | $CF_3$ | $C_2H_5$ | $CH_3$ |
| 3-3 | H | Br | O | H | $CF_3$ | $C_2H_5$ | $CH_3$ |
| 3-4 | F | F | O | H | $CF_3$ | $C_2H_5$ | $CH_3$ |
| 3-5 | F | Cl | O | H | $CF_3$ | $C_2H_5$ | $CH_3$ |
| 3-6 | F | Br | O | H | $CF_3$ | $C_2H_5$ | $CH_3$ |
| 3-7 | H | F | O | H | $CF_3$ | $CH_3$ | $CH_3$ |
| 3-8 | H | Cl | O | H | $CF_3$ | $CH_3$ | $CH_3$ |
| 3-9 | H | Br | O | H | $CF_3$ | $CH_3$ | $CH_3$ |
| 3-10 | F | F | O | H | $CF_3$ | $CH_3$ | $CH_3$ |
| 3-11 | F | Cl | O | H | $CF_3$ | $CH_3$ | $CH_3$ |
| 3-12 | F | Br | O | H | $CF_3$ | $CH_3$ | $CH_3$ |
| 3-13 | H | F | O | H | $CF_3$ | $C_2H_5$ | $C_2H_5$ |
| 3-14 | H | Cl | O | H | $CF_3$ | $C_2H_5$ | $C_2H_5$ |
| 3-15 | H | Br | O | H | $CF_3$ | $C_2H_5$ | $C_2H_5$ |
| 3-16 | F | F | O | H | $CF_3$ | $C_2H_5$ | $C_2H_5$ |
| 3-17 | F | Cl | O | H | $CF_3$ | $C_2H_5$ | $C_2H_5$ |
| 3-18 | F | Br | O | H | $CF_3$ | $C_2H_5$ | $C_2H_5$ |
| 3-19 | H | F | O | H | $CF_3$ | $CH_3$ | $C_2H_5$ |
| 3-20 | H | Cl | O | H | $CF_3$ | $CH_3$ | $C_2H_5$ |
| 3-21 | H | Br | O | H | $CF_3$ | $CH_3$ | $C_2H_5$ |
| 3-22 | F | F | O | H | $CF_3$ | $CH_3$ | $C_2H_5$ |
| 3-23 | F | Cl | O | H | $CF_3$ | $CH_3$ | $C_2H_5$ |
| 3-24 | F | Br | O | H | $CF_3$ | $CH_3$ | $C_2H_5$ |
| 3-25 | H | F | O | H | $CF_3$ | $CH_3$ | $CH_2Br$ |
| 3-26 | H | F | O | H | $CF_3$ | $CH_3$ | $CHBr_2$ |
| 3-27 | H | F | O | H | $CF_3$ | $CH_3$ | $CBr_3$ |
| 3-28 | H | F | O | H | $CF_3$ | $CH_3$ | $CHO$ |
| 3-29 | H | F | O | H | $CF_3$ | $CH_3$ | $CN$ |
| 3-30 | H | F | O | H | $CF_3$ | $CH_3$ | $COOH$ |
| 3-31 | H | F | O | H | $CF_3$ | $CH_3$ | $CH_2OH$ |
| 3-32 | H | F | O | H | $CF_3$ | $CH_3$ | $CH_2OCH_3$ |
| 3-33 | H | F | O | H | $CF_3$ | $CH_3$ | $CH_2OC_2H_5$ |
| 3-34 | H | F | O | H | $CF_3$ | $CH_3$ | $CH_2O^iC_3H_7$ |
| 3-35 | H | F | O | H | $CF_3$ | $CH_3$ | $CH_2OCH_2OCH_3$ |
| 3-36 | H | F | O | H | $CF_3$ | $CH_3$ | $CH_2OCH_2OC_2H_5$ |
| 3-37 | H | F | O | H | $CF_3$ | $CH_3$ | $CH_2OCOCH_3$ |
| 3-38 | H | F | O | H | $CF_3$ | $CH_3$ | $CH_2OCOC_2H_5$ |
| 3-39 | H | F | O | H | $CF_3$ | $CH_3$ | $CH_2OCO^iC_3H_7$ |
| 3-40 | H | F | O | H | $CF_3$ | $CH_3$ | $CH_2OCOCH_2Cl$ |
| 3-41 | H | F | O | H | $CF_3$ | $CH_3$ | $CH_2OCOCCl_3$ |
| 3-42 | H | F | O | H | $CF_3$ | $CH_3$ | $CH_2OCOCF_3$ |
| 3-43 | H | F | O | H | $CF_3$ | $CH_3$ | $COOCH_3$ |
| 3-44 | H | F | O | H | $CF_3$ | $CH_3$ | $COOC_2H_5$ |
| 3-45 | H | F | C | H | $CF_3$ | $CH_3$ | $COO^nC_3H_7$ |
| 3-46 | H | F | O | H | $CF_3$ | $CH_3$ | $COO^nC_4H_9$ |
| 3-47 | H | F | O | H | $CF_3$ | $CH_3$ | $COO^nC_5H_{11}$ |
| 3-48 | H | F | O | H | $CF_3$ | $CH_3$ | $COO^iC_3H_7$ |
| 3-49 | H | F | O | H | $CF_3$ | $CH_3$ | $COCH_3$ |
| 3-50 | H | F | O | H | $CF_3$ | $CH_3$ | $COC_2H_5$ |
| 3-51 | H | Cl | O | H | $CF_3$ | $CH_3$ | $CH_2Br$ |
| 3-52 | H | Cl | O | H | $CF_3$ | $CH_3$ | $CHBr_2$ |
| 3-53 | H | Cl | O | H | $CF_3$ | $CH_3$ | $CBr_3$ |
| 3-54 | H | Cl | O | H | $CF_3$ | $CH_3$ | $CHO$ |
| 3-55 | H | Cl | C | H | $CF_3$ | $CH_3$ | $CN$ |
| 3-56 | H | Cl | O | H | $CF_3$ | $CH_3$ | $COOH$ |
| 3-57 | H | Cl | O | H | $CF_3$ | $CH_3$ | $CH_2OH$ |
| 3-58 | H | Cl | O | H | $CF_3$ | $CH_3$ | $CH_2OCH_3$ |
| 3-59 | H | Cl | O | H | $CF_3$ | $CH_3$ | $CH_2OC_2H_5$ |
| 3-60 | H | Cl | O | H | $CF_3$ | $CH_3$ | $CH_2O^iC_3H_7$ |
| 3-61 | H | Cl | O | H | $CF_3$ | $CH_3$ | $CH_2OCH_2OCH_3$ |
| 3-62 | H | Cl | O | H | $CF_3$ | $CH_3$ | $CH_2OCH_2OC_2H_5$ |
| 3-63 | H | Cl | O | H | $CF_3$ | $CH_3$ | $CH_2OCOCH_3$ |
| 3-64 | H | Cl | O | H | $CF_3$ | $CH_3$ | $CH_2OCOC_2H_5$ |

TABLE 3-continued

Compounds of the formula:

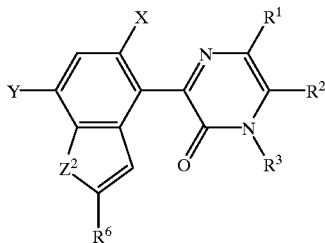

| Compound No. | X | Y | Z² | R¹ | R² | R³ | R⁶ |
|---|---|---|---|---|---|---|---|
| 3-65 | H | Cl | O | H | CF₃ | CH₃ | CH₂OCOⁱC₃H₇ |
| 3-66 | H | Cl | O | H | CF₃ | CH₃ | CH₂OCOCH₂Cl |
| 3-67 | H | Cl | O | H | CF₃ | CH₃ | CH₂OCOCCl₃ |
| 3-68 | H | Cl | O | H | CF₃ | CH₃ | CH₂OCOCF₃ |
| 3-69 | H | Cl | O | H | CF₃ | CH₃ | COOCH₃ |
| 3-70 | H | Cl | O | H | CF₃ | CH₃ | COOC₂H₅ |
| 3-71 | H | Cl | O | H | CF₃ | CH₃ | COOⁿC₃H₇ |
| 3-72 | H | Cl | O | H | CF₃ | CH₃ | COOⁿC₄H₉ |
| 3-73 | H | Cl | O | H | CF₃ | CH₃ | COOⁿC₅H₁₁ |
| 3-74 | H | Cl | C | H | CF₃ | CH₃ | COOⁱC₃H₇ |
| 3-75 | H | Cl | O | H | CF₃ | CH₃ | COCH₃ |
| 3-76 | H | Cl | O | H | CF₃ | CH₃ | COC₂H₅ |
| 3-77 | F | F | O | H | CF₃ | CH₃ | CH₂Br |
| 3-78 | F | F | O | H | CF₃ | CH₃ | CHBr₂ |
| 3-79 | F | F | O | H | CF₃ | CH₃ | CBr₃ |
| 3-80 | F | F | O | H | CF₃ | CH₃ | CHO |
| 3-81 | F | F | O | H | CF₃ | CH₃ | CN |
| 3-82 | F | F | O | H | CF₃ | CH₃ | COOH |
| 3-83 | F | F | O | H | CF₃ | CH₃ | CH₂OH |
| 3-84 | F | F | O | H | CF₃ | CH₃ | CH₂OCH₃ |
| 3-85 | F | F | O | H | CF₃ | CH₃ | CH₂OC₂H₅ |
| 3-86 | F | F | O | H | CF₃ | CH₃ | CH₂OⁱC₃H₇ |
| 3-87 | F | F | O | H | CF₃ | CH₃ | CH₂OCH₂OCH₃ |
| 3-88 | F | F | O | H | CF₃ | CH₃ | CCH₂OCH₂OC₂H₅ |
| 3-89 | F | F | O | H | CF₃ | CH₃ | CH₂OCOCH₃ |
| 3-90 | F | F | O | H | CF₃ | CH₃ | CH₂OCOC₂H₅ |
| 3-91 | F | F | O | H | CF₃ | CH₃ | CH₂OCOⁱC₃H₇ |
| 3-92 | F | F | O | H | CF₃ | CH₃ | CH₂OCOCH₂Cl |
| 3-93 | F | F | O | H | CF₃ | CH₃ | CH₂OCOCCl₃ |
| 3-94 | F | F | O | H | CF₃ | CH₃ | CH₂OCOCF₃ |
| 3-95 | F | F | O | H | CF₃ | CH₃ | COOCH₃ |
| 3-96 | F | F | O | H | CF₃ | CH₃ | COOC₂H₅ |
| 3-97 | F | F | O | H | CF₃ | CH₃ | COOⁿC₃H₇ |
| 3-98 | F | F | O | H | CF₃ | CH₃ | COOⁿC₄H₉ |
| 3-99 | F | F | O | H | CF₃ | CH₃ | COOⁿC₅H₁₁ |
| 3-100 | F | F | O | H | CF₃ | CH₃ | COOⁱC₃H₇ |
| 3-101 | F | F | O | H | CF₃ | CH₃ | COCH₃ |
| 3-102 | F | F | O | H | CF₃ | CH₃ | COC₂H₅ |
| 3-103 | F | Cl | O | H | CF₃ | CH₃ | CH₂Br |
| 3-104 | F | Cl | O | H | CF₃ | CH₃ | CHBr₂ |
| 3-105 | F | Cl | O | H | CF₃ | CH₃ | CBr₃ |
| 3-106 | F | Cl | O | H | CF₃ | CH₃ | CHO |
| 3-107 | F | Cl | O | H | CF₃ | CH₃ | CN |
| 3-108 | F | Cl | O | H | CF₃ | CH₃ | COOH |
| 3-109 | F | Cl | O | H | CF₃ | CH₃ | CH₂OH |
| 3-110 | F | Cl | O | H | CF₃ | CH₃ | CH₂OCH₃ |
| 3-111 | F | Cl | O | H | CF₃ | CH₃ | CH₂OC₂H₅ |
| 3-112 | F | Cl | O | H | CF₃ | CH₃ | CH₂OⁱC₃H₇ |
| 3-113 | F | Cl | O | H | CF₃ | CH₃ | CH₂OCH₂OCH₃ |
| 3-114 | F | Cl | O | H | CF₃ | CH₃ | CH₂OCH₂OC₂H₅ |
| 3-115 | F | Cl | O | H | CF₃ | CH₃ | CH₂OCOCH₃ |
| 3-116 | F | Cl | O | H | CF₃ | CH₃ | CH₂OCOC₂H₅ |
| 3-117 | F | Cl | O | H | CF₃ | CH₃ | CH₂OCOⁱC₃H₇ |
| 3-118 | F | Cl | O | H | CF₃ | CH₃ | CH₂OCOCH₂Cl |
| 3-119 | F | Cl | O | H | CF₃ | CH₃ | CH₂OCOCCl₃ |
| 3-120 | F | Cl | O | H | CF₃ | CH₃ | CH₂OCOCF₃ |
| 3-121 | F | Cl | O | H | CF₃ | CH₃ | COOCH₃ |
| 3-122 | F | Cl | O | H | CF₃ | CH₃ | COOC₂H₅ |
| 3-123 | F | Cl | O | H | CF₃ | CH₃ | COOⁿC₃H₇ |
| 3-124 | F | Cl | O | H | CF₃ | CH₃ | COOⁿC₄H₉ |
| 3-125 | F | Cl | O | H | CF₃ | CH₃ | COOⁿC₅H₁₁ |

TABLE 3-continued

Compounds of the formula:

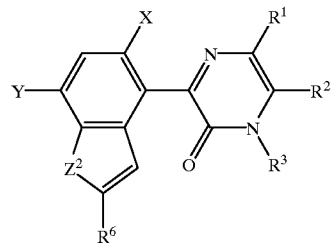

| Compound No. | X | Y | Z² | R¹ | R² | R³ | R⁶ |
|---|---|---|---|---|---|---|---|
| 3-126 | F | Cl | O | H | CF₃ | CH₃ | COOⁱC₃H₇ |
| 3-127 | F | Cl | O | H | CF₃ | CH₃ | COCH₃ |
| 3-128 | F | Cl | O | H | CF₃ | CH₃ | COC₂H₅ |

TABLE 4

Compounds of the formula:

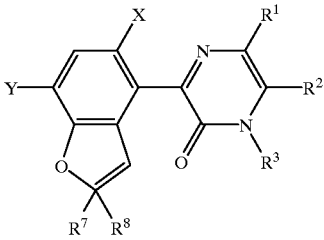

| Compound No. | X | Y | R¹ | R² | R³ | R⁷ | R⁸ |
|---|---|---|---|---|---|---|---|
| 4-1 | H | F | H | CF₃ | C₂H₅ | H | CH₃ |
| 4-2 | H | Cl | H | CF₃ | C₂H₅ | H | CH₃ |
| 4-3 | H | Br | H | CF₃ | C₂H₅ | H | CH₃ |
| 4-4 | H | F | H | CF₃ | C₂H₅ | H | CH₂OH |
| 4-5 | H | Cl | H | CF₃ | C₂H₅ | H | CH₂OH |
| 4-6 | H | Br | H | CF₃ | C₂H₅ | H | CH₂OH |
| 4-7 | H | F | H | CF₃ | C₂H₅ | CH₃ | CH₃ |
| 4-8 | H | Cl | H | CF₃ | C₂H₅ | CH₃ | CH₃ |
| 4-9 | H | Br | H | CF₃ | C₂H₅ | CH₃ | CH₃ |
| 4-10 | H | Br | H | CF₃ | C₂H₅ | CH₃ | CH₃ |
| 4-11 | H | F | H | CF₃ | C₂H₅ | CH₃ | CH₂OH |
| 4-12 | H | Cl | H | CF₃ | C₂H₅ | CH₃ | CH₂OH |
| 4-13 | H | Br | H | CF₃ | C₂H₅ | CH₃ | CH₂OH |
| 4-14 | F | F | H | CF₃ | C₂H₅ | H | CH₃ |
| 4-15 | F | Cl | H | CF₃ | C₂H₅ | H | CH₃ |
| 4-16 | F | Br | H | CF₃ | C₂H₅ | H | CH₃ |
| 4-17 | F | F | H | CF₃ | C₂H₅ | H | CH₂OH |
| 4-18 | F | Cl | H | CF₃ | C₂H₅ | H | CH₂OH |
| 4-19 | F | Br | H | CF₃ | C₂H₅ | H | CH₂OH |
| 4-20 | F | F | H | CF₃ | C₂H₅ | CH₃ | CH₃ |
| 4-21 | F | Cl | H | CF₃ | C₂H₅ | CH₃ | CH₃ |
| 4-22 | F | Br | H | CF₃ | C₂H₅ | CH₃ | CH₃ |
| 4-23 | F | F | H | CF₃ | C₂H₅ | CH₃ | CH₂OH |
| 4-24 | F | Cl | H | CF₃ | C₂H₅ | CH₃ | CH₂OH |
| 4-25 | F | Br | H | CF₃ | C₂H₅ | CH₃ | CH₂OH |
| 4-26 | H | Cl | H | CF₃ | CH₃ | H | CH₂Cl |
| 4-27 | H | Cl | H | CF₃ | CH₃ | H | CH₂Br |
| 4-28 | H | Cl | H | CF₃ | CH₃ | H | CH₂OCH₃ |
| 4-29 | H | Cl | H | CF₃ | CH₃ | H | CH₂OC₂H₅ |
| 4-30 | H | Cl | H | CF₃ | CH₃ | H | CH₂OCH₂OCH₃ |
| 4-31 | H | Cl | H | CF₃ | CH₃ | H | CH₂OCH₂OC₂H₅ |
| 4-32 | H | Cl | H | CF₃ | CH₃ | H | CH₂OCOCH₃ |
| 4-33 | H | Cl | H | CF₃ | CH₃ | H | CH₂OCOC₂H₅ |
| 4-34 | H | Cl | H | CF₃ | CH₃ | H | CH₂OCOⁱC₃H₇ |
| 4-35 | H | Cl | H | CF₃ | CH₃ | H | CH₂OCOCH₂Cl |
| 4-36 | H | Cl | H | CF₃ | CH₃ | H | CH₂OCOCCl₃ |

TABLE 4-continued

Compounds of the formula:

(structure shown: benzofuran substituted with X, Y, and linked to pyrazinone ring with R¹, R², R³, R⁷, R⁸)

| Compound No. | X | Y | R¹ | R² | R³ | R⁷ | R⁸ |
|---|---|---|---|---|---|---|---|
| 4-37 | H | Cl | H | $CF_3$ | $CH_3$ | H | $CH_2OCOCF_3$ |
| 4-38 | H | Cl | H | $CF_3$ | $CH_3$ | H | COOH |
| 4-39 | H | Cl | H | $CF_3$ | $CH_3$ | H | $COOCH_3$ |
| 4-40 | H | Cl | H | $CF_3$ | $CH_3$ | H | $COOC_2H_5$ |
| 4-41 | H | Cl | H | $CF_3$ | $CH_3$ | H | $COO^nC_3H_7$ |
| 4-42 | H | Cl | H | $CF_3$ | $CH_3$ | H | $COO^nC_4H_9$ |
| 4-43 | H | Cl | H | $CF_3$ | $CH_3$ | H | $COO^nC_5H_{11}$ |
| 4-44 | H | Cl | H | $CF_3$ | $CH_3$ | H | $COO^iC_3H_7$ |
| 4-45 | H | Cl | H | $CF_3$ | $CH_3$ | H | $COO^cC_5H_9$ |
| 4-46 | H | Cl | H | $CF_3$ | $CH_3$ | H | $COO^cC_6H_{11}$ |
| 4-47 | H | Cl | H | $CF_3$ | $CH_3$ | H | $COOCH_2CH=CH_2$ |
| 4-48 | H | Cl | H | $CF_3$ | $CH_3$ | H | $COOCH_2C\equiv CH$ |
| 4-49 | H | Cl | H | $CF_3$ | $CH_3$ | H | $CONH_2$ |
| 4-50 | H | Cl | H | $CF_3$ | $CH_3$ | H | $CONHCH_3$ |
| 4-51 | H | Cl | H | $CF_3$ | $CH_3$ | H | $CONHC_2H_5$ |
| 4-52 | H | Cl | H | $CF_3$ | $CH_3$ | H | $CON(CH_3)_2$ |
| 4-53 | H | Cl | H | $CF_3$ | $CH_3$ | H | $CON(C_2H_5)_2$ |
| 4-54 | F | Cl | H | $CF_3$ | $CH_3$ | H | $CH_2Cl$ |
| 4-55 | F | Cl | H | $CF_3$ | $CH_3$ | H | $CH_2Br$ |
| 4-56 | F | Cl | H | $CF_3$ | $CH_3$ | H | $CH_2OCH_3$ |
| 4-57 | F | Cl | H | $CF_3$ | $CH_3$ | H | $CH_2OC_2H_5$ |
| 4-58 | F | Cl | H | $CF_3$ | $CH_3$ | H | $CH_2OCH_2OCH_3$ |
| 4-59 | F | Cl | H | $CF_3$ | $CH_3$ | H | $CH_2OCH_2OC_2H_5$ |
| 4-60 | F | Cl | H | $CF_3$ | $CH_3$ | H | $CH_2OCOCH_3$ |
| 4-61 | F | Cl | H | $CF_3$ | $CH_3$ | H | $CH_2OCOC_2H_5$ |
| 4-62 | F | Cl | H | $CF_3$ | $CH_3$ | H | $CH_2OCO^iC_3H_7$ |
| 4-63 | F | Cl | H | $CF_3$ | $CH_3$ | H | $CH_2OCOCH_2Cl$ |
| 4-64 | F | Cl | H | $CF_3$ | $CH_3$ | H | $CH_2OCOCCl_3$ |
| 4-65 | F | Cl | H | $CF_3$ | $CH_3$ | H | $CH_2OCOCF_3$ |
| 4-66 | F | Cl | H | $CF_3$ | $CH_3$ | H | COOH |
| 4-67 | F | Cl | H | $CF_3$ | $CH_3$ | H | $COOCH_3$ |
| 4-68 | F | Cl | H | $CF_3$ | $CH_3$ | H | $COOC_2H_5$ |
| 4-69 | F | Cl | H | $CF_3$ | $CH_3$ | H | $COO^nC_3H_7$ |
| 4-70 | F | Cl | H | $CF_3$ | $CH_3$ | H | $COO^nC_4H_9$ |
| 4-71 | F | Cl | H | $CF_3$ | $CH_3$ | H | $COO^nC_5H_{11}$ |
| 4-72 | F | Cl | H | $CF_3$ | $CH_3$ | H | $COO^iC_3H_7$ |
| 4-73 | F | Cl | H | $CF_3$ | $CH_3$ | H | $COO^cC_5H_9$ |
| 4-74 | F | Cl | H | $CF_3$ | $CH_3$ | H | $COO^cC_6H_{11}$ |
| 4-75 | F | Cl | H | $CF_3$ | $CH_3$ | H | $COOCH_2CH=CH_2$ |
| 4-76 | F | Cl | H | $CF_3$ | $CH_3$ | H | $COOCH_2C\equiv CH$ |
| 4-77 | F | Cl | H | $CF_3$ | $CH_3$ | H | $CONH_2$ |
| 4-78 | F | Cl | H | $CF_3$ | $CH_3$ | H | $CONHCH_3$ |
| 4-79 | F | Cl | H | $CF_3$ | $CH_3$ | H | $CONHC_2H_5$ |
| 4-80 | F | Cl | H | $CF_3$ | $CH_3$ | H | $CON(CH_3)_2$ |
| 4-81 | F | Cl | H | $CF_3$ | $CH_3$ | H | $CON(C_2H_5)_2$ |
| 4-82 | H | Cl | H | $CF_3$ | $CH_3$ | $CH_3$ | $CH_2Cl$ |
| 4-83 | H | Cl | H | $CF_3$ | $CH_3$ | $CH_3$ | $CH_2Br$ |
| 4-84 | H | Cl | H | $CF_3$ | $CH_3$ | $CH_3$ | $CH_2OCH_3$ |
| 4-85 | H | Cl | H | $CF_3$ | $CH_3$ | $CH_3$ | $CH_2OC_2H_5$ |
| 4-86 | H | Cl | H | $CF_3$ | $CH_3$ | $CH_3$ | $CH_2OCH_2OCH_3$ |
| 4-87 | H | Cl | H | $CF_3$ | $CH_3$ | $CH_3$ | $CH_2OCH_2OC_2H_5$ |
| 4-88 | H | Cl | H | $CF_3$ | $CH_3$ | $CH_3$ | $CH_2OCOCH_3$ |
| 4-89 | H | Cl | H | $CF_3$ | $CH_3$ | $CH_3$ | $CH_2OCOC_2H_5$ |
| 4-90 | H | Cl | H | $CF_3$ | $CH_3$ | $CH_3$ | $CH_2OCO^iC_3H_7$ |
| 4-91 | H | Cl | H | $CF_3$ | $CH_3$ | $CH_3$ | $CH_2OCOCH_2Cl$ |
| 4-92 | H | Cl | H | $CF_3$ | $CH_3$ | $CH_3$ | $CH_2OCOCCl_3$ |
| 4-93 | H | Cl | H | $CF_3$ | $CH_3$ | $CH_3$ | $CH_2OCOCF_3$ |
| 4-94 | H | Cl | H | $CF_3$ | $CH_3$ | $CH_3$ | COOH |
| 4-95 | H | Cl | H | $CF_3$ | $CH_3$ | $CH_3$ | $COOCH_3$ |
| 4-96 | H | Cl | H | $CF_3$ | $CH_3$ | $CH_3$ | $COOC_2H_5$ |
| 4-97 | H | Cl | H | $CF_3$ | $CH_3$ | $CH_3$ | $COO^nC_3H_7$ |
| 4-98 | H | Cl | H | $CF_3$ | $CH_3$ | $CH_3$ | $COO^nC_4H_9$ |
| 4-99 | H | Cl | H | $CF_3$ | $CH_3$ | $CH_3$ | $COO^nC_5H_{11}$ |
| 4-100 | H | Cl | H | $CF_3$ | $CH_3$ | $CH_3$ | $COO^iC_3H_7$ |
| 4-101 | H | Cl | H | $CF_3$ | $CH_3$ | $CH_3$ | $COO^cC_5H_9$ |
| 4-102 | H | Cl | H | $CF_3$ | $CH_3$ | $CH_3$ | $COO^cC_6H_{11}$ |
| 4-103 | H | Cl | H | $CF_3$ | $CH_3$ | $CH_3$ | $COOCH_2CH=CH_2$ |
| 4-104 | H | Cl | H | $CF_3$ | $CH_3$ | $CH_3$ | $COOCH_2C\equiv CH$ |
| 4-105 | H | Cl | H | $CF_3$ | $CH_3$ | $CH_3$ | $CONH_2$ |
| 4-106 | H | Cl | H | $CF_3$ | $CH_3$ | $CH_3$ | $CONHCH_3$ |
| 4-107 | H | Cl | H | $CF_3$ | $CH_3$ | $CH_3$ | $CONHC_2H_5$ |
| 4-108 | H | Cl | H | $CF_3$ | $CH_3$ | $CH_3$ | $CON(CH_3)_2$ |
| 4-109 | H | Cl | H | $CF_3$ | $CH_3$ | $CH_3$ | $CON(C_2H_5)_2$ |
| 4-110 | F | Cl | H | $CF_3$ | $CH_3$ | $CH_3$ | $CH_2Cl$ |
| 4-111 | F | Cl | H | $CF_3$ | $CH_3$ | $CH_3$ | $CH_2Br$ |
| 4-112 | F | Cl | H | $CF_3$ | $CH_3$ | $CH_3$ | $CH_2OCH_3$ |
| 4-113 | F | Cl | H | $CF_3$ | $CH_3$ | $CH_3$ | $CH_2OC_2H_5$ |
| 4-114 | F | Cl | H | $CF_3$ | $CH_3$ | $CH_3$ | $CH_2OCH_2OCH_3$ |
| 4-115 | F | Cl | H | $CF_3$ | $CH_3$ | $CH_3$ | $CH_2OCH_2OC_2H_5$ |
| 4-116 | F | Cl | H | $CF_3$ | $CH_3$ | $CH_3$ | $CH_2OCOCH_3$ |
| 4-117 | F | Cl | H | $CF_3$ | $CH_3$ | $CH_3$ | $CH_2OCOC_2H_5$ |
| 4-118 | F | Cl | H | $CF_3$ | $CH_3$ | $CH_3$ | $CH_2OCO^iC_3H_7$ |
| 4-119 | F | Cl | H | $CF_3$ | $CH_3$ | $CH_3$ | $CH_2OCOCH_2Cl$ |
| 4-120 | F | Cl | H | $CF_3$ | $CH_3$ | $CH_3$ | $CH_2OCOCCl_3$ |
| 4-121 | F | Cl | H | $CF_3$ | $CH_3$ | $CH_3$ | $CH_2OCOCF_3$ |
| 4-122 | F | Cl | H | $CF_3$ | $CH_3$ | $CH_3$ | COOH |
| 4-123 | F | Cl | H | $CF_3$ | $CH_3$ | $CH_3$ | $COOCH_3$ |
| 4-124 | F | Cl | H | $CF_3$ | $CH_3$ | $CH_3$ | $COOC_2H_5$ |
| 4-125 | F | Cl | H | $CF_3$ | $CH_3$ | $CH_3$ | $COO^nC_3H_7$ |
| 4-126 | F | Cl | H | $CF_3$ | $CH_3$ | $CH_3$ | $COO^nC_4H_9$ |
| 4-127 | F | Cl | H | $CF_3$ | $CH_3$ | $CH_3$ | $COO^nC_5H_{11}$ |
| 4-128 | F | Cl | H | $CF_3$ | $CH_3$ | $CH_3$ | $COO^iC_3H_7$ |
| 4-129 | F | Cl | H | $CF_3$ | $CH_3$ | $CH_3$ | $COO^cC_4H_9$ |
| 4-130 | F | Cl | H | $CF_3$ | $CH_3$ | $CH_3$ | $COO^cC_6H_{11}$ |
| 4-131 | F | Cl | H | $CF_3$ | $CH_3$ | $CH_3$ | $COOCH_2CH=CH_2$ |
| 4-132 | F | Cl | H | $CF_3$ | $CH_3$ | $CH_3$ | $COOCH_2C\equiv CH$ |
| 4-133 | F | Cl | H | $CF_3$ | $CH_3$ | $CH_3$ | $CONH_2$ |
| 4-134 | F | Cl | H | $CF_3$ | $CH_3$ | $CH_3$ | $CONHCH_3$ |
| 4-135 | F | Cl | H | $CF_3$ | $CH_3$ | $CH_3$ | $CONHC_2H_5$ |
| 4-136 | F | Cl | H | $CF_3$ | $CH_3$ | $CH_3$ | $CON(CH_3)_2$ |
| 4-137 | F | Cl | H | $CF_3$ | $CH_3$ | $CH_3$ | $CON(C_2H_5)_2$ |

TABLE 5

Compounds of the formula:

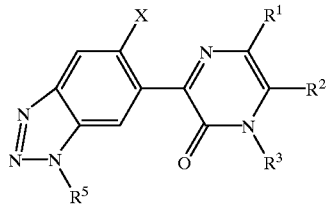

| Compound No. | X | $R^1$ | $R^2$ | $R^3$ | $R^5$ |
|---|---|---|---|---|---|
| 5-1 | H | H | $CF_3$ | $CH_3$ | $CH_3$ |
| 5-2 | H | H | $CF_3$ | $CH_3$ | $C_2H_5$ |
| 5-3 | H | H | $CF_3$ | $CH_3$ | $^iC_3H_7$ |
| 5-4 | H | H | $CF_3$ | $CH_3$ | $^nC_3H_7$ |
| 5-5 | H | H | $CF_3$ | $CH_3$ | $^iC_4H_9$ |
| 5-6 | H | H | $CF_3$ | $CH_3$ | $CH_2CH=CH_2$ |
| 5-7 | H | H | $CF_3$ | $CH_3$ | $CH(CH_3)CH=CH_2$ |
| 5-8 | H | H | $CF_3$ | $CH_3$ | $CH_2C\equiv CH$ |
| 5-9 | H | H | $CF_3$ | $CH_3$ | $CH(CH_3)C\equiv CH$ |
| 5-10 | F | H | $CF_3$ | $CH_3$ | $CH_3$ |
| 5-11 | F | H | $CF_3$ | $CH_3$ | $C_2H_5$ |
| 5-12 | F | H | $CF_3$ | $CH_3$ | $^iC_3H_7$ |
| 5-13 | F | H | $CF_3$ | $CH_3$ | $^iC_4H_9$ |
| 5-14 | F | H | $CF_3$ | $CH_3$ | $CH_2CH=CH_2$ |
| 5-15 | F | H | $CF_3$ | $CH_3$ | $CH(CH_3)CH=CH_2$ |
| 5-16 | F | H | $CF_3$ | $CH_3$ | $CH_2C\equiv CH$ |
| 5-17 | F | H | $CF_3$ | $CH_3$ | $CH(CH_3)C\equiv CH$ |

The following will describe production examples for compound [2] as an intermediate compound for the production of the present compounds.

INTERMEDIATE PRODUCTION EXAMPLE 1

To a mixed solution of 121 g of sodium carbonate and 400 ml of water was added dropwise 77.1 g of 1,1-dibromo-3,3,3-trifluoroacetone at such a rate that the temperature of the reaction mixture became not higher than 55° C. After completion of the dropwise addition, the mixture was stirred at room temperature for 30 minutes, followed by adding 500 ml of water and then 40 g of 2-amino-2-(2,4-difluorophenyl) acetamide, and the reaction was allowed to proceed at 60° C. for 2 hours. After completion of the reaction, the reaction mixture was cooled to 10° C. or lower, made acidic by adding 80 ml of concentrated hydrochloric acid at the same temperature, and extracted with ethyl acetate. The organic layer was washed with water and then saturated sodium chloride solution, dried with anhydrous magnesium sulfate, and concentrated. The residue was subjected to silica gel column chromatography (eluent, hexane/ethyl acetate=4:1), which afforded 23.3 g (yield, 39%) of the desired compound, 3-(2,4-difluorophenyl)-6-trifluoromethyl-2-oxo-1,2-dihydropyrazine (compound 1-1004; m.p., 178.9° C.). The continued elution with the above solvent system gave 13.2 g of the configurational isomer, 3-(2,4-difluorophenyl)-5-trifluoromethyl-2-oxo-1,2-dihydropyrazine (m.p., 164.6° C.).

INTERMEDIATE PRODUCTION EXAMPLE 2

To a mixed solution of 17.2 g of sodium carbonate and 61 ml of water was added dropwise 10.9 g of 1,1-dibromo-3,3,3-trifluoroacetone at such a rate that the temperature of the reaction mixture became not higher than 55° C. After completion of the dropwise addition, the mixture was stirred at room temperature for 30 minutes, followed by adding 84 ml of water and then 7.10 g of 2-amino-2-(4-chloro-2-fluoro-5-methoxyphenyl)acetamide, and the reaction was allowed to proceed at 60° C. for 2 hours. After completion of the reaction, the reaction mixture was cooled to 10° C. or lower, made acidic by adding 9.2 ml of concentrated hydrochloric acid at the same temperature, and extracted with ethyl acetate. The organic layer was washed with water and then saturated sodium chloride solution, dried with anhydrous magnesium sulfate, and concentrated. The residue was subjected to silica gel column chromatography (eluent, hexane/ethyl acetate=4:1), which afforded 3.61 g (yield, 37%) of the desired compound, 3-(4-chloro-2-fluoro-5-methoxyphenyl)-6-trifluoromethyl-2-oxo-1,2-dihydropyrazine (compound 1-1008).

$^1$H-NMR (CDCl$_3$/TMS, 250 MHz, δ (ppm)) 3.93 (s, 3H), 7.18 (d, 1H, J=6.1 Hz), 7.27 (d, 1H, J=10.0 Hz), 8.55 (s, 1H)

INTERMEDIATE PRODUCTION EXAMPLE 3

To a mixed solution of 28 g of sodium carbonate and 100 ml of water was added dropwise 18.0 g of 1,1-dibromo-3,3,3-trifluoroacetone at such a rate that the temperature of the reaction mixture became not higher than 55° C. After completion of the dropwise addition, the mixture was stirred at room temperature for 30 minutes, followed by adding 125 ml of water and then 8.4 g of 2-amino-2-(4-fluorophenyl) acetamide, and the reaction was allowed to proceed at 60° C. for 2 hours. After completion of the reaction, the reaction mixture was cooled to 10° C. or lower, made acidic by adding 20 ml of concentrated hydrochloric acid at the same temperature, and extracted with ethyl acetate. The organic layer was washed with water and then saturated sodium chloride solution, dried with anhydrous magnesium sulfate, and concentrated. The residue was subjected to silica gel column chromatography (eluent, hexane/ethyl acetate=5:1), which afforded 2.45 g (yield, 19%) of the desired compound, 3-(4-fluorophenyl)-6-trifluoromethyl-2-oxo-1,2-dihydropyrazine (compound 1-1001).

$^1$H-NMR (CDCl$_3$/TMS, 300 MHz, δ (ppm)) 7.1–7.3 (m, 2H), 8.3–8.4 (m, 2H), 8.48 (s, 1H)

INTERMEDIATE PRODUCTION EXAMPLE 4

To a mixed solution of 35.5 g of sodium carbonate and 120 ml of water was added dropwise 22.7 g of 1,1-dibromo-3,3,3-trifluoroacetone at such a rate that the temperature of the reaction mixture became not higher than 55° C. After completion of the dropwise addition, the mixture was stirred at room temperature for 30 minutes, followed by adding 150 ml of water and then 12.8 g of 2-amino-2-(4-chloro-2-fluorophenyl)acetamide, and the reaction was allowed to proceed at 60° C. for 2 hours. After completion of the reaction, the reaction mixture was cooled to 10° C. or lower, made acidic by adding 20 ml of concentrated hydrochloric acid at the same temperature, and extracted with ethyl acetate. The organic layer was washed with water and then saturated sodium chloride solution, dried with anhydrous magnesium sulfate, and concentrated. The residue was subjected to silica gel column chromatography (eluent, hexane/ethyl acetate=4:1), which afforded 5.83 g (yield, 32%) of the desired compound, 3-(4-chloro-2-fluorophenyl)-6-trifluoromethyl-2-oxo-1,2-dihydropyrazine (compound 1-1005; m.p., 83.2° C.). The continued elution with the above solvent system gave 4.32 g of the configurational isomer, 3-(4-chloro-2-fluorophenyl)-5-trifluoromethyl-2-oxo-1,2-dihydropyrazine.

INTERMEDIATE PRODUCTION EXAMPLE 5

To a mixed solution of 7.9 g of sodium carbonate and 31 ml of water was added dropwise 5.1 g of 1,1-dibromo-3,3, 3-trifluoroacetone at such a rate that the temperature of the reaction mixture became not higher than 55° C. After completion of the dropwise addition, the mixture was stirred at room temperature for 30 minutes, followed by adding 39 ml of water and then 3.1 g of 2-amino-2-(2,4-dichlorophenyl)acetamide, and the reaction was allowed to proceed at 60° C. for 2 hours. After completion of the reaction, the reaction mixture was cooled to 10° C. or lower, made acidic by adding 5.4 ml of concentrated hydrochloric acid at the same temperature, and extracted with ethyl acetate. The organic layer was washed with water and then saturated sodium chloride solution, dried with anhydrous magnesium sulfate, and concentrated. The residue was subjected to silica gel column chromatography (eluent, hexane/ethyl acetate=4:1), which afforded 1.54 g (yield, 35%) of the desired compound, 3-(2,4-dichlorophenyl)-6-trifluoromethyl-2-oxo-1,2-dihydropyrazine (compound 1-1007; m.p., 192.8° C.). The continued elution with the above solvent system gave 0.53 g of the configurational isomer, 3-(2,4-dichlorophenyl)-5-trifluoromethyl-2-oxo-1,2-dihydropyrazine (m.p., 131.7° C.).

INTERMEDIATE PRODUCTION EXAMPLE 6

To a mixed solution of 16.7 g of sodium carbonate and 60 ml of water was added dropwise 10.6 g of 1,1-dibromo-3,3,3-trifluoroacetone at such a rate that the temperature of the reaction mixture became not higher than 55° C. After completion of the dropwise addition, the mixture was stirred at room temperature for 30 minutes, followed by adding 80 ml of water and then 7.42 g of 2-amino-2-(2,4-dichloro-5-methoxyphenyl)acetamide, and the reaction was allowed to proceed at 60° C. for 2 hours. After completion of the reaction, the reaction mixture was cooled to 10° C. or lower, made acidic by adding 9.0 ml of concentrated hydrochloric acid at the same temperature, and extracted with ethyl acetate. The organic layer was washed with water and then saturated sodium chloride solution, dried with anhydrous magnesium sulfate, and concentrated. The residue was subjected to silica gel column chromatography (eluent, hexane/ethyl acetate=4:1), which afforded 2.2 g (yield, 22%) of the desired compound, 3-(2,4-dichloro-5-methoxyphenyl)-6-trifluoromethyl-2-oxo-1,2-dihydropyrazine (compound 1-1009).

$^1$H-NMR (CDCl$_3$/TMS, 300 MHz, δ (ppm)) 3.90 (s, 3H), 7.03 (s, 1H), 7.53 (s, 1H), 8.58 (s, 1H)

The following will describe production examples for compound [24] as a starting compound for the production of the present compounds.

REFERENCE PRODUCTION EXAMPLE 1

(1) A mixture of 20.7 g of sodium cyanide, 31 ml of concentrated ammonia water (28%), 27 ml of water, and 30.8 g of ammonium chloride was stirred at 15° C. for 1 hour, to which 20 ml of ether was added at the same temperature. The reaction mixture was cooled to 2.5° to 4° C., to which 50 g of 2,4-difluorobenzaldehyde was added. Then, ammonia gas was bubbled into the reaction mixture at −0.5° to 1° C. for 3 hours, and the reaction mixture was stirred at the same temperature for 2 hours and then at room temperature overnight.

After completion of the reaction, the reaction mixture was extracted with ether, and the organic layer was washed with water and then saturated sodium chloride solution, dried with anhydrous magnesium sulfate, and concentrated. The precipitated crystals were recrystallized, which afforded 47.1 g (yield, 80%) of 2-amino-2-(2,4-difluorophenyl) acetonitrile, m.p. 52.0° C.

(2) Then, 51 g of concentrated sulfuric acid was added to 2.67 g of water, to which 40 g of 2-amino-2-(2,4-difluorophenyl)acetonitrile was added under ice cooling, and the mixture was heated at 50° to 60° C. under stirring for 3 hours. After completion of the reaction, the reaction mixture was poured into 250 ml of concentrated ammonia water cooled with ice in such a manner that the temperature of the solution became not higher than 20° C. The precipitated crystals were collected by filtration, and the filtrate was extracted with ethyl acetate. The organic layer was washed with saturated sodium chloride solution, dried with anhydrous magnesium sulfate, and concentrated. The residue was combined with the previously collected crystals, followed by recrystallization, which afforded 27.2 g (yield, 61%) of 2-amino-2-(2,4-difluorophenyl)acetamide, m.p. 142.9° C.

REFERENCE PRODUCTION EXAMPLE 2

(1) To a mixture of 39 g of concentrated sulfuric acid and 149 ml of water was added dropwise a solution of 34.2 g of 4-chloro-2-fluoro-5-methoxyaniline in 30 ml of diethyl ether at room temperature, and the mixture was stirred at 40° to 50° C. for 50 minutes. The diethyl ether was distilled out at the same temperature, and the reaction mixture was cooled to 0° C., to which a solution of 14.8 g of sodium nitrite in 33 ml of water was added at such a rate that the temperature of the reaction system was kept not higher than 10° C. Then, taking care that the reaction mixture had no temperature rise, the reaction mixture was filtered through celite. The filtrate was added dropwise to a solution of 64.7 g of potassium iodide in 100 ml of water at such a rate that the temperature of the reaction system was kept not higher than 10° C. At the same time, 100 ml of hexane and 100 ml of diethyl ether were added, and the mixture was stirred at the same temperature for 2 hours. After completion of the reaction, the reaction mixture was extracted with diethyl ether. The organic layer was washed with saturated sodium thiosulfate solution, dried with anhydrous magnesium sulfate, and concentrated. The residue was subjected to silica gel column chromatography, which afforded 25.7 g (yield, 47%) of 2-chloro-4-fluoro-5-iodo-1-methoxybenzene.

$^1$H-NMR (CDCl$_3$/TMS, 250 MHz, δ (ppm)) 3.88 (s, 3H), 7.12 (d, 1H, J=7.2 Hz), 7.22 (d, 1H, J=5.4 Hz)

(2) A mixture of 36.3 g of 2-chloro-4-fluoro-5-iodo-1-methoxybenzene, 12.9 g of sodium formate, 1.78 g of dichlorobis(triphenylphosphine) palladium, and 113 ml of N,N-dimethylformamide was stirred, while bubbling carbon monoxide at 90° to 100° C. over 12 hours. After completion of the reaction, the reaction mixture was returned to room temperature, followed by dilution with diluted hydrochloric acid, and the mixture was extracted with ethyl acetate. The organic layer was washed with saturated sodium chloride solution, dried with anhydrous magnesium sulfate, and concentrated. The residue was subjected to silica gel column chromatography, which afforded 7.09 g (yield, 30%) of 4-chloro-2-fluoro-5-methoxybenzaldehyde.

$^1$H-NMR (CDCl$_3$/TMS, 250 MHz, δ (ppm)) 3.94 (s, 3H), 7.27 (d, 1H, J=9.4 Hz), 7.35 (d, 1H, J=5.9 Hz), 10.30 (s, 1H)

(3) A mixture of 4.4 g of sodium cyanide, 6.6 ml of concentrated ammonia water (28%), 5.3 ml of water, and 6.6 g of ammonium chloride was stirred at 15° C. for 1 hour, to which 4.3 ml of ether was added at the same temperature. The reaction mixture was cooled to 2.5° to 4° C., to which a solution of 14.2 g of 4-chloro-2-fluoro-5-methoxybenzaldehyde in 13.1 ml of methanol was added at the same temperature. Then, ammonia gas was bubbled into the reaction mixture at −0.5° to 1° C. for 3 hours, and the reaction mixture was stirred at the same temperature for 2 hours and then at room temperature overnight.

After completion of the reaction, the reaction mixture was extracted with ether, and the organic layer was washed with water and then saturated sodium chloride solution, dried with anhydrous magnesium sulfate, and concentrated. The precipitated crystals were recrystallized, which afforded 15.3 g (yield, 95%) of 2-amino-2-(4-chloro-2-fluoro-5-methoxy)acetonitrile.

$^1$H-NMR (CDCl$_3$/TMS, 300 MHz, δ (ppm)) 1.9–2.1 (br, 2H), 3.93 (s, 3H), 5.10 (t, 1H, J=6.7 Hz), 7.09 (d, 1H, J=6.5 Hz), 7.20 (d, 1H, J=9.3 Hz)

(4) Then, 3.6 g of concentrated sulfuric acid was added to 0.33 g of water, to which 3.6 g of 2-amino-2-(4-chloro-2-fluoro-5-methoxyphenyl)acetonitrile was added under ice cooling, and the mixture was heated at 50° to 60° C. under stirring for 3 hours. After completion of the reaction, the reaction mixture was poured into 15 ml of concentrated ammonia water cooled with ice in such a manner that the temperature of the solution became not higher than 20° C. The precipitated crystals were collected by filtration, and the filtrate was extracted with ethyl acetate. The organic layer was washed with saturated sodium chloride solution, dried with anhydrous magnesium sulfate, and concentrated. The residue was combined with the previously collected crystals, followed by recrystallization, which afforded 2.45 g (yield, 68%) of 2-amino-2-(4-chloro-2-fluoro-5-methoxyphenyl)acetamide, m.p. 161.7° C.

REFERENCE PRODUCTION EXAMPLE 3

(1) A mixture of 9.5 g of sodium cyanide, 14.1 ml of concentrated ammonia water (28%), 10.6 ml of water, and 14.1 g of ammonium chloride was stirred at 15° C. for 1 hour, to which 20 ml of ether was added at the same temperature. The reaction mixture was cooled to 2.5° to 4° C., to which 20 g of 4-fluorobenzaldehyde was added at the same temperature. Then, ammonia gas was bubbled into the reaction mixture at −0.5° to 1° C. for 3 hours, and the reaction mixture was stirred at the same temperature for 2 hours and then at room temperature overnight.

After completion of the reaction, the reaction mixture was extracted with ether, and the organic layer was washed with water and then saturated sodium chloride solution, dried with anhydrous magnesium sulfate, and concentrated. The precipitated crystals were recrystallized, which afforded 20 g (yield, 83%) of 2-amino-2-(4-fluorophenyl)acetonitrile, m.p. 77.9° C.

(2) Then, 30 g of concentrated sulfuric acid was added to 1.45 g of water, to which 20 g of 2-amino-2-(4-fluorophenyl)acetonitrile was added under ice cooling, and the mixture was heated at 50° to 60° C. under stirring for 3 hours. After completion of the reaction, the reaction mixture was poured into 200 ml of concentrated ammonia water cooled with ice in such a manner that the temperature of the solution became not higher than 20° C. The precipitated crystals were collected by filtration, and the filtrate was extracted with ethyl acetate. The organic layer was washed with saturated sodium chloride solution, dried with anhydrous magnesium sulfate, and concentrated. The residue was combined with the previously collected crystals, followed by recrystallization, which afforded 8.4 g (yield, 38%) of 2-amino-2-(4-fluorophenyl)acetamide.

REFERENCE PRODUCTION EXAMPLE 4

(1) A mixture of 18.5 g of sodium cyanide, 23 ml of concentrated ammonia water (28%), 24 ml of water, and 27.6 g of ammonium chloride was stirred at 15° C. for 1 hour, to which 18 ml of ether was added at the same temperature. The reaction mixture was cooled to 2.5° to 4° C., to which 50 g of 4-chloro-2-fluorobenzaldehyde was added at the same temperature. Then, ammonia gas was bubbled into the reaction mixture at −0.5° to 1° C. for 3 hours, and the reaction mixture was stirred at the same temperature for 2 hours and then at room temperature overnight.

After completion of the reaction, the reaction mixture was extracted with ether, and the organic layer was washed with water and then saturated sodium chloride solution, dried with anhydrous magnesium sulfate, and concentrated. The residue was subjected to silica gel column chromatography, which afforded 32.9 g (yield, 57%) of 2-amino-2-(4-chloro-2-fluorophenyl)acetonitrile.

$^1$H-NMR (CDCl$_3$/TMS, 250 MHz, δ (ppm)) 1.5–1.7 (br, 1H), 1.9–2.1 (br, 1H), 5.0–5.1 (br, 1H), 7.16 (d, 1H, J=10.2 Hz), 7.22 (dd, 1H, J=8.2 Hz, 2.7 Hz), 7.51 (dd, 1H, J=8.2 Hz, 8.0 Hz)

(2) Then, 20 g of concentrated sulfuric acid was added to 1.03 g of water, to which 17 g of 2-amino-2-(4-chloro-2-fluorophenyl)acetonitrile was added under ice cooling, and the mixture was heated at 50° to 60° C. under stirring for 3 hours. After completion of the reaction, the reaction mixture was poured into 100 ml of concentrated ammonia water cooled with ice in such a manner that the temperature of the solution became not higher than 20° C. The precipitated crystals were collected by filtration, and the filtrate was extracted with ethyl acetate. The organic layer was washed with saturated sodium chloride solution, dried with anhydrous magnesium sulfate, and concentrated. The residue was combined with the previously collected crystals, followed by recrystallization, which afforded 15.3 g (yield, 82%) of 2-amino-2-(4-chloro-2-fluorophenyl)acetamide.

$^1$H-NMR (CDCl$_3$/TMS, 250 MHz, δ (ppm)) 1.7–2.0 (br, 2H), 4.70 (s, 1H), 5.8–6.0 (br, 1H), 6.9–7.1 (br, 1H), 7.10 (d, 1H, J=10.2 Hz), 7.15 (dd, 1H, J=6.5 Hz, 2.2 Hz), 7.31 (dd, 1H, J=8.6 Hz, 6.5 Hz)

REFERENCE PRODUCTION EXAMPLE 5

(1) A mixture of 33.6 g of sodium cyanide, 50 ml of concentrated ammonia water (28%), 40 ml of water, and 50.1 g of ammonium chloride was stirred at 15° C. for 1 hour, to which 33 ml of ether was added at the same temperature. The reaction mixture was cooled to 2.5° to 4° C., to which 100 g of 2,4-dichlorobenzaldehyde was added at the same temperature. Then, ammonia gas was bubbled into the reaction mixture at −0.5° to 1° C. for 3 hours, and the reaction mixture was stirred at the same temperature for 2 hours and then at room temperature overnight.

After completion of the reaction, the reaction mixture was extracted with ether, and the organic layer was washed with water and then saturated sodium chloride solution, dried with anhydrous magnesium sulfate, and concentrated. The precipitated crystals were recrystallized, which afforded 97.5 g (yield, 85%) of 2-amino-2-(2,4-dichlorophenyl)acetonitrile, m.p. 70.8° C.

(2) Then, 11.2 g of concentrated sulfuric acid was added to 0.54 g of water, to which 10.1 g of 2-amino-2-(2,4-dichlorophenyl)acetonitrile was added under ice cooling, and the mixture was heated at 50° to 60° C. under stirring for 3 hours. After completion of the reaction, the reaction mixture was poured into 30 ml of concentrated ammonia water cooled with ice in such a manner that the temperature of the solution became not higher than 20° C. The precipitated crystals were collected by filtration, and the filtrate was extracted with ethyl acetate. The organic layer was washed with saturated sodium chloride solution, dried with anhydrous magnesium sulfate, and concentrated. The residue was combined with the previously collected crystals, followed by recrystallization, which afforded 6.14 g (yield, 57%) of 2-amino-2-(2,4-dichlorophenyl)acetamide, m.p. 113.8° C.

REFERENCE PRODUCTION EXAMPLE 6

(1) To a mixture of 37 g of concentrated sulfuric acid and 141 ml of water was added dropwise a solution of 34.4 g of 2,4-dichloro-5-methoxyaniline in 28 ml of diethyl ether at room temperature, and the mixture was stirred at 40° to 50° C. for 50 minutes. The diethyl ether was distilled out at the same temperature, and the reaction mixture was cooled to 0° C., to which a solution of 13.8 g of sodium nitrite in 31 ml of water was added at such a rate that the temperature of the reaction system was kept not higher than 10° C. Then, taking care that the reaction mixture had no temperature rise, the reaction mixture was filtered through celite. The filtrate was added dropwise to a solution of 59.5 g of potassium iodide in 95 ml of water at such a rate that the temperature of the reaction system was kept not higher than 10° C. At the same time, 100 ml of hexane and 100 ml of diethyl ether were added, and the mixture was stirred at the same temperature for 2 hours. After completion of the reaction, the reaction mixture was extracted with diethyl ether. The organic layer was washed with saturated sodium thiosulfate solution, dried with anhydrous magnesium sulfate, and concentrated. The residue was subjected to silica gel column chromatography, which afforded 22.6 g (yield, 41%) of 2,4-dichloro-5-iodo-1-methoxybenzene.

$^1$H-NMR (CDCl$_3$/TMS, 300 MHz, δ (ppm)) 3.88 (s, 3H), 7.32 (s, 1H), 7.43 (s, 1H)

(2) A mixture of 22.6 g of 2,4-dichloro-5-iodo-1-methoxybenzene, 7.61 g of sodium formate, 1.05 g of dichlorobis(triphenylphosphine) palladium, and 60 ml of N,N-dimethylformamide was stirred, while bubbling carbon monoxide at 90° to 100° C. over 12 hours. After completion of the reaction, the reaction mixture was returned to room temperature, followed by dilution with diluted hydrochloride, and the mixture was extracted with ethyl acetate. The organic layer was washed with saturated sodium chloride solution, dried with anhydrous magnesium sulfate, and concentrated. The residue was subjected to silica gel column chromatography, which afforded 6.75 g (yield, 44%) of 2,4-dichloro-5-methoxybenzaldehyde.

$^1$H-NMR (CDCl$_3$/TMS, 300 MHz, δ (ppm)) 3.95 (s, 3H), 7.44 (s, 1H), 7.49 (s, 1H), 10.39 (s, 1H)

(3) A mixture of 3.86 g of sodium cyanide, 5.74 ml of concentrated ammonia water (28%), 4.65 ml of water, and 5.78 g of ammonium chloride was stirred at 15° C. for 1 hour, to which 3.8 ml of ether was added at the same temperature. The reaction mixture was cooled to 2.5° to 4° C., to which a solution of 13.5 g of 2,4-dichloro-5-methoxybenzaldehyde in 40 ml of methanol was added at the same temperature. Then, ammonia gas was bubbled into the reaction mixture at −0.5° to 1° C. for 3 hours, and the reaction mixture was stirred at the same temperature for 2 hours and then at room temperature overnight.

After completion of the reaction, the reaction mixture was extracted with ether, and the organic layer was washed with water and then saturated sodium chloride solution, dried with anhydrous magnesium sulfate, and concentrated. The precipitated crystals were recrystallized, which afforded 15.0 g (yield, 99%) of 2-amino-2-(2,4-dichloro-5-methoxy)acetonitrile.

$^1$H-NMR (CDCl$_3$/TMS, 300 MHz, δ (ppm)) 1.99 (d, 2H, J=6.7 Hz), 3.96 (s, 3H), 5.21 (t, 1H, J=6.7 Hz), 7.22 (s, 1H), 7.45 (s, 1H)

(4) Then, 3.6 g of concentrated sulfuric acid was added to 0.33 g of water, to which 15.0 g of 2-amino-2-(2,4-dichloro-5-methoxyphenyl)acetonitrile was added under ice cooling, and the mixture was heated at 50° to 60° C. under stirring for 3 hours. After completion of the reaction, the reaction mixture was poured into 15 ml of concentrated ammonia water cooled with ice in such a manner that the temperature of the solution became not higher than 20° C. The precipitated crystals were collected by filtration, and the filtrate was extracted with ethyl acetate. The organic layer was washed with saturated sodium chloride solution, dried with anhydrous magnesium sulfate, and concentrated. The residue was combined with the previously collected crystals, followed by recrystallization, which afforded 7.42 g (yield, 46%) of 2-amino-2-(2,4-dichloro-5-methoxyphenyl)acetamide.

$^1$H-NMR (CDCl$_3$/TMS, 300 MHz, δ (ppm)) 3.90 (s, 3H), 4.85 (s, 1H), 6.97 (s, 1H), 7.41 (s, 1H)

Examples of compound [2] as an intermediate compound for the production of the present compounds are shown with their compound numbers in Tables 6 to 8.

TABLE 6

Compounds of the formula:

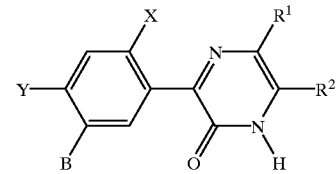

| Compound No. | X | Y | R$^1$ | R$^2$ | B |
|---|---|---|---|---|---|
| 1-1001 | H | F | H | CF$_3$ | H |
| 1-1002 | H | Cl | H | CF$_3$ | H |
| 1-1003 | H | Br | H | CF$_3$ | H |
| 1-1004 | F | F | H | CF$_3$ | H |
| 1-1005 | F | Cl | H | CF$_3$ | H |
| 1-1006 | F | Br | H | CF$_3$ | H |
| 1-1007 | Cl | Cl | H | CF$_3$ | H |
| 1-1008 | F | Cl | H | CF$_3$ | OCH$_3$ |
| 1-1009 | Cl | Cl | H | CF$_3$ | OCH$_3$ |
| 1-1010 | H | F | CH$_3$ | CF$_3$ | H |
| 1-1011 | H | Cl | CH$_3$ | CF$_3$ | H |
| 1-1012 | H | Br | CH$_3$ | CF$_3$ | H |
| 1-1013 | F | F | CH$_3$ | CF$_3$ | H |
| 1-1014 | F | Cl | CH$_3$ | CF$_3$ | H |
| 1-1015 | F | Br | CH$_3$ | CF$_3$ | H |
| 1-1016 | F | Cl | CH$_3$ | CF$_3$ | OCH$_3$ |
| 1-1017 | Cl | Cl | CH$_3$ | CF$_3$ | H |
| 1-1018 | Cl | Cl | CH$_3$ | CF$_3$ | OCH$_3$ |

TABLE 7

Compounds of the formula:

$$\text{[structure with X, Y, Z}^2\text{, R}^1\text{, R}^2\text{, R}^6\text{]}$$

| Compound No. | X | Y | Z² | R¹ | R² | R⁶ |
|---|---|---|---|---|---|---|
| 3-1001 | H | F | O | H | CF₃ | CH₃ |
| 3-1002 | H | Cl | O | H | CF₃ | CH₃ |
| 3-1003 | H | Br | O | H | CF₃ | CH₃ |
| 3-1004 | F | F | O | H | CF₃ | CH₃ |
| 3-1005 | F | Cl | O | H | CF₃ | CH₃ |
| 3-1006 | F | Br | O | H | CF₃ | CH₃ |
| 3-1007 | H | F | O | H | CF₃ | C₂H₅ |
| 3-1008 | H | Cl | O | H | CF₃ | C₂H₅ |
| 3-1009 | H | Br | O | H | CF₃ | C₂H₅ |
| 3-1010 | F | F | O | H | CF₃ | C₂H₅ |
| 3-1011 | F | Cl | O | H | CF₃ | C₂H₅ |
| 3-1012 | F | Br | O | H | CF₃ | C₂H₅ |

TABLE 8

Compounds of the formula:

$$\text{[structure with X, Y, R}^1\text{, R}^2\text{, R}^7\text{, R}^8\text{]}$$

| Compound No. | X | Y | R¹ | R² | R⁷ | R⁸ |
|---|---|---|---|---|---|---|
| 4-1001 | H | F | H | CF₃ | H | CH₃ |
| 4-1002 | H | Cl | H | CF₃ | H | CH₃ |
| 4-1003 | H | Br | H | CF₃ | H | CH₃ |
| 4-1004 | H | F | H | CF₃ | H | CH₂OH |
| 4-1005 | H | Cl | H | CF₃ | H | CH₂OH |
| 4-1006 | H | Br | H | CF₃ | H | CH₂OH |
| 4-1007 | H | F | H | CF₃ | CH₃ | CH₃ |
| 4-1008 | H | Cl | H | CF₃ | CH₃ | CH₃ |
| 4-1009 | H | Br | H | CF₃ | CH₃ | CH₃ |
| 4-1010 | H | F | H | CF₃ | CH₃ | CH₂OH |
| 4-1011 | H | Cl | H | CF₃ | CH₃ | CH₂OH |
| 4-1012 | H | Br | H | CF₃ | CH₃ | CH₂OH |
| 4-1013 | F | F | H | CF₃ | H | CH₃ |
| 4-1014 | F | Cl | H | CF₃ | H | CH₃ |
| 4-1015 | F | Br | H | CF₃ | H | CH₃ |
| 4-1016 | F | F | H | CF₃ | H | CH₂OH |
| 4-1017 | F | Cl | H | CF₃ | H | CH₂OH |
| 4-1018 | F | Br | H | CF₃ | H | CH₂OH |
| 4-1019 | F | F | H | CF₃ | CH₃ | CH₃ |
| 4-1020 | F | Cl | H | CF₃ | CH₃ | CH₃ |
| 4-1021 | F | Br | H | CF₃ | CH₃ | CH₃ |
| 4-1022 | F | F | H | CF₃ | CH₃ | CH₂OH |
| 4-1023 | F | Cl | H | CF₃ | CH₃ | CH₂OH |
| 4-1024 | F | Br | H | CF₃ | CH₃ | CH₂OH |

The following will describe formulation examples, in which the present compounds are designated by their compound numbers shown in Tables 1 to 5 and parts are by weight.

FORMULATION EXAMPLE 1

Fifty parts of each of compounds 1-1 to 1-581, 2-1 to 2-242, 3-1 to 3-128, 4-1 to 4-137, and 5-1 to 5-17, 3 parts of calcium ligninsulfonate, 2 parts of sodium laurylsulfate, and 45 parts of synthetic hydrated silicon oxide are well pulverized and mixed to give a wettable powder for each compound.

FORMULATION EXAMPLE 2

Ten parts of each of compounds 1-1 to 1-581, 2-1 to 2-242, 3-1 to 3-128, 4-1 to 4-137, and 5-1 to 5-17, 14 parts of polyoxyethylene styryl phenyl ether, 6 parts of calcium dodecylbenzenesulfonate, 35 parts of xylene, and 35 parts of cyclohexanone are well mixed to give an emulsifiable concentrate for each compound.

FORMULATION EXAMPLE 3

Two parts of each of compounds 1-1 to 1-581, 2-1 to 2-242, 3-1 to 3-128, 4-1 to 4-137, and 5-1 to 5-17, 2 parts of synthetic hydrated silicon oxide, 2 parts of calcium ligninsulfonate, 30 parts of bentonite, and 64 parts of kaoline clay are well pulverized and mixed, to which water is added, and the mixture is well kneaded, granulated, and dried to give a granule for each compound.

FORMULATION EXAMPLE 4

Twenty-five parts of each of compounds 1-1 to 1-581, 2-1 to 2-242, 3-1 to 3-128, 4-1 to 4-137, and 5-1 to 5-17, 50 parts of 10% aqueous polyvinyl alcohol solution, and 25 parts of water are mixed, and the mixture is pulverized until the average particle size becomes 5 μm or less to give a flowable for each compound.

FORMULATION EXAMPLE 5

Five parts of each of compounds 1-1 to 1-581, 2-1 to 2-242, 3-1 to 3-128, 4-1 to 4-137, and 5-1 to 5-17 was added to 40 parts of 10% aqueous polyvinyl alcohol solution and dispersed by emulsion with a homogenizer until the mean particle size becomes 10 μm or less, to which 55 parts of water is added to give a concentrated emulsion for each compound.

The following test examples will demonstrate that the present compounds are useful as active ingredients of herbicides. The present compounds are designated by their compound numbers shown in Tables 1 to 5.

The herbicidal activity was evaluated at 6 levels with indices of 0 to 5, i.e., designated by the numeral "0", "1", "2", "3", "4" or "5", wherein "0" means that there was no or little difference in the degree of germination or growth between the treated and the untreated test plants at the time of examination, and "5" means that the test plants died complete or their germination or growth was completely inhibited. The herbicidal activity is excellent when rated at "4" or "5" but insufficient when rated at "3" or lower.

TEST EXAMPLE 1

Foliar Treatment on Upland Fields

Cylindrical plastic pots of 10 cm in diameter and 10 cm in depth were filled with soil, in which the seeds of velvetleaf (*Abutilon theophrasti*) and ivyleaf morningglory (*Ipomoea hederacea*) were sowed, and the test plants were grown in a greenhouse for 15 days. Each of the test compounds listed below was formulated into an emulsifiable concentrate according to Formulation Example 2, which was diluted with water containing a spreading agent to a prescribed concentration. The dilution was uniformly sprayed over the foliage of the test plants with a sprayer at a volume of 1000 liters per hectare. After the application, the test plants were grown in the greenhouse for 19 days, and the herbicidal activity was examined. The results are shown in Table 9.

TABLE 9

| Test compound | Application amount of active ingredient (g/ha) | Herbicidal activity Velvetleaf | Ivyleaf morningglory |
|---|---|---|---|
| 1-10 | 2000 | 5 | 5 |
| 1-11 | 2000 | 5 | 5 |
| 1-17 | 2000 | 5 | 5 |
| 1-37 | 2000 | 5 | 5 |
| 1-61 | 2000 | 5 | 5 |
| 1-90 | 2000 | 5 | 5 |
| 1-144 | 2000 | 5 | 5 |
| 1-156 | 2000 | 5 | 5 |
| 1-157 | 2000 | 5 | 5 |
| 1-165 | 2000 | 5 | 5 |
| 1-166 | 2000 | 5 | 5 |
| 1-167 | 2000 | 5 | 5 |
| 1-169 | 2000 | 5 | 5 |
| 1-173 | 2000 | 5 | 5 |
| 1-174 | 2000 | 5 | 5 |
| 1-332 | 2000 | 5 | 5 |
| 1-336 | 2000 | 5 | 5 |
| 1-343 | 2000 | 5 | 5 |
| 1-346 | 2000 | 5 | 5 |
| 1-351 | 2000 | 5 | 5 |
| 1-355 | 2000 | 5 | 5 |
| 1-356 | 2000 | 5 | 5 |
| 1-358 | 2000 | 5 | 5 |
| 1-370 | 2000 | 5 | 5 |
| 1-371 | 2000 | 5 | 5 |
| 1-380 | 2000 | 5 | 5 |
| 1-387 | 2000 | 5 | 5 |
| 2-13 | 2000 | 5 | 5 |
| 2-61 | 2000 | 5 | 5 |

TEST EXAMPLE 2

Soil Surface Treatment on Upland Fields

Cylindrical plastic pots of 10 cm in diameter and 10 cm in depth were filled with soil, in which the seeds of velvetleaf (*Abutilon theophrasti*) and ivyleaf morningglory (*Ipomoea hederacea*) were sowed. Each of the test compounds listed below was formulated into an emulsifiable concentrate according to Formulation Example 2, which was diluted with water to a prescribed concentration. The dilution was uniformly sprayed over the soil surface in the pots with a sprayer at a volume of 1000 liters per hectare. After the application, the test plants were grown in a greenhouse for 19 days, and the herbicidal activity was examined. The results are shown in Table 10.

TABLE 10

| Test compound | Application amount of active ingredient (g/ha) | Herbicidal activity Velvetleaf | Ivyleaf morningglory |
|---|---|---|---|
| 1-10 | 2000 | 5 | 5 |
| 1-11 | 2000 | 5 | 5 |

TABLE 10-continued

| Test compound | Application amount of active ingredient (g/ha) | Herbicidal activity Velvetleaf | Ivyleaf morningglory |
|---|---|---|---|
| 1-37 | 2000 | 5 | 5 |
| 1-90 | 2000 | 5 | 5 |
| 1-144 | 2000 | 5 | 5 |
| 1-156 | 2000 | 5 | 5 |
| 1-165 | 2000 | 5 | 5 |
| 1-166 | 2000 | 5 | 5 |
| 1-169 | 2000 | 5 | 5 |
| 1-174 | 2000 | 5 | 5 |
| 1-332 | 2000 | 5 | 5 |
| 1-336 | 2000 | 5 | 5 |
| 1-343 | 2000 | 5 | 5 |
| 1-358 | 2000 | 5 | 5 |
| 1-370 | 2000 | 5 | 5 |
| 1-371 | 2000 | 5 | 5 |
| 1-380 | 2000 | 5 | 5 |
| 2-13 | 2000 | 5 | 5 |
| 2-61 | 2000 | 5 | 5 |

TEST EXAMPLE 3

Flooding Treatment on Paddy Fields

Cylindrical plastic pots of 9 cm in diameter and 11 cm in depth were filled with soil, in which the seeds of barnyardgrass (*Echinochloa oryzicola*) were sowed. These pots were flooded to form a paddy field, and the test plants were grown in a greenhouse for 7 days. Each of the test compounds listed below was formulated into an emulsifiable concentrate according to Formulation Example 2, which was diluted with water to a prescribed concentration. The dilution was applied to the water surface in the pots at a volume of 50 liters per are. After the application, the test plants were grown in the greenhouse for 19 days, and the herbicidal activity was examined. The results are shown in Table 11.

TABLE 11

| Test compound | Application amount of active ingredient (g/ha) | Herbicidal activity Barnyardgrass |
|---|---|---|
| 1-10 | 4000 | 5 |
| 1-11 | 4000 | 5 |
| 1-17 | 4000 | 5 |
| 1-37 | 4000 | 5 |
| 1-61 | 4000 | 5 |
| 1-90 | 4000 | 5 |
| 1-144 | 4000 | 5 |
| 1-156 | 4000 | 5 |
| 1-157 | 4000 | 5 |
| 1-165 | 4000 | 5 |
| 1-166 | 4000 | 5 |
| 1-167 | 4000 | 5 |
| 1-169 | 4000 | 5 |
| 1-173 | 4000 | 5 |
| 1-174 | 4000 | 5 |
| 1-332 | 4000 | 5 |
| 1-336 | 4000 | 5 |
| 1-343 | 4000 | 5 |
| 1-346 | 4000 | 5 |
| 1-351 | 4000 | 5 |
| 1-355 | 4000 | 5 |
| 1-356 | 4000 | 5 |
| 1-358 | 4000 | 5 |
| 1-370 | 4000 | 5 |
| 1-371 | 4000 | 5 |
| 1-380 | 4000 | 5 |
| 1-387 | 4000 | 5 |
| 2-1 | 4000 | 5 |
| 2-13 | 4000 | 5 |

TABLE 11-continued

| Test compound | Application amount of active ingredient (g/ha) | Herbicidal activity Barnyardgrass |
|---|---|---|
| 2-61 | 4000 | 5 |

We claim:

1. A compound of the formula:

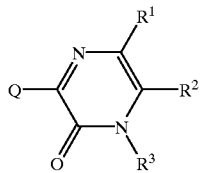
(1)

wherein $R^1$ is hydrogen or $C_1$–$C_3$ alkyl; $R^2$ is $C_1$–$C_3$ haloalkyl; $R^3$ is $C_1$–$C_6$ alkyl optionally substituted with one or more halogen atoms; $C_3$–$C_6$ alkenyl, or $C_3$–$C_6$ alkynyl; and Q is (Q-1), (Q-2), (Q-3), (Q-4), or (Q-5) of the formula:

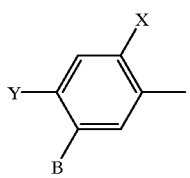
(Q-1)

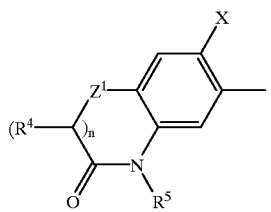
(Q-2)

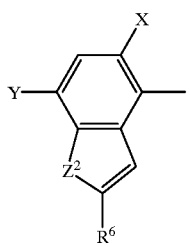
(Q-3)

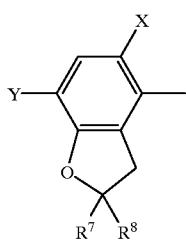
(Q-4)

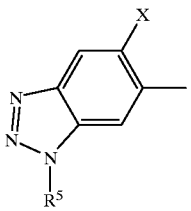
(Q-5)

wherein X is hydrogen or halogen;
Y is halogen, nitro, cyano, or trifluoromethyl;
$Z^1$ is oxygen, sulfur, NH, or methylene;
$Z^2$ is oxygen or sulfur;
n is 0 or 1;
B is hydrogen, halogen, nitro, cyano, chlorosulfonyl, —$OR^{10}$, —$SR^{10}$, —$SO_2OR^{10}$, —$N(R^{10})R^{11}$, —$SO_2N(R^{11})R^{12}$, —$NR^{11}(COR^{13})$, —$NR^{11}(SO_2R^{14})(SO_2R^{15})$, —$N(SO_2R^{14})(COR^{13})$, —$NR^{11}(COOR^{13})$, —$COOR^{13}$, —$CON(R^{11})R^{12}$, —$CSN(R^{11})R^{12}$, —$COR^{16}$, —$CR^{17}$=$CR^{18}CHO$, —$CR^{17}$=$CR^{18}COOR^{10}$, —$CR^{17}$=$CR^{18}CON(R^{11})R^{12}$, —$CH_2CHWCOOR^{13}$, or —$CH_2CHWCON(R^{11})R^{12}$;
$R^4$ is hydrogen or $C_1$–$C_3$ alkyl;
$R^5$ is hydrogen, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_3$–$C_8$ alkoxyalkoxyalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{11})R^{12}$, —$CH_2COON(R^{11})R^{12}$, —$CH(C_1$–$C_4$ alkyl)CON($R^{11}$)$R^{12}$, —$CH(C_1$–$C_4$ alkyl)COON($R^{11}$)$R^{12}$, $C_2$–$C_8$ alkylthioalkyl, $C_1$–$C_6$ alkylsulfonyl, $C_1$–$C_6$ haloalkylsulfonyl, ($C_1$–$C_8$ alkyl)carbonyl, ($C_1$–$C_8$ alkoxy)carbonyl, or hydroxy $C_1$–$C_6$ alkyl;
$R^6$ is $C_1$–$C_6$ alkyl, $C_1$–$C_6$ haloalkyl, formyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, ($C_1$–$C_6$ alkoxy)carbonyl, or ($C_1$–$C_6$ alkyl)carbonyl;
$R^7$ is hydrogen or $C_1$–$C_3$ alkyl; and
$R^8$ is $C_1$–$C_6$ alkyl, $C_1$–$C_6$ haloalkyl, hydroxy $C_1$–$C_6$ alkyl, $C_2$–$C_8$ alkoxyalkyl, $C_3$–$C_{10}$ alkoxyalkoxyalkyl, ($C_1$–$C_5$ alkyl)carbonyloxy $C_1$–$C_6$ alkyl, ($C_1$–$C_6$ haloalkyl)carbonyloxy $C_1$–$C_6$ alkyl, carboxyl, carboxy $C_1$–$C_6$ alkyl, ($C_1$–$C_8$ alkoxy)carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, aminocarbonyl, ($C_1$–$C_6$ alkyl)aminocarbonyl, di($C_1$–$C_6$ alkyl)aminocarbonyl, ($C_1$–$C_6$ alkyl)aminocarbonyloxy $C_1$–$C_6$ alkyl, or di($C_1$–$C_6$ alkyl)aminocarbonyloxy $C_1$–$C_6$ alkyl;
wherein W is hydrogen, chlorine, or bromine;
$R^{10}$ is hydrogen, $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{11})R^{12}$, —$CH_2COON(R^{11})R^{12}$, —CH($C_1$–$C_4$ alkyl)CON ($R^{11}$)$R^{12}$, or —CH($C_1$–$C_4$ alkyl)COON($R^{11}$)$R^{12}$;

$R^{11}$ and $R^{12}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, or {($C_1$–$C_4$ alkoxy)$C_1$–$C_4$ alkoxy}carbonyl $C_1$–$C_6$ alkyl, or $R^{11}$ and $R^{12}$ are combined together to form tetramethylene, pentamethylene, or ethyleneoxyethylene;

$R^{13}$ is hydrogen, $C_1$–$C_6$ alkyl, $C_1$–$C_6$ haloalkyl, or $C_3$–$C_8$ cycloalkyl;

$R^{14}$ and $R^{15}$ are independently $C_1$–$C_6$ alkyl, $C_1$–$C_6$ haloalkyl, or phenyl optionally substituted with methyl or nitro;

$R^{16}$ is hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_8$ alkoxyalkyl, or hydroxy $C_1$–$C_6$ alkyl; and $R^{17}$ and $R^{18}$ are independently hydrogen or $C_1$–$C_6$ alkyl.

2. A compound according to claim 1, wherein Q is [Q-1], [Q-2], [Q-3], or [Q-4];

Y is halogen;

$Z^1$ is oxygen or sulfur;

$Z^2$ is oxygen;

B is hydrogen, nitro, —$OR^{10}$, —$SR^{10}$, —$NHR^{10}$, —$NHSO_2R^{14}$, —$COOR^{13}$, or —$CH_2CHWCOOR^{13}$;

$R^5$ is $C_1$–$C_6$ alkyl, $C_3$–$C_6$ alkenyl, or $C_3$–$C_6$ alkynyl;

$R^6$ is $C_1$–$C_6$ alkyl, $C_1$–$C_6$ haloalkyl, formyl, hydroxymethyl, $C_1$–$C_6$ alkoxymethyl, $C_1$–$C_6$ alkylcarbonyloxymethyl, or $C_1$–$C_6$ alkoxycarbonyl;

$R^7$ is hydrogen or methyl; and $R^8$ is methyl, hydroxymethyl, $C_1$–$C_6$ alkoxymethyl, ($C_1$–$C_5$ alkyl)carbonyloxymethyl, carboxyl, or ($C_1$–$C_6$ alkoxy)carbonyl;

wherein W is hydrogen or chlorine;

$R^{10}$ is $C_1$–$C_6$ alkyl, $C_3$–$C_8$ cycloalkyl, $C_3$–$C_6$ alkenyl, $C_3$–$C_6$ haloalkenyl, $C_3$–$C_6$ alkynyl, cyano $C_1$–$C_6$ alkyl, or ($C_1$–$C_6$ alkoxy)carbonyl $C_1$–$C_6$ alkyl;

$R^{13}$ is $C_1$–$C_6$ alkyl; and $R^{14}$ is $C_1$–$C_6$ alkyl.

3. A compound according to claim 1 or 2, wherein $R^2$ is trifluoromethyl.

4. A compound according to claim 1, wherein Q is [Q-1].
5. A compound according to claim 1, wherein Q is [Q-2].
6. A compound according to claim 1, wherein Q is [Q-3].
7. A compound according to claim 1, wherein Q is [Q-4].
8. A compound according to claim 2, wherein Q is [Q-1].
9. A compound according to claim 2, wherein Q is [Q-2].
10. A compound according to claim 2, wherein Q is [Q-3].
11. A compound according to claim 2, wherein Q is [Q-4].
12. A compound according to claim 2, wherein Q is [Q-1] and $R^2$ is trifluoromethyl.
13. A compound according to claim 2, wherein Q is [Q-2] and $R^2$ is trifluoromethyl.
14. A compound according to claim 2, wherein Q is [Q-3] and $R^2$ is trifluoromethyl.
15. A compound according to claim 2, wherein Q is [Q-4] and $R^2$ is trifluoromethyl.
16. A compound according to claim 2, wherein Q is [Q-1]; $R^2$ is trifluoromethyl; and B is —$OR^{10}$.
17. A compound according to claim 2, wherein Q is [Q-1]; $R^2$ is trifluoromethyl; and B is —$NHR^{10}$.
18. A compound according to claim 2, wherein Q is [Q-1]; $R^2$ is trifluoromethyl; B is —$OR^{10}$; and $R^{10}$ is $C_3$–$C_6$ alkynyl.

19. A compound according to claim 2, wherein Q is [Q-1]; $R^2$ is trifluoromethyl; B is —$OR^{10}$; and $R^{10}$ is ($C_1$–$C_6$ alkoxy)carbonyl $C_1$–$C_6$ alkyl.

20. A compound according to claim 2, wherein Q is [Q-1]; $R^2$ is trifluoromethyl; B is —$OR^{10}$; and $R^{10}$ is 1-($C_1$–$C_6$ alkoxy)carbonylethyl.

21. A compound according to claim 2, wherein Q is [Q-1]; $R^2$ is trifluoromethyl; B is —$OR^{10}$; and $R^{10}$ is ($C_1$–$C_6$ alkoxy)carbonylmethyl.

22. A compound according to claim 2, wherein Q is [Q-1]; $R^2$ is trifluoromethyl; B is —$NHR^{10}$; and $R^{10}$ is ($C_1$–$C_6$ alkoxy)carbonyl $C_1$–$C_6$ alkyl.

23. A compound according to claim 2, wherein Q is [Q-2]; $R^2$ is trifluoromethyl; $Z^1$ is oxygen; n is 1; $R^4$ is hydrogen; and $R^5$ is $C_3$–$C_6$ alkynyl.

24. A compound according to claim 1, wherein $R^1$ is hydrogen; $R^2$ is trifluoromethyl; $R^3$ is methyl; Q is [Q-1]; X is fluorine; Y is chlorine; and B is hydrogen.

25. A compound according to claim 1, wherein $R^1$ is hydrogen; $R^2$ is trifluoromethyl; $R^3$ is methyl; Q is [Q-1]; X is fluorine; Y is chlorine; and B is propargyloxy.

26. A compound according to claim 1, wherein $R^1$ is hydrogen; $R^2$ is trifluoromethyl; $R^3$ is methyl; Q is (Q-1); X is chlorine; Y is chlorine; and B is 1-(ethoxycarbonyl)ethylamino.

27. A compound according to claim 1, wherein $R^1$ is hydrogen; $R^2$ is trifluoromethyl; $R^3$ is methyl; Q is [Q-2]; X is fluorine; $Z^1$ is oxygen; n is 1; $R^4$ is hydrogen; and $R^5$ is propargyl.

28. A process for producing a compound according to claim 1, which comprises reacting a compound of the formula:

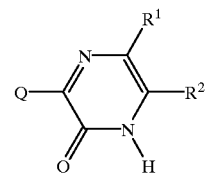

(2)

wherein $R^1$ is hydrogen or $C_1$–$C_3$ alkyl; $R^2$ is $C_1$–$C_3$ haloalkyl; and Q is (Q-1), (Q-2), (Q-3), (Q-4), or (Q-5) of the formula:

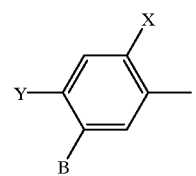

(Q-1)

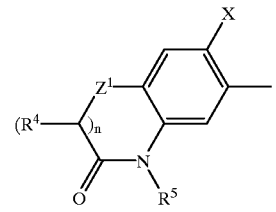

(Q-2)

-continued

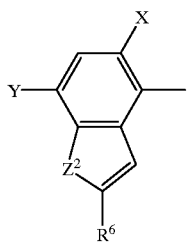
(Q-3)

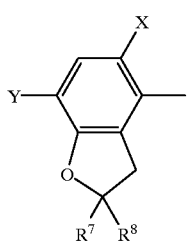
(Q-4)

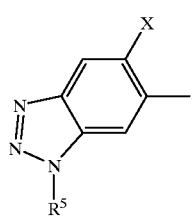
(Q-5)

wherein X is hydrogen or halogen;
Y is halogen, nitro, cyano, or trifluoromethyl;
$Z^1$ is oxygen, sulfur, NH, or methylene;
$Z^2$ is oxygen or sulfur;
n is 0 or 1;
B is hydrogen, halogen, nitro, cyano, chlorosulfonyl, —$OR^{10}$, —$SR^{10}$, —$SO_2OR^{10}$, —$N(R^{10})R^{11}$, —$SO_2N(R^{11})R^{12}$, —$NR^{11}(COR^{13})$, —$NR^{11}(SO_2R^{14})$, —$N(SO_2R^{14})(SO_2R^{15})$, —$N(SO_2R^{14})(COR^{13})$, —$NR^{11}(COOR^{13})$, —$COOR^{13}$, —$CON(R^{11})R^{12}$, —$CSN(R^{11})R^{12}$, —$COR^{16}$, —$CR^{17}$=$CR^{18}CHO$, —$CR^{17}$=$CR^{18}COOR^{10}$, —$CR^{17}$=$CR^{18}CON(R^{11})R^{12}$, —$CH_2CHWCOOR^{13}$, or —$CH_2CHWCON(R^{11})R^{12}$;
$R^4$ is hydrogen or $C_1$-$C_3$ alkyl;
$R^5$ is hydrogen, $C_1$-$C_6$ alkyl, $C_1$-$C_6$ haloalkyl, $C_3$-$C_6$ alkenyl, $C_3$-$C_6$ haloalkenyl, $C_3$-$C_6$ alkynyl, $C_3$-$C_6$ haloalkynyl, cyano $C_1$-$C_6$ alkyl, $C_2$-$C_8$ alkoxyalkyl, $C_3$-$C_8$ alkoxyalkoxyalkyl, carboxy $C_1$-$C_6$ alkyl, ($C_1$-$C_6$ alkoxy)carbonyl $C_1$-$C_6$ alkyl, {($C_1$-$C_4$ alkoxy) $C_1$-$C_4$ alkoxy}carbonyl $C_1$-$C_6$ alkyl, ($C_3$-$C_8$ cycloalkoxy)carbonyl $C_1$-$C_6$ alkyl, —$CH_2CON(R^{11})R^{12}$, —$CH_2COON(R^{11})R^{12}$, —$CH(C_1$-$C_4$ alkyl)$CON(R^{11})R^{12}$, —$CH(C_1$-$C_4$ alkyl)$COON(R^{11})R^{12}$, $C_2$-$C_8$ alkylthioalkyl, $C_1$-$C_6$ alkylsulfonyl, $C_1$-$C_6$ haloalkylsulfonyl, ($C_1$-$C_8$ alkyl)carbonyl, ($C_1$-$C_8$ alkoxy)carbonyl, or hydroxy $C_1$-$C_6$ alkyl;
$R^6$ is $C_1$-$C_6$ alkyl, $C_1$-$C_6$ haloalkyl, formyl, cyano, carboxyl, hydroxy $C_1$-$C_6$ alkyl, $C_1$-$C_6$ alkoxy $C_1$-$C_6$ alkyl, $C_1$-$C_6$ alkoxy $C_1$-$C_6$ alkoxy $C_1$-$C_6$ alkyl, ($C_1$-$C_6$ alkyl)carbonyloxy $C_1$-$C_6$ alkyl, ($C_1$-$C_6$ haloalkyl)carbonyloxy $C_1$-$C_6$ alkyl, ($C_1$-$C_6$ alkoxy)carbonyl, or ($C_1$-$C_6$ alkyl)carbonyl;
$R^7$ is hydrogen or $C_1$-$C_3$ alkyl; and $R^8$ is $C_1$-$C_6$ alkyl, $C_1$-$C_6$ haloalkyl, hydroxy $C_1$-$C_6$ alkyl, $C_2$-$C_8$ alkoxyalkyl, $C_3$-$C_{10}$ alkoxyalkoxyalkyl, ($C_1$-$C_5$ alkyl)carbonyloxy $C_1$-$C_6$ alkyl, ($C_1$-$C_6$ haloalkyl)carbonyloxy $C_1$-$C_6$ alkyl, carboxyl, carboxy $C_1$-$C_6$ alkyl, ($C_1$-$C_8$ alkoxy)carbonyl, ($C_1$-$C_6$ haloalkoxy)carbonyl, ($C_3$-$C_{10}$ cycloalkoxy)carbonyl, ($C_3$-$C_8$ alkenyloxy)carbonyl, $C_3$-$C_8$ alkynyloxy)carbonyl, aminocarbonyl, ($C_1$-$C_6$ alkyl)aminocarbonyl, di($C_1$-$C_6$ alkyl)aminocarbonyl, ($C_1$-$C_6$ alkyl)aminocarbonyloxy $C_1$-$C_6$ alkyl, or di($C_1$-$C_6$ alkyl)aminocarbonyloxy $C_1$-$C_6$ alkyl;

wherein W is hydrogen, chlorine, or bromine;

$R^{10}$ is hydrogen, $C_1$-$C_6$ alkyl, $C_1$-$C_6$ haloalkyl, $C_3$-$C_8$ cycloalkyl, $C_3$-$C_6$ alkenyl, $C_3$-$C_6$ haloalkenyl, $C_3$-$C_6$ alkynyl, $C_3$-$C_6$ haloalkynyl, cyano $C_1$-$C_6$ alkyl, $C_2$-$C_8$ alkoxyalkyl, $C_2$-$C_8$ alkylthioalkyl, carboxy $C_1$-$C_6$ alkyl, ($C_1$-$C_6$ alkoxy)carbonyl $C_1$-$C_6$ alkyl, {($C_1$-$C_4$ alkoxy) $C_1$-$C_4$ alkoxy}carbonyl $C_1$-$C_6$ alkyl, ($C_3$-$C_8$ cycloalkoxy)carbonyl $C_1$-$C_6$ alkyl, —$CH_2CON(R^{11})R^{12}$, —$CH_2COON(R^{11})R^{12}$, —$CH(C_1$-$C_4$ alkyl)$CON(R^{11})R^{12}$, or —$CH(C_1$-$C_4$ alkyl)$COON(R^{11})R^{12}$;

$R^{11}$ and $R^{12}$ are independently hydrogen, $C_1$-$C_6$ alkyl, $C_1$-$C_6$ haloalkyl, $C_3$-$C_6$ alkenyl, $C_3$-$C_6$ alkynyl, cyano $C_1$-$C_6$ alkyl, $C_2$-$C_8$ alkoxyalkyl, $C_2$-$C_8$ alkylthioalkyl, carboxy $C_1$-$C_6$ alkyl, ($C_1$-$C_6$ alkoxy)carbonyl $C_1$-$C_6$ alkyl, or {($C_1$-$C_4$ alkoxy) $C_1$-$C_4$ alkoxy}carbonyl $C_1$-$C_6$ alkyl, or $R^{11}$ and $R^{12}$ are combined together to form tetramethylene, pentamethylene, or ethyleneoxyethylene;

$R^{13}$ is hydrogen, $C_1$-$C_6$ alkyl, $C_1$-$C_6$ haloalkyl, or $C_3$-$C_8$ cycloalkyl;

$R^{14}$ and $R^{15}$ are independently $C_1$-$C_6$ alkyl, $C_1$-$C_6$ haloalkyl, or phenyl optionally substituted with methyl or nitro;

$R^{16}$ is hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_2$-$C_8$ alkoxyalkyl, or hydroxy $C_1$-$C_6$ alkyl; and $R^{17}$ and $R^{18}$ are independently hydrogen or $C_1$-$C_6$ alkyl, with a compound of the formula:

$$R^3\text{—D} \qquad (3)$$

wherein $R^3$ is $C_1$-$C_6$ alkyl optionally substituted with one or more halogen atoms; $C_3$-$C_6$ alkenyl, or $C_3$-$C_6$ alkynyl; D is chlorine, bromine, iodine, methanesulfonyloxy, trifluoromethanesulfonyloxy, or p-toluenesulfonyloxy.

29. A herbicidal composition comprising, as an active ingredient, a herbicidally effective amount of the compound according to claim 1, and an inert carrier or diluent.

30. A method for controlling unfavorable weeds, which comprises applying a herbicidally effective amount of the compound according to claim 1 to an area where the unfavorable weeds grow or will grow.

31. A compound of the formula:

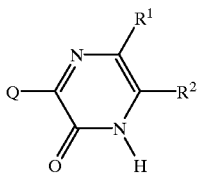

(2)

wherein $R^1$ is hydrogen or $C_1$–$C_3$ alkyl; $R^2$ is $C_1$–$C_3$ haloalkyl; and Q is (Q-1), (Q-2), (Q-3), (Q-4), or (Q-5) of the formula:

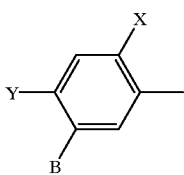

(Q-1)

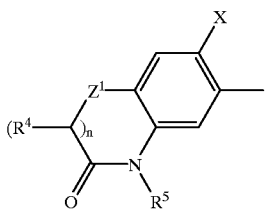

(Q-2)

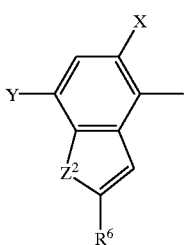

(Q-3)

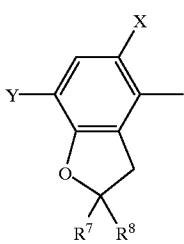

(Q-4)

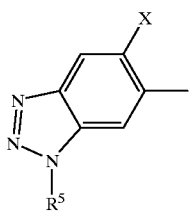

(Q-5)

wherein X is hydrogen or halogen;
Y is halogen, nitro, cyano, or trifluoromethyl;
$Z^1$ is oxygen, sulfur, NH, or methylene;
$Z^2$ is oxygen or sulfur;
n is 0 or 1;

B is hydrogen, halogen, nitro, cyano, chlorosulfonyl, —$OR^{10}$, —$SR^{10}$, —$SO_2OR^{10}$, —$N(R^{10})R^{11}$, —$SO_2N(R^{11})R^{12}$, —$NR^{11}(COR^{13})$, —$NR^{11}(SO_2NR^{14})$, —$N(SO_2N(R^{14})(SO_2N(R^{15}))$, —$N(SO_2R^{14})(COR^{13})$, —$NR^{11}(COOR^{13})$, —$COOR^{13}$, —$CON(R^{11})R^{12}$, —$CSN(R^{11})R^{12}$, —$COR^{16}$, —$CR^{17}$=$CR^{18}CHO$, —$CR^{17}$=$CR^{18}COOR^{10}$, —$CR^{17}$=$CR^{18}CON(R^{11})R^{12}$, —$CH_2CHWCOOR^{13}$, or —$CH_2CHWCON(R^{11})R^{12}$;

$R^4$ is hydrogen or $C_1$–$C_3$ alkyl;

$R^5$ is hydrogen, $C_1$–$C_6$ alkyl, $C_1$–$C_6$ haloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_3$–$C_8$ alkoxyalkoxyalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{11})R^{12}$, —$CH_2COON(R^{11})R^{12}$, —$CH(C_1$–$C_4$ alkyl)CON(R^{11})R^{12}$, —$CH(C_1$–$C_4$ alkyl)COON(R^{11})R^{12}$, $C_2$–$C_8$ alkylthioalkyl, $C_1$–$C_6$ alkylsulfonyl, $C_1$–$C_6$ haloalkylsulfonyl, ($C_1$–CS alkyl)carbonyl, ($C_1$–$C_8$ alkoxy)carbonyl, or hydroxy $C_1$–$C_6$ alkyl;

$R^6$ is $C_1$–$C_6$ alkyl, $C_1$–$C_6$ haloalkyl, formyl, cyano, carboxyl, hydroxy $C_1$–$C_6$ alkyl, $C_1$–$C_6$ alkoxy $C_1$–$C_6$ alkyl, $C_1$–$C_6$ alkoxy $C_1$–$C_6$ alkoxy $C_1$–$C_6$ alkyl, ($C_1$–$C_6$ alkyl)carbonyloxy $C_1$–$C_6$ alkyl, ($C_1$–$C_6$ haloalkyl)carbonyloxy $C_1$–$C_6$ alkyl, ($C_1$–$C_6$ alkoxy)carbonyl, or ($C_1$–$C_6$ alkyl)carbonyl;

$R^7$ is hydrogen or $C_1$–$C_3$ alkyl; and $R^8$ is $C_1$–$C_6$ alkyl, $C_1$–$C_6$ haloalkyl, hydroxy $C_1$–$C_6$ alkyl, $C_2$–$C_8$ alkoxyalkyl, $C_3$–$C_{10}$ alkoxyalkoxyalkyl, ($C_1$–$C_5$ alkyl)carbonyloxy $C_1$–$C_6$ alkyl, ($C_1$–$C_6$ haloalkyl)carbonyloxy $C_1$–$C_6$ alkyl, carboxyl, carboxy $C_1$–$C_6$ alkyl, ($C_1$–$C_8$ alkoxy)carbonyl, ($C_1$–$C_6$ haloalkoxy)carbonyl, ($C_3$–$C_{10}$ cycloalkoxy)carbonyl, ($C_3$–$C_8$ alkenyloxy)carbonyl, ($C_3$–$C_8$ alkynyloxy)carbonyl, aminocarbonyl, ($C_1$–$C_6$ alkyl)aminocarbonyl, di($C_1$–$C_6$ alkyl)aminocarbonyl, ($C_1$–$C_6$ alkyl)aminocarbonyloxy $C_1$–$C_6$ alkyl, or di($C_1$–$C_6$ alkyl)aminocarbonyloxy $C_1$–$C_6$ alkyl;

wherein W is hydrogen, chlorine, or bromine;

$R^{10}$ is hydrogen, $C_1$–$C_6$ alkyl, $C_1$–$C_6$ haloalkyl, $C_3$–$C_8$ cycloalkyl, $C_3$–$C_6$ alkenyl, $C_3$–$C_6$ haloalkenyl, $C_3$–$C_6$ alkynyl, $C_3$–$C_6$ haloalkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy)carbonyl $C_1$–$C_6$ alkyl, {($C_1$–$C_4$ alkoxy) $C_1$–$C_4$ alkoxy}carbonyl $C_1$–$C_6$ alkyl, ($C_3$–$C_8$ cycloalkoxy)carbonyl $C_1$–$C_6$ alkyl, —$CH_2CON(R^{11})R^{12}$, —$CH_2COON(R^{11})R^{12}$, —$CH(C_1$–$C_4$ alkyl)CON(R^{11})R^{12}$, or —$CH(C_1$–$C_4$ alkyl)COON(R^{11})R^{12}$;

$R^{11}$ and $R^{12}$ are independently hydrogen, $C_1$–$C_6$ alkyl, $C_1$–$C_6$ haloalkyl, $C_3$–$C_6$ alkenyl, $C_3$–$C_6$ alkynyl, cyano $C_1$–$C_6$ alkyl, $C_2$–$C_8$ alkoxyalkyl, $C_2$–$C_8$ alkylthioalkyl, carboxy $C_1$–$C_6$ alkyl, ($C_1$–$C_6$ alkoxy) carbonyl $C_1$–$C_6$ alkyl, or {($C_1$–$C_4$ alkoxy) $C_1$–$C_4$ alkoxy}carbonyl $C_1$–$C_6$ alkyl, or $R^{11}$ and $R^{12}$ are combined together to form tetramethylene, pentamethylene, or ethyleneoxyethylene;

$R^{13}$ is hydrogen, $C_1$–$C_6$ alkyl, $C_1$–$C_6$ haloalkyl, or $C_3$–$C_8$ cycloalkyl;

$R^{14}$ and $R^{15}$ are independently $C_1$–$C_6$ alkyl, $C_1$–$C_6$ haloalkyl, or phenyl optionally substituted with methyl or nitro;

$R^{16}$ is hydrogen, $C_1$–$C_6$ alkyl, $C_1$–$C_6$ haloalkyl, $C_2$–$C_6$ alkenyl, $C_2$–$C_6$ haloalkenyl, $C_2$–$C_6$ alkynyl, $C_2$–$C_6$ haloalkynyl, $C_2$–$C_8$ alkoxyalkyl, or hydroxy $C_1$–$C_6$ alkyl; and $R^{17}$ and $R^{18}$ are independently hydrogen or $C_1$–$C_6$ alkyl.

32. A compound according to claim 31, wherein $R^2$ is trifluoromethyl.

33. A compound according to claim 31, wherein Q is (Q-1).

34. A compound according to claim 31, wherein $R^1$ is hydrogen and $R^2$ is trifluoromethyl.

\* \* \* \* \*